US006288214B1

(12) United States Patent
Höök et al.

(10) Patent No.: US 6,288,214 B1
(45) Date of Patent: Sep. 11, 2001

(54) COLLAGEN BINDING PROTEIN COMPOSITIONS AND METHODS OF USE

(75) Inventors: Magnus Höök, Houston; Joseph M. Patti, Missouri City, both of TX (US); Karen House-Pompeo, Valdosta, GA (US); Narayana Sthanam, Vestavia; Jindrich Symersky, Birmingham, both of AL (US)

(73) Assignee: Texas A&M University Systems, College Station, TX (US)

( * ) Notice: Subject to any disclaimer, the term of this patent is extended or adjusted under 35 U.S.C. 154(b) by 0 days.

(21) Appl. No.: 08/856,253

(22) Filed: May 14, 1997

Related U.S. Application Data

(60) Provisional application No. 60/017,678, filed on May 16, 1996.

(51) Int. Cl.$^7$ .......................... C07K 16/00; C12P 21/08; A61K 39/395; A61K 39/40

(52) U.S. Cl. .................. 530/387.1; 530/350; 530/388.1; 530/388.4; 530/389.1; 424/130.1; 424/139.1; 424/141.1; 424/150.1; 424/165.1; 424/164.1; 514/2; 514/12

(58) Field of Search .............................. 530/350, 389.1, 530/388.1, 387.1, 388.4; 424/130.1, 139.1, 150.1, 141.1, 165.1, 164.1; 514/2, 12

(56) References Cited

U.S. PATENT DOCUMENTS

| | | | |
|---|---|---|---|
| 5,189,015 | * | 2/1993 | Hook et al. . |
| 5,491,130 | | 2/1996 | Roberts et al. ..................... 514/13 |
| 5,624,904 | * | 4/1997 | Kreiger et al. . |
| 5,656,439 | * | 8/1997 | Eyre . |
| 5,789,171 | * | 8/1998 | Smeltzer . |
| 5,851,794 | * | 12/1998 | Guss et al. . |
| 5,858,709 | * | 1/1999 | Hodgson et al. . |
| 5,965,383 | * | 10/1999 | Vogel et al. . |
| 5,980,908 | * | 11/1999 | Höök et al. . |
| 6,008,341 | * | 12/1999 | Foster et al. . |
| 6,013,482 | * | 1/2000 | Hodgson et al. . |

FOREIGN PATENT DOCUMENTS

| | | |
|---|---|---|
| 0 207 751 | 1/1987 | (EP) . |
| WO 92/07002 | 4/1992 | (WO) . |
| WO 94/11395 | 5/1994 | (WO) . |
| 9743314 | * 11/1997 | (WO) . |

OTHER PUBLICATIONS

Nilsson et al, J. Clin. Invest. 101:2640–2649, 1998.*
Foster et al, Trends in Microbiol 6/12:484–488, 1998.*
Smeltzer et al, J. Clinical Microbiology, 35/10:2444–2449, 1997.*
Patti et al, JBC, 270/20:12005–12011, 1995.*
Patti et al, Biochemistry, 32:11428–11435, 1993.*
Gillaspy et al, Infection and Immunity, 66/7:3170–3178, 1998.*
Mohamed et al, Infection and Immunity, 67/2:589–594, 1999.*
Clark et al, Microbial Pathogenesis, 17:239–251, 1994.*
Rich et al, Biochemistry, 37:15423–15433, 1998.*
Gillaspy et al, Gene, 196:239–248, 1997.*
Smeltzer et al, Gene, 196:249–259, 1997.*
Foster and McDevitt, "Surface–Associated Proteins of *Staphylococcus aureus*: Their Possible Roles in Virulence," FEMS *Microbiology Letters,* 118:199–206, 1994.
House–Pompeo, Boles, and Höök, "Characterization of Bacterial Adhesin Interactions with Extracellular Matrix Components Utilizing Biosensor Technology," *Methods: A Companion to Meth. in Enzym.,* 6:134–142, 1994.
International Search Report dated Nov. 10, 1997 (TAMK:193P).
Joh, H.J., House–Pompeo, K., Patti, J.M., Gurusiddappa, S. and Hook, M. (1994) Fibronectin receptors from gram–positive bacteria: Comparison of active sites. *Biochemistry* 33(20):6086–6092.
Patti et al., "Critical Residues in the Ligand–binding Site of the *Staphylococcus aureus* Collagen–binding Adhesin (MSCRAMM)," *J. Biol. Chem.,* 270:12005–12011, 1995.
Patti et al., "Molecular Characterization and Expression of a Gene Encoding a *Staphylococcus aureus* Collagen Adhesin," *J. Biol. Chem.,* 267:4766–4722, 1992.
Patti et al., "The *Staphylococcus aureus* Collagen Adhesin is a Virulence Determinant in Experimental Septic Arthritis," *Infect. Immun.,* 62:152–161, 1994.
Patti, Allen, McGavin, Höök, "MSCRAMM–Mediated Adherence of Microorganisims to Host Tissues," *Annu. Rev. Microbiol.,* 48:585–617, 1994.
Patti, Boles, Höök, "Identification and Biochemical Characterization of the Ligand Binding Domain of the Collagen Adhesin from *Staphylococcus aureus*," *Biochemistry,* 32:11428–11435, 1993.

(List continued on next page.)

*Primary Examiner*—Nita Minnifield
(74) *Attorney, Agent, or Firm*—Howrey Simon Arnold & White, LLP

(57) ABSTRACT

Disclosed are the cna gene and cna-derived nucleic acid segments from *Staphylococcus aureus*, and DNA segments encoding cna from related bacteria. Also disclosed are Col binding protein (CBP) compositions and methods of use. The CBP protein and antigenic epitopes derived therefrom are contemplated for use in the treatment of pathological infections, and in particular, for use in the prevention of bacterial adhesion to Col. DNA segments encoding these proteins and anti-(Col binding protein) antibodies will also be of use in various screening, diagnostic and therapeutic applications including active and passive immunization and methods for the prevention of bacterial colonization in an animal such as a human. These DNA segments and the peptides derived therefrom are contemplated for use in the preparation of vaccines and, also, for use as carrier proteins in vaccine formulations, and in the formulation of compositions for use in the prevention of *S. aureus* infection.

12 Claims, 12 Drawing Sheets

(2 of 12 Drawing Sheet(s) Filed in Color)

OTHER PUBLICATIONS

Ryding, U., Christensson, B., Soderquist, B. and Wadstrom, T., "Antibody response to *Staphylococcus aureus* Col binding protein in patients with S–aureus septicaemia and Col binding properties of corresponding strains," *J Med Microbiol* 43(5):328–334, 1995.

Speziale et al., "Binding of Collagen to *Staphylococcus aureus*," Cowan 1, *J. Bacteriol.*, 167:77–81, 1986.

Speziale et al., "Binding of Collagen to Group A, B, C, D and G Streptococci," FEMS *Microbiol. Lett.,* 48:47–51, 1987.

Switalski et al., "A collagen receptor on *Staphylococcus aureus* strains isolated from patients with septic arthritis mediates adhesion to cartliage," *Mol. Microbiol.*, 7:99–107, 1993.

Switalski et al., "Collagen Mediates Adhesion of Steptococcus mutans to Human Dentin," Infect. *Immun.,* 61(10):4119–4125, 1993.

Switalski et al., "Isolation and Characterization of a Putative Collagen Receptor from *Staphylococcus aureus* Strain Cowan 1*," *J. Biol. Chem.,* 264(35):21080–21086, 1989.

Westerlund and Korhonen, "Bacterial Proteins Binding to the Mammalian Extracelluar Matrix," *Molecular Microbiology,* 9(4):687–694, 1993.

Symersky et al., "Structure of the collagen–binding domain from a *Staphylococcus aureus* adhesin," *Nature Structural Biology* 4:833–838, Oct., 1997.

* cited by examiner

COLLAGEN BINDING PROTEIN COMPOSITIONS AND METHODS OF USE

The present application is a continuing application based on U.S. Provisional Patent Serial No. 60/017,678, filed May 16, 1996, the entire content of which is incorporated herein by reference.

The United States Government has certain rights to the present application pursuant to Grants HL473 13 and AI20624 from the National Institutes of Health.

1. BACKGROUND OF THE INVENTION

1.1 Field of the Invention

The present invention relates generally to the field of molecular biology. More particularly, certain embodiments concern methods and compositions comprising DNA segments, and proteins derived from bacterial species. More particularly, the invention provides cna and cna-derived nucleic acid compositions comprising a collagen (Col) binding protein (CBP) from *Staphylococcus aureus* and the corresponding peptide epitopes and protein sequences comprising native and synthetically-modified Col binding site domains. Various methods for making and using these DNA segments, DNA segments encoding synthetically-modified ligand binding site domains, and native and synthetic proteins are disclosed, such as, for example, the use of DNA segments as diagnostic probes and templates for protein production, and the use of proteins, fusion protein carriers and peptides in various pharmacological and immunological applications.

1.2 Description of the Related Art

1.2.1 Colonization by *Staphylococcus aureus*

*S. aureus* cells can colonize many different host tissues and cause various types of infections such as endocarditis, pneumonia, wound infections, osteomyelitis, and septic arthritis. Adherence of staphylococci to host tissues involves a family of adhesions that recognize extracellular matrix components and which have been named MSCRAMMs (Microbial Surface Components Recognizing Adhesive Matrix Molecules) (Patti et al., 1994a).

The expression of specific MSCRAMMs appears to be needed for the colonization of different types of tissues. For example, staphylococcal strains recovered from the joints of patients diagnosed with septic arthritis or osteomyelitis almost invariably express a CBP, whereas significantly fewer isolates obtained from wound infections express this adhesin. (Switalski et al., 1993a) Similarly, *S. aureus* strains isolated form the bones of patients with osteomyelitis often have an MSCRAMM recognizing the bone-specific protein, bone sialoprotein (BSP) (Rydén et al., 1989).

The cloning, sequencing, and expression of a gene cna, encoding a *S. aureus* CBP has been previously reported (Patti et al., 1992). The cna gene encodes an 133-kDa adhesin that contains structural features characteristic of surface proteins isolated from Gram-positive bacteria. It has been demonstrated that the CBP is required and sufficient for the adherence of *S. aureus* to Col-coated artificial substrates as well as to cartilage, a tissue rich in type II Col (Switalski et al., 1993a). All strains expressing the CBP were able to adhere to cartilage, whereas those strains lacking the MSCRAMMs did not adhere. Preincubation of *S. aureus* with polyclonal antibodies raised against the purified adhesin or saturation of the cartilage substrata with soluble recombinant CBP resulted in a complete inhibition of bacterial attachment (Switalski et al., 1993a).

*S. aureus* colonization of the articular cartilage within the joint space appears to be an important factor contributing to the development of septic arthritis. The importance of the CBP in the pathogenesis of septic arthritis was examined by comparing the virulence of two sets of *S. aureus* isogenic mutants in an animal model (Patti et al., 1994b). Greater than 70% of mice injected with $CNA^+$ strains (i.e. a clinical isolate expressing the CBP or a negative strain into which the cna gene had been introduced) developed clinical signs of arthritis, whereas less than 27% of the animals showed symptoms of disease when injected with $CNA^-$ strains (i.e. a strain lacking the cna gene or a strain in which the cna gene or a strain in which the cna gene had been inactivated through homologous recombination). Taken together these results demonstrate that the CBP plays an important role in the pathogenesis of septic arthritis induced by *S. aureus*.

Recently, the ligand-binding site has been localized within the N-terminal half of the CBP (Patti et al., 1993). By analyzing the Col binding activity of recombinant proteins corresponding to different segments of the MSCRAMM, a 168-amino-acid long protein fragment (corresponding to amino acid residues 151–318) that had appreciable Col binding activity was identified. Short truncations of this protein in the a N- or C terminus resulted in a loss of ligand binding activity but also resulted in conformational changes in the protein as indicated by circular dichroism spectroscopy. These results raised the possibility that the ligand-binding activity but also resulted in conformational changes in the protein as indicated by circular dichroism spectroscopy. These results raised the possibility the ligand-binding site of the MSCRAMM is contained within a short segment of amino acids and that flanking sequences are required for the proper folding of these residues in the ligand-binding site.

1.2.2 Role of *S. aureus* CBP in Human Disease

Hematogenously acquired bacterial arthritis remains a serious medical problem. This rapidly progressive and highly destructive joint disease is difficult to eradicate with less than 50% of the infected patients failing to recover without serious joint damage. *S. aureus* is the predominant pathogen isolated from adult patients with hematogenous (primary) and secondary osteomyelitis (Waldvogel and Vasey 1980), while also causing up to 90% of the cases of acute hematogenous osteomyelitis in otherwise healthy children (Cole 1982). Scanning electron microscopy studies have shown *S. aureus* to be intimately associated with cartilage and bone tissue retrieved from the site of infection. Additional microscopic evidence suggests the predominate attachment and subsequent colonization of cartilaginous rather than synovial surfaces (Voytek et al. 1988). An analysis of *S. aureus* strains isolated from patients diagnosed with osteomyelitis and septic arthritis revealed that almost all of the isolates contained a Col adhesin. In contrast, only one-third of the *S. aureus* strains isolated from patients with soft tissue infections expressed the Col adhesin (Switalski, Patti et al. 1993). These observations suggest that cell surface expression of the Col adhesin is an important virulence factor in staphylococcal mediated osteomyelitis and septic arthritis. Moreover, it has been observed that cartilage degradation following staphylococcal joint infection can be attributed to a direct interaction between bacteria and cartilage (Smith et al. 1982) in addition to the inflammatory response of the host (Smith et al. 1987). Individuals who require more than 6 days for the synovial fluid to become free of microorganisms typically result in poor clinical outcome (Ho and Su 1982). Poor outcomes include permanent disability with limited motion or persistent pain in the affected joint. Therefore, by inhibiting the initial attachment of bacteria to cartilage, the likelihood of subsequent joint destruction may be diminished.

1.3 Deficiencies in the Prior Art

It is clear that while several approaches to the treatment of bacterial diseases have experienced some success, many problems remain, including antibiotic resistance, variability of antigens between species and species variation through mutation of antigens, as well as the need to protect susceptible groups such as young children, the elderly and other immunocompromised patients. Thus, there exists an immediate need for an effective treatment for *S. aureus* infection, and vaccines against this pathogen.

2. SUMMARY OF THE INVENTION

The present invention overcomes one or more of these and other drawbacks inherent in the prior art by providing novel compositions and methods for their use in the treatment of *S. aureus* infection using non-antibiotic strategies. Disclosed are methods for the use of novel peptide and antibody compositions in the treatment of *S. aureus* infection mediated by the inhibition of bacterial binding to the host cell ECM component, Col. Also disclosed are methods for active and passive immunization against *S. aureus* and related species using novel native and site-specifically-altered CBP compositions and CBP-derived epitopic peptides from bacterial species. Particular aspects of the invention relate to novel nucleic acid segments encoding these peptides and epitopes, and methods for the use of such nucleic acid segments in a variety of diagnostic and therapeutic regimens. Also obtained are peptide compositions derived from CBP which comprise the Col binding domain. Using crystal structure analyses, the inventors have developed site-specific mutations in CBP-encoding DNA segments which give rise to altered Col binding domains.

In important embodiments methods and compositions are obtained for inhibiting the binding of *S. aureus* to Col. These compositions are useful in the prevention of bacterial adhesion to extracellular matrix components such as Col, and in the inhibition of bacterial colonization to collagenous substrata. In addition, the invention encompasses the use of CBP or cna gene sequences to produce antibodies which protect against staphylococcal infections.

In another embodiment, the invention relates to a method of preventing a *S. aureus*-mediated disease in an animal. The method generally involves identifying an animal suspected of infection with *S. aureus* and administering to the animal a collagen binding protein or antibody composition effective to prevent the disease in the animal.

In a further embodiment, the invention relates to a method of increasing phagocytosis of an *S. aureus* cell by a macrophage cell. The method generally involves providing to the macrophage cell a pharmaceutically-acceptable collagen binding protein or antibody composition in an amount effective to increase the phagocytosis of the bacteria by the macrophage.

Preferably, the collagen binding protein composition comprises the amino acid sequence of SEQ ID NO:2, SEQ ID NO:4, or SEQ ID NO:6, or the antibody specifically binds to the amino acid sequence of SEQ ID NO:2, SEQ ID NO:4, or SEQ ID NO:6.

In a related embodiment, the invention relates to a method of enhancing intracellular killing of an *S. aureus* cell in a macrophage cell. This method comprises providing to a macrophage cell a pharmaceutically-acceptable collagen binding protein or antibody composition in an amount effective to enhance the intracellular killing of the *S. aureus* cell in the macrophage.

2.1 CNA Nucleic Acid Compositions

The invention provides nucleic acid sequences encoding CBP. As used herein, a gene encoding CBP means a nucleic acid sequence encoding Col binding protein. A preferred nucleic acid sequence encoding a CBP gene is the nucleotide sequence of SEQ ID NO:1, or a strain variant or an active fragment thereof. It is expected that the gene encoding CBP will vary in nucleic acid sequence from strain to strain, but that the variation in nucleic acid sequence will not preclude hybridization between sequences encoding CBP of each strain under strict hybridization conditions.

As used herein, a strain variant of CBP means any polypeptide encoded, in whole or in part, by a nucleic acid sequence which hybridizes under strict hybridization conditions to a nucleic acid sequence from any of SEQ ID NO:1, SEQ ID NO:3, and SEQ ID NO:5 encoding the M17, M31 and M55 epitopes of a *S. aureus* CBP, respectively. The amino acid sequence of M17, M31 and M55 peptides is given in SEQ ID NO:2, SEQ ID NO:4, and SEQ ID NO:6 respectively. One of skill in the art will understand that strain variants of CBP include those proteins encoded by nucleic acid sequences which may be amplified using a nucleic acid sequence of any of SEQ ID NO:1, SEQ ID NO:3, and SEQ ID NO:5.

In related embodiments, the invention also comprises strain variants of CBP and the cna gene(s) encoding CBPs. Strain variants are those nucleic acid compositions and polypeptide compositions isolated from strains of *S. aureus* and related gram-positive bacteria which express CBPs, and which adhere to Col substrates.

Aspects of the invention concern the identification of such strain variants using diagnostic methods and kits described herein. In particular, methods utilizing cna gene sequences as nucleic acid hybridization probes and/or anti-CBP antibodies in western blots or related analyses are useful for the identification of such strain variants. The identity of potential strain variants of CBP may be confirmed by Col binding assays, e.g., by blot analysis with labeled Col, or alternatively by the demonstrating the ability of the strain-variant CBP to lessen or prevent adherence of *S. aureus* and related bacteria Col.

As used herein, a CBP is a protein which confers protection against staphylococcal or streptococcal infection. A CBP or fragments thereof may prevent or lessen adhesion of *S. aureus* to Col, or prevent or lessen adhesion the severity of any of the disorders associated with *S. aureus* infection, including sepsis, skin lesions, septic arthritis, endocarditis, mastitis, pneumonia, neurological disorders, and other diseases which result from the colonization of *S. aureus* or related organisms to Col-containing substrata.

An important aspect of the present invention concerns isolated DNA segments and recombinant vectors encoding CBP, and the creation and use of recombinant host cells through the application of DNA technology, that express CBP gene and CBP-derived gene products. As such, the invention concerns DNA segment comprising an isolated gene that encodes a protein or peptide that includes an amino acid sequence essentially as set forth by a contiguous sequence from SEQ ID NO:2, SEQ ID NO:4, or SEQ ID NO:6. These DNA segments are exemplified in SEQ ID NO:1, SEQ ID NO:3, and SEQ ID NO:5, respectively. Compositions that include a purified protein that has an amino acid sequence essentially as set forth by the amino acid sequence of SEQ ID NO:2, SEQ ID NO:4, or SEQ ID NO:6 are also encompassed by the invention.

Regarding the novel protein CBP epitopes, the present invention concerns DNA segments, that can be isolated from virtually any bacterial source, that are free from total genomic DNA and that encode proteins or peptides having CBP-like activity. DNA segments encoding CBP-like species may prove to encode proteins, polypeptides, subunits, functional domains, and the like.

As used herein, the term "DNA segment" refers to a DNA molecule that has been isolated free of total genomic DNA of a particular species. Therefore, a DNA segment encoding CBP refers to a DNA segment that contains CBP coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified CBP gene refers to a DNA segment including CBP coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, extra-genomic and plasmid-encoded sequences and smaller engineered gene segments that express, or may be adapted to express, proteins, polypeptides or peptides. Such segments may be naturally isolated, or modified synthetically by the hand of man.

"Isolated substantially away from other coding sequences" means that the gene of interest, in this case, a gene encoding CBP, forms the significant part of the coding region of the DNA segment, and that the DNA segment does not contain large portions of naturally-occurring coding DNA, such as large chromosomal fragments or other functional genes or polypeptide coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a CBP species that includes within its amino acid sequence an amino acid sequence essentially as set forth in SEQ ID NO:2, SEQ ID NO:4, or SEQ ID NO:6. In other particular embodiments, the invention concerns isolated DNA segments and recombinant vectors incorporating DNA sequences that include within their sequence a nucleotide sequence essentially as set forth in SEQ ID NO:1, SEQ ID NO:3, or SEQ ID NO:5.

The term "a sequence essentially as set forth in SEQ ID NO:2, SEQ ID NO:4, or SEQ ID NO:6" means that the sequence substantially corresponds to a portion of SEQ ID NO:2, SEQ ID NO:4, or SEQ ID NO:6 and has relatively few amino acids that are not identical to, or a biologically functional equivalent of, the amino acids of SEQ ID NO:2, SEQ ID NO:4, or SEQ ID NO:6. The term "biologically functional equivalent" is well understood in the art and is further defined in detail herein (for example, see Illustrative Embodiments). Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:2, SEQ ID NO:4, or SEQ ID NO:6 will be sequences that are "essentially as set forth in SEQ ID NO:2, SEQ ID NO:4, or SEQ ID NO:6".

In certain other embodiments, the invention concerns isolated DNA segments and recombinant vectors that include within their sequence a nucleic acid sequence essentially as set forth in SEQ ID NO:1, SEQ ID NO:3, or SEQ ID NO:5. The term "essentially as set forth in SEQ ID NO:1, SEQ ID NO:3, or SEQ ID NO:5" is used in the same sense as described above and means that the nucleic acid sequence substantially corresponds to a portion of SEQ ID NO:1, SEQ ID NO:3, or SEQ ID NO:5 and has relatively few codons that are not identical, or functionally equivalent, to the codons of SEQ ID NO:1, SEQ ID NO:3, or SEQ ID NO:5. Again, DNA segments that encode proteins exhibiting CBP-like activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various upstream or downstream regulatory or structural genes.

Naturally, the present invention also encompasses DNA segments that are complementary, or essentially complementary, to the sequence set forth in SEQ ID NO:1, SEQ ID NO:3, or SEQ ID NO:5. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1, SEQ ID NO:3, or SEQ ID NO:5, under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch identical to or complementary to SEQ ID NO:1, SEQ ID NO:3, or SEQ ID NO:5, such as about 14 nucleotides, and that are up to about 10,000 or about 5,000 base pairs in length, with segments of about 3,000 base pairs preferred in certain cases. DNA segments with total lengths of about 2,000, about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002 and the like.

It will also be understood that this invention is not limited to the particular nucleic acid sequences disclosed in SEQ ID NO:1, SEQ ID NO:3, or SEQ ID NO:5, or to the amino acid sequences disclosed in SEQ ID NO:2, SEQ ID NO:4, or SEQ ID NO:6. Recombinant vectors and isolated DNA segments may therefore variously include the CBP epitope encoding regions themselves, coding regions bearing selected alterations or modifications in the basic coding region, or they may encode larger polypeptides that nevertheless include CBP-derived coding regions or may encode biologically functional equivalent proteins or peptides that have variant amino acids sequences.

The DNA segments of the present invention encompass biologically functional equivalent CBP-derived proteins and peptides, in particular those CBP and related proteins isolated from prokaryotic sources, and particularly bacteria. DNA segments isolated from species of staphylococci and streptococci and related bacteria which are shown to bind Col are particularly preferred for use in the methods disclosed herein. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the CBP or CBP-derived coding regions are aligned within the same expression unit with other proteins or peptides having desired functions, such as for purification or immunodetection purposes (e.g., proteins that may be purified by affinity chromatography and enzyme label coding regions, respectively).

2.2 Recombinant Expression of CBP and CBP-Derived Epitopes

The present invention also concerns recombinant host cells for expression of an isolated cna gene, or for a DNA sequence encoding one or more epitopic peptides derived from a cna-encoding protein. It is contemplated that virtually any host cell may be employed for this purpose, but certain advantages may be found in using a bacterial host cell such as E. coli, S. typhimurium, B. subtilis, or S. aureus, S. dysgalactiae, S. pyogenes or other Gram-positive species. Expression in eukaryotic cells is also contemplated such as those derived from yeast, insect, or mammalian cell lines. These recombinant host cells may be employed in connection with "overexpressing" CBP proteins, that is, increasing the level of expression over that found naturally in S. aureus.

Proteins of amino acid sequence derived, from or similar to, CBP are expected to have affinity for Col and can be purified from other constituents of S. aureus or recombinant host cells by chromatography on matrices containing Col, so-called "affinity chromatography." CBPs may also be purified by methodologies not relying on affinity for Col such as ion exchange chromatography, size exclusion chromatography, metal chelation chromatography, or the like. Buffer, detergent, and other conditions may be dissimilar from those optimal for "affinity chromatography." In a preferred embodiment, an affinity matrix comprising Type II Col or a related Col type (e.g., Type I, Type III, Type V, Type IX, etc.) may be used for the isolation of CBPs from solution, or alternatively, isolation of intact bacteria expressing CBPs, or even membrane fragments of bacteria expressing CBPs.

A particular aspect of this invention provides novel ways in which to utilize recombinant CBPs or CBP-derived peptides, nucleic acid segments encoding these peptides, recombinant vectors and transformed host cells comprising cna or cna-derived DNA segments, recombinant vectors and transformed host cells comprising cna or cna-derived DNA segments, and recombinant vectors and transformed host cells comprising S. aureus cna-derived DNA segments. In particular embodiments, genetically-engineered nucleic acid segments and CBP proteins are obtained which have altered Col binding site domains. Using the methods disclosed herein, the inventors have developed site-specifically altered CBPs which have reduced affinity for Col. As is well known to those of skill in the art, many such vectors and host cells are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a protein or peptide of interest (e.g., a CBP, and particularly a CBP from S. aureus, or related bacterium, and does not include any coding or regulatory sequences that would have an adverse effect on cells). Therefore, it will also be understood that useful nucleic acid sequences may include additional residues, such as additional non-coding sequences flanking either of the 5' or 3' portions of the coding region or may include various regulatory sequences.

After identifying an appropriate epitope-encoding nucleic acid molecule, it may be inserted into any one of the many vectors currently known in the art, so that it will direct the expression and production of the protein or peptide epitope of interest (e.g., a CBP from S. aureus) when incorporated into a host cell. In a recombinant expression vector, the coding portion of the DNA segment is positioned under the control of a promoter. The promoter may be in the form of the promoter which is naturally associated with a CBP-encoding nucleic acid segment, as may be obtained by isolating the 5' non-coding sequences located upstream of the coding segment, for example, using recombinant cloning and/or PCR™ technology, in connection with the compositions disclosed herein. Direct amplification of nucleic acids using the PCR™ technology of U.S. Pat. Nos. 4,683,195 and 4,683,202 (herein incorporated by reference) are particularly contemplated to be useful in such methodologies.

In certain embodiments, it is contemplated that particular advantages will be gained by positioning the CBP-encoding DNA segment under the control of a recombinant, or heterologous, promoter. As used herein, a recombinant or heterologous promoter is intended to refer to a promoter that is not normally associated with a cna or cna-like gene segment in its natural environment. Such promoters may include those normally associated with other MSCRAMM-encoding genes, and/or promoters isolated from any other bacterial, viral, eukaryotic, or mammalian cell. Naturally, it will be important to employ a promoter that effectively directs the expression of the DNA segment in the particular cell containing the vector comprising the CBP-encoding nucleic acid segment.

The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides.

Prokaryotic expression of nucleic acid segments of the present invention may be performed using methods known to those of skill in the art, and will likely comprise expression vectors and promotor sequences such as those obtained by tac, trp, lac, lacUV5 or T7. When expression of the recombinant CBP proteins is desired in eukaryotic cells, a number of expression systems are available and known to those of skill in the art. An exemplary eukaryotic promoter system contemplated for use in high-level expression is the Pichia expression vector system (Pharmacia LKB Biotechnology).

In connection with expression embodiments to prepare recombinant CBP and peptides, it is contemplated that longer DNA segments will most often be used, with DNA segments encoding the entire CBP or functional domains, epitopes, ligand binding domains, subunits, etc. being most preferred. However, it will be appreciated that the use of shorter DNA segments to direct the expression of CBP peptides or epitopic core regions, such as may be used to generate anti-CBP antibodies, also falls within the scope of the invention. DNA segments that encode peptide antigens from about 15 to about 100 amino acids in length, or more preferably, from about 15 to about 50 amino acids in length are contemplated to be particularly useful. Exemplary DNA segments encoding peptide epitopes of the Col-binding protein which the inventors have shown to be useful in preventing the binding to Col include the polynucleotides disclosed in SEQ ID NO:1, SEQ ID NO:3, and SEQ ID NO:5.

The cna gene and cna-derived DNA segments may also be used in connection with somatic expression in an animal or in the creation of a transgenic animal. Again, in such embodiments, the use of a recombinant vector that directs the expression of the full length or one or more active CBP epitopes is particularly contemplated. Expression of cna transgene in animals is particularly contemplated to be useful in the production of anti-CBP antibodies for use in passive immunization methods for prevention of staphylococcal and streptococcal adhesion to Col.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. For eukaryotic expression, the currently preferred promoters are those such as CMV, RSV LTR, the SV40 promoter alone, and the SV40 promoter in combination with the SV40 enhancer. In preferred embodiments, the expression of recombinant CBPs is carried out using prokaryotic expression systems, and in particular bacterial systems such as *E. coli*. Such prokaryotic expression of nucleic acid segments of the present invention may be performed using methods known to those of skill in the art, and will likely comprise expression vectors and promotor sequences such as those obtained by tac, trp, lac, lacUV5 or T7 promoters.

For the expression of CBP and CBP-derived epitopes, once a suitable clone or clones have been obtained, whether they be native sequences or genetically-modified, one may proceed to prepare an expression system for the recombinant preparation of CBP or CBP-derived peptides. The engineering of DNA segment(s) for expression in a prokaryotic or eukaryotic system may be performed by techniques generally known to those of skill in recombinant expression. It is believed that virtually any expression system may be employed in the expression of CBP or CBP-derived epitopes.

Alternatively, it may be desirable in certain embodiments to express CBP or CBP-derived epitopes in eukaryotic expression systems. The DNA sequences encoding the desired CBP or CBP-derived epitope (either native or mutagenized) may be separately expressed in bacterial systems, with the encoded proteins being expressed as fusions with b-galactosidase, ubiquitin, *Schistosoma japonicum* glutathione S-transferase, *S. aureus* Protein A, maltose binding protein, and the like. It is believed that bacterial expression will ultimately have advantages over eukaryotic expression in terms of ease of use and quantity of materials obtained thereby.

It is proposed that transformation of host cells with DNA segments encoding such epitopes will provide a convenient means for obtaining CBP or CBP-derived peptides. Genomic sequences are suitable for eukaryotic expression, as the host cell will, of course, process the genomic transcripts to yield functional mRNA for translation into protein.

It is similarly believed that almost any eukaryotic expression system may be utilized for the expression of CBP and CBP-derived epitopes, e.g., baculovirus-based, glutamine synthase-based or dihydrofolate reductase-based systems may be employed. In preferred embodiments it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes nucleic acid sequences encoding CBP or CBP-derived peptides, an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

It is contemplated that virtually any of the commonly employed host cells can be used in connection with the expression of the CBP and CBP-derived epitopes in accordance herewith. Examples include cell lines typically employed for eukaryotic expression such as 239, AtT-20, HepG2, VERO, HeLa, CHO, WI 38, BHK, COS-7, RIN and MDCK cell lines.

It is further contemplated that the CBP or epitopic peptides derived from native or recombinant CBPs may be "overexpressed", i.e., expressed in increased levels relative to its natural expression in human cells, or even relative to the expression of other proteins in a recombinant host cell containing CBP-encoding DNA segments. Such overexpression may be assessed by a variety of methods, including radiolabeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural CBP-producing cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a CBP or CBP-derived epitope has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a single structural gene, an entire genomic clone comprising a structural gene and flanking DNA, or an operon or other functional nucleic acid segment which may also include genes positioned either upstream and/or downstream of the promotor, regulatory elements, or structural gene itself, or even genes not naturally associated with the particular structural gene of interest.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive eukaryotic promoters include viral promoters such as the cytomegalovirus (CMV) promoter, the Rous sarcoma long-terminal repeat (LTR) sequence, or the SV40 early gene promoter. The use of these constitutive promoters will ensure a high, constant level of expression of the introduced genes. The inventors have noticed that the level of expression from the introduced genes of interest can vary in different clones, or genes isolated from different strains or bacteria. Thus, the level of expression of a particular recombinant gene can be chosen by evaluating different clones derived from each transfection study; once that line is chosen, the constitutive promoter ensures that the desired level of expression is permnanently maintained. It may also be possible to use promoters that are specific for cell type used for engineering, such as the insulin promoter in insulinoma cell lines, or the prolactin or growth hormone promoters in anterior pituitary cell lines.

2.3 Immunological Detection of CBP and Bacteria Expressing CBPs

A further aspect of the invention is the preparation of immunological compositions, and in particular anti-CBP antibodies for diagnostic and therapeutic methods relating to the detection and treatment of infections caused by S. aureus and related Gram-positive species. In preferred embodiments, antibody compositions are disclosed which bind to the site-specifically altered recombinant CBPs described in the present invention. Also disclosed are antibodies which recognize specific native and synthetically-mutated Col binding domain epitopes within the CBPs. The inventors contemplate such antibodies to be useful in both diagnostic screening assays, processes for purifying Col, detecting anti-CBP antibodies, as well as their use in passive immunization of an animal to prevent bacterial sepsis, colonization, or binding to the ECM component Col.

2.4 Methods for Producing an Immune Response

Also disclosed is a method of generating an immune response in an animal. The method generally involves administering to an animal a pharmaceutical composition comprising an immunologically effective amount of a peptide composition disclosed herein. Preferred peptide compositions include the peptide disclosed in any of SEQ ID NO:2, SEQ ID NO:4, or SEQ ID NO:6.

The invention also encompasses CBP and CBP-derived peptide antigen compositions together with pharmaceutically-acceptable excipients, carriers, diluents, adjuvants, and other components, such as additional peptides, antigens, or outer membrane preparations, as may be employed in the formulation of particular vaccines.

The nucleic acid sequences of the present invention encode CBP and are useful to generate pure recombinant CBP for administration to a host. Such administration is useful as a vaccine to induce therapeutic antibodies that prevent adherence of S. aureus to the host's tissues.

It is shown herein that antisera raised against and reactive with CBP inhibits binding, promotes phagocytosis, and enhances intracellular killing by macrophages. Thus it is contemplated that administration of antibodies reactive with CBP to at-risk subject will be effective for prophylaxis of, and in the case of infected subjects for therapy of, bacterial infection.

Antibodies may be of several types including those raised in heterologous donor animals or human volunteers immunized with CBPs, monoclonal antibodies (mAbs) resulting from hybridomas derived from fusions of B cells from CBP-immunized animals or humans with compatible myeloma cell lines, so-called "humanized" mAbs resulting from expression of gene fusions of combinatorial determining regions of mAb-encoding genes from heterologous species with genes encoding human antibodies, or CBP-reactive antibody-containing fractions of plasma from human donors. It is contemplated that any of the techniques described above might be used for the vaccination of subjects for the purpose of antibody production. Optimal dosing of such antibodies is highly dependent upon the pharmacokinetics of the specific antibody population in the particular species to be treated. It is contemplated that the duration of dosing maintaining anti-CBP levels at these inhibitory antibody concentrations would be for at least four to eight weeks following presumptive exposure to S. aureus, or throughout the duration of symptoms of disease and for at least four to eight weeks after cessation of these symptoms.

Using the peptide antigens described herein, the present invention also provides methods of generating an immune response, which methods generally comprise administering to an animal, a pharmaceutically-acceptable composition comprising an immunologically effective amount of a CBP peptide composition. Preferred animals include mammals, and particularly humans. Other preferred animals include murines, bovines, equines, porcines, canines, and felines. The composition may include partially or significantly purified CBP peptide epitopes, obtained from natural or recombinant sources, which proteins or peptides may be obtainable naturally or either chemically synthesized, or alternatively produced in vitro from recombinant host cells expressing DNA segments encoding such epitopes. Smaller peptides that include reactive epitopes, such as those between about 10 and about 50, or even between about 50 and about 100 amino acids in length will often be preferred. The antigenic proteins or peptides may also be combined with other agents, such as other peptide or nucleic acid compositions, if desired.

By "immunologically effective amount" is meant an amount of a peptide composition that is capable of generating an immune response in the recipient animal. This includes both the generation of an antibody response (B cell response), and/or the stimulation of a cytotoxic immune response (T cell response). The generation of such an immune response will have utility in both the production of useful bioreagents, e.g., CTLs and, more particularly, reactive antibodies, for use in diagnostic embodiments, and will also have utility in various prophylactic or therapeutic embodiments. Therefore, although these methods for the stimulation of an immune response include vaccination regimens designed to prevent or lessen significant infections caused by bacteria expressing a CBP, and treatment regimens that may lessen the severity or duration of any infection, it will be understood that achieving either of these end results is not necessary for practicing these aspects of the invention. Such treatment methods may be used particularly for the treatment of infections caused by pathogens such as *S. aureus*, related species, and other bacteria which express CBPs and adhere to Col.

Further means contemplated by the inventors for generating an immune response in an animal includes administering to the animal, or human subject, a pharmaceutically-acceptable composition comprising an immunologically effective amount of a nucleic acid composition encoding a CBP epitope, or an immunologically effective amount of an attenuated live organism that includes and expresses such a nucleic acid composition. The "immunologically effective amounts" are those amounts capable of stimulating a B cell and/or T cell response.

Immunoformulations of this invention, whether intended for vaccination, treatment, or for the generation of antibodies useful in the detection of *S. aureus* and related bacteria, the prevention of bacterial adhesion, or in the case of bacterial colonization, promotion of bacterial adhesion to ECM components such as Col, may comprise native, or synthetically-derived antigenic peptide fragments from these proteins. As such, antigenic functional equivalents of the proteins and peptides described herein also fall within the scope of the present invention. An "antigenically functional equivalent" protein or peptide is one that incorporates an epitope that is immunologically cross-reactive with one or more epitopes derived from any of the particular MSCRAMM proteins disclosed (e.g., CBPs), and particularly the CBP of *S. aureus*. Antigenically functional equivalents, or epitopic sequences, may be first designed or predicted and then tested, or may simply be directly tested for cross-reactivity.

In still further embodiments, the present invention concerns immunodetection methods and associated kits. It is contemplated that the proteins or peptides of the invention may be employed to detect antibodies having reactivity therewith, or, alternatively, antibodies prepared in accordance with the present invention, may be employed to detect CBP or peptides. Either type of kit may be used in the immunodetection of compounds, present within clinical samples, that are indicative of infections caused by gram-positive bacteria expressing a CBP, and in particular *S. aureus*. The kits may also be used in antigen or antibody purification, as appropriate.

In general, the preferred immunodetection methods will include first obtaining a sample suspected of containing a CBP-reactive antibody, such as a biological sample from a patient, and contacting the sample with a first CBP or peptide under conditions effective to allow the formation of an immunocomplex (primary immune complex). One then detects the presence of any primary immunocomplexes that are formed.

Contacting the chosen sample with the CBP or peptide under conditions effective to allow the formation of (primary) immune complexes is generally a matter of simply adding the protein or peptide composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in the art and may be achieved through the application of numerous approaches known to the skilled artisan and described in various publications, such as, e.g., Nakamura et al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies and the remaining bound label is then detected.

For diagnostic purposes, it is proposed that virtually any sample suspected of containing the antibodies of interest may be employed. Exemplary samples include clinical samples obtained from a patient such as blood or serum samples, bronchoalveolar fluid, ear swabs, sputum samples, middle ear fluid or even perhaps urine samples may be employed. This allows for the diagnosis of infections caused by Gram-positive bacterium, and in particular, *S. aureus*. Furthermore, it is contemplated that such embodiments may have application to non-clinical samples, such as in the titering of antibody samples, in the selection of hybridomas, the detection of anti-CBP antibodies in a sample, the purification of CBPs, and the prevention of bacterial adhesion to Col, and the like. Alternatively, the clinical samples may be from veterinary sources and may include such domestic animals as cattle, sheep, and goats. Samples from feline, canine, and equine sources may also be used in accordance with the methods described herein.

In related embodiments, the present invention contemplates the preparation of kits that may be employed to detect the presence of CBP-specific antibodies in a sample. Generally speaking, kits in accordance with the present invention will include a suitable protein or peptide together with an immunodetection reagent, and a means for containing the protein or peptide and reagent.

The immunodetection reagent will typically comprise a label associated with a CBP or peptide, or associated with a secondary binding ligand. Exemplary ligands might include a secondary antibody directed against the first CBP or peptide or antibody, or a biotin or avidin (or streptavidin) ligand having an associated label. Detectable labels linked to antibodies that have binding affinity for a human antibody are also contemplated, e.g., for protocols where the first reagent is a CBP peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is obtained, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

2.5 Methods for Inhibiting Bacterial Adhesion to Col

In addition, the CBP is useful as an agent to block *S. aureus* adherence to Col. In a preferred embodiment of the invention, a therapeutically effective dose of a CBP-derived epitope is administered to a subject to prevent or block adhesion of *S. aureus* to the host's tissues by conventional methods. The CBP composition is preferably systemically administered, (i.e. by oral, intravenous, and/or parenteral routes) but may also be applied topically, e.g., to a localized tissue site, wound, lesion, or any other location where the prevention of *S. aureus* adhesion is desired. The term therapeutically effective dose means that amount of a CBP composition which is sufficient to lessen or prevent adherence of *S. aureus* to a subject or to neutralize the known deleterious effects of *S. aureus* infection. Such a dose may readily be determined by known clinical, diagnostic, and pharmacological methods. Absent adhesion of the bacteria to the tissues, the disease-inducing effects of the microorganism are halted, thus the CBP of the present invention is useful as a therapeutic agent to prevent adhesion of *S. aureus* and thereby lessen or prevent disease induced by this microorganism.

2.6 Methods for Identifying Inhibitors of Col Binding by CBPs

In a preferred embodiment, the novel recombinant polypeptides of the present invention are used in methods to isolate, identify, and characterize compositions which inhibit the binding of Col to CBPs. Such inhibitors are useful in the prevention of bacterial adhesion to extracellular matrices containing Col. These inhibitors provide a non-antibiotic strategy for the prevention of bacterial infection in an animal, particularly through the inhibition of Col binding to proteins located on the bacterial cell surface. In particular, the inventors contemplate the use of CBP and CBP-derived peptides to define and screen small molecule inhibitors. A particular utility of these inhibitors is the prevention of bacterial adhesion to exposed collagenous tissues or to Col accumulating on artificial joints, medical implants, and other surgical devices which may be susceptible to Col coating and subsequent bacterial adherence to the Col-coated surfaces. Likewise, the availability of the crystal structure of the CBP also now permits for the first time design of peptidemimetics which may also serve to inhibit the binding of CBP to Col.

2.7 Hybridization Embodiments

In addition to their use in directing the expression of CBP and CBP-derived epitopic peptides, the nucleic acid sequences disclosed herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous sequence of any of SEQ ID NO:1, SEQ ID NO:3, or SEQ ID NO:5 will find particular utility. Longer contiguous identical or complementary sequences, e.g., those of about 20, 30, 40, 50, 100, 200, 500, 1000 (including all intermediate lengths) and even up to fall length sequences will also be of use in certain embodiments.

The ability of such nucleic acid probes to specifically hybridize to CBP-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to SEQ ID NO:1, SEQ ID NO:3, or SEQ ID NO:5, are particularly contemplated as hybridization probes for use in, e.g., Southern and Northern blotting. This would allow CBP structural or regulatory genes to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 14 and about 100 nucleotides, but larger contiguous complementarity stretches may be used, according to the length complementary sequences one wishes to detect.

The use of a hybridization probe of about 14–25 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1, SEQ ID NO:3, and SEQ ID NO:5, and to select any continuous portion of the sequence, from about 14–25 nucleotides in length up to and including the full length sequence, that one wishes to utilize as a probe or primer. The choice of probe and primer sequences may be governed by various factors, such as, by way of example only, one may wish to employ primers from towards the termini of the total sequence.

The process of selecting and preparing a nucleic acid segment that includes a contiguous sequence from within SEQ ID NO:1, SEQ ID NO:3, or SEQ ID NO:5 may alternatively be described as preparing a nucleic acid fragment. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of the entire cna gene or gene fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as obtained by about 0.02 M to about 0.15 M NaCl at temperatures of 50° C. to 70° C. Such selective conditions tolerate little, if any, mismatch between the probe and the template or target strand, and would be particularly suitable for isolating CBP genes.

Of course, for some applications, for example, where one desires to prepare mutants employing a mutant primer strand hybridized to an underlying template or where one seeks to isolate CBP-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.8 Antibody Compositions

In a preferred embodiment, administration of a therapeutically effective dose of CBP to a subject induces in the subject antibodies which bind and neutralize *S. aureus* present in the subject, thereby preventing the deleterious effects of this microorganism. Alternatively, anti-CBP epitope antibodies generated in a first host animal provide antibodies which can be administered to a second subject for passive immunization or treatment against *S. aureus* infection. Such antibodies are also useful as a diagnostic screen for the presence of *S. aureus* in a test sample, using conventional immunoassay techniques.

In the present invention, novel nucleic acid sequences are disclosed which encode site-specifically modified CBPs of *S. aureus*. These synthetic variants are prepared by the methods disclosed herein, and encode CBPs having modified Col binding domains.

In certain aspects, the present invention concerns novel antibody compositions which inhibit Col binding to bacteria. In particular, antibodies to native and synthetically-modified epitopes from CBPs have been developed which inhibit Col binding to CBPs both in vitro and in vivo. In particular, proteins, peptides and peptide epitopes have been produced to provide vaccine compositions useful in the prevention of bacterial infection and antibody compositions useful in the prevention of Col binding to such organisms.

In other embodiments, the present invention encompasses antibody compositions which enhance Col binding to bacterial cells. These aspects provide methods and compositions for producing bacterial colonization of an animal host with attenuated, or avirulent bacterial strains expressing cell surface CBP epitopes.

In one aspect, the invention discloses an antibody that interacts with a CBP domain of a bacterial cna gene product, and particularly, a CBP domain of an *S. aureus* cna gene product. Such antibody may be monoclonal, or preferably polyclonal. In another aspect, the invention discloses an antibody which inhibits bacterial adhesion, and the binding of the gene product to Col.

Also disclosed is a method for detecting a bacterium expressing a CBP in a sample. The method generally involves obtaining a sample suspected of containing a bacterium expressing such a protein, then contacting the sample with an antibody composition disclosed herein, and detecting the formation of immune complexes. In preferred embodiments, the bacterium is *S. aureus, S. dysgalactiae, S. pyogenes*, on a related species of Gram-positive bacteria.

Other aspects of the invention include methods of inhibiting bacterial colonization, and particularly colonization by *S. aureus, S. dysgalactiae, S. pyogenes*, on a related species of Gram-positive bacteria, in an animal by administering to the animal an antibody of the present invention which prevents or significantly reduces the binding of Col to the CBP expressed by the bacteria. Administration of the antibody composition may be prophylactically prior to and/or following diagnosis of infection or other multisystemic disorders caused by bacterial infection which may involve the skin, joints, heart, and central nervous system. The administration may also be made in passive immunization protocols designed to prevent and/or ameliorate systemic infections by susceptible pathogens, and in particular, to ameliorate the effects of infections by pathogenic streptococci, staphylococci, and related Gram-positive bacteria.

2.9 Nucleic Acid Segments and Vectors

The present invention includes proteins expressed from genes encoding a CBP such as that protein expressed from the DNA insert of recombinant clones comprising site-specifically modified CBPs from S. aureus. Also included are strain variants of the cna gene derived from S. aureus which also encode proteins capable of binding Col, which may hybridize to cna DNAs under conditions of moderate or high stringency, or which may serve as templates for gene amplification by PCR™ using oligonucleotide primers derived from cna or cna-derived nucleic acid sequences. It is understood that these variants may include genes containing codons not identical in nucleotide sequence to those of the cna gene of S. aureus, but encoding the same, or functionally equivalent amino acid, as is expected by those practiced in the art who understand the degeneracy of the genetic code. These variants may also include those genes similar to the cna gene from S. aureus, but having codons specifying relatively few amino acids that are different from those of the protein(s) encoded by S. aureus, or having somewhat fewer or greater numbers of these codons. Accordingly such sequences include those that have between about 60% and about 80%; or more preferably, between about 81% and about 90%; or even more preferably, between about 91% and about 99%; of amino acids that are identical or functionally equivalent to those of protein(s) encoded by S. aureus cna.

It is also understood that amino acid sequences and nucleic acid sequences may include additional residues, such as additional N- or C-terminal amino acids, or 5' or 3' nucleic acid sequences, and yet still be as set forth herein, so long as the sequence meets the criteria set forth above including the expression of a CBP protein. These additional sequences may, for example, include various transcriptional promoters, enhancers, or terminators, various secretion-directing leader peptides, various amino acid sequences directing posttranslational modifications, amino acids or peptides which may facilitate isolation and purification of CBP(s), and the like. Naturally, alterations and additions to these sequences will be made given consideration of the cell type, organism, or animal that will be chosen for expression of CBP(s).

2.10 Vaccine Formulation

It is expected that to achieve an "immunologically effective formulation" it may be desirable to administer CBPs to the human or animal subject in a pharmaceutically acceptable composition comprising an immunologically effective amount of CBPs mixed with other excipients, carriers, or diluents which may improve or otherwise alter stimulation of B cell and/or T cell responses, or immunologically inert salts, organic acids and bases, carbohydrates, and the like, which promote stability of such mixtures. Immunostimulatory excipients, often referred to as adjuvants, may include salts of aluminum (often referred to as Alums), simple or complex fatty acids and sterol compounds, physiologically acceptable oils, polymeric carbohydrates, chemically or genetically modified protein toxins, and various particulate or emulsified combinations thereof. CBPs or peptides within these mixtures, or each variant if more than one are present, would be expected to comprise about 0.0001 to 1.0 milligrams, or more preferably about 0.001 to 0.1 milligrams, or even more preferably less than 0.1 milligrams per dose.

It is also contemplated that attenuated organisms may be engineered to express recombinant CBP gene products and themselves be delivery vehicles for the invention. Particularly preferred are attenuated bacterial species such as Mycobacterium, and in particular M. bovis, M. smegmatis, or BCG. Alternatively, pox-, polio-, adeno-, or other viruses, and bacteria such as Salmonella, Shigella, Listeria, Streptococcus species may also be used in conjunction with the methods and compositions disclosed herein.

The naked DNA technology, often referred to as genetic immunization, has been shown to be suitable for protection against infectious organisms. Such DNA segments could be used in a variety of forms including naked DNA and plasmid DNA, and may administered to the subject in a variety of ways including parenteral, mucosal, and so-called microprojectile-based "gene-gun" inoculations. The use of cna nucleic acid compositions of the present invention in such immunization techniques is thus proposed to be useful as a vaccination strategy against streptococcal and staphylococcal infection.

It is recognized by those skilled in the art that an optimal dosing schedule of a vaccination regimen may include as many as five to six, but preferably three to five, or even more preferably one to three administrations of the immunizing entity given at intervals of as few as two to four weeks, to as long as five to ten years, or occasionally at even longer intervals.

2.11 Recombinant Host Cells and Vectors

Particular aspects of the invention concern the use of plasmid vectors for the cloning and expression of recombinant peptides, and particular peptide epitopes comprising either native, or site-specifically mutated CBP Col-binding site epitopes. The generation of recombinant vectors, transformation of host cells, and expression of recombinant proteins is well-known to those of skill in the art. Prokaryotic hosts are preferred for expression of the peptide compositions of the present invention. An example of a preferred prokaryotic host is E. coli, and in particular, E. coli strains ATCC 69791, BL21(DE3), JM101, XL1-Blue™, RR1, LE392, B, $\chi^{1776}$ (ATCC 31537), and W3110 (F−, λ−, prototrophic, ATCC 273325). Alternatively, other Enterobacteriaceae species such as Salmonella typhimurium and Serratia marcescens, or even other Gram-negative hosts including various Pseudomonas species may be used in the recombinant expression of the genetic constructs disclosed herein. Alternatively streptococci and staphylococci species may be used to express these constructs, and in particular, S. aureus, S. pyogenes, and S. dysgalactiae.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli may be typically transformed using vectors such as pBR322, or any of its derivatives (Bolivar et al., 1977). pBR322 contains genes for ampicillin and tetracycline resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). The use of recombinant and native microbial promoters is well-known to those of skill in the art, and details concerning their nucleotide sequences and specific methodologies are in the public domain, enabling a skilled worker to construct particular recombinant vectors and expression systems for the purpose of producing compositions of the present invention.

In addition to the preferred embodiment expression in prokaryotes, eukaryotic microbes, such as yeast cultures may also be used in conjunction with the methods disclosed herein. *Saccharomyces cerevisiae*, or common bakers' yeast is the most commonly used among eukaryotic microorganisms, although a number of other species may also be employed for such eukaryotic expression systems. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts in the routine practice of the disclosed methods. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often obtained by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

The origin of replication may be obtained from either by construction of the vector to include an exogenous origin, such as may be derived from SV40 or other viral (e.g, Polyoma, Adeno, VSV, BPV) source, or may be obtained by the host cell chromosomal replication mechanism. If the vector is integrated into the host cell chromosome, the latter is often sufficient.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently-, or colloidal gold-tagged. Means for the labeling and detection of such two-step secondary antibody techniques are well-known to those of skill in the art.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

The file of this patent contains at least one drawing executed in color. Copies of this patent with color drawing (s) will be provided by the Patent and Trademark Office upon request and payment of the necessary fee.

FIG. 1. Folding diagram of CBD(169–318). Arrows represent strands of β-sheets, cylinders represent α-helices. Strands A, B, H, D, and E form β-sheet I. Strands F, G, C, I, and J form β-sheet II.

FIG. 2. Two views 2A & 2B of the Col-binding domain CBD(169–318) represented as a ribbon diagram of secondary structure. Strands A, B, H, D, and E form β-sheet I, strands F, G, C, I, and J form β-sheet II. N denotes amino-terminus, C denotes carboxy-terminus.

FIG. 3A. Connolly's molecular surface of the Col-binding domain viewing the groove on β-sheet I. The texture highlights the surface area of residues within 6 Å from Col probes.

FIG. 3B. A model of bound Col based on the docking search. Same view as in FIG. 3A with the Col triple-helix in gold; only main chains are shown.

FIG. 4. A stereo view of the Col-binding site on the β-sheet I.

4. DESCRIPTION OF ILLUSTRATIVE EMBODIMENTS

Figure 1:
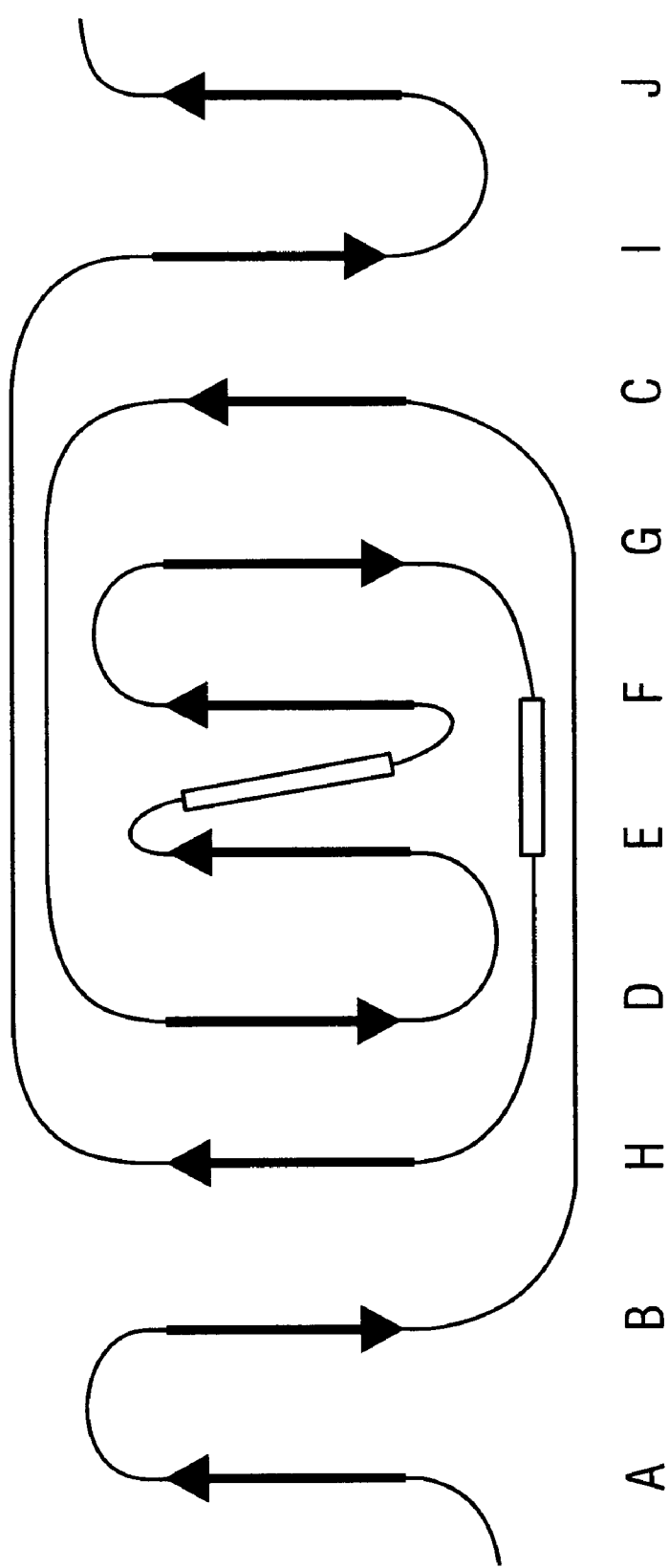

The technology described herein is used to develop methods and compositions that specifically interfere with bacterial adhesion and the subsequent colonization host tissues, thus resulting in the prevention of infection, and the prevention of diseases caused by bacteria which express CBPs on the cell surface. The technology is broadly applicable, has the potential to increase the effectiveness of antibiotic therapy in many situations, and replace antibiotic therapy in a number of other applications. The technology is expected to be especially effective in treatment regimens for staphylococcal and streptococcal infections, and as a cost-effective prophylaxis for prevention of related diseases. The elucidation of the crystal structure of the CBP by the inventors represents a monumental advance in the medical arts, and particularly in the field of infectious disease diagnosis and treatment by providing critical information necessary for identifying compositions which interfere with, or block completely, the binding of Col to CBPs. Such inhibitors are therefore usefuil in the prevention of bacterial adhesion to Col-containing matrices. The inventors have identified the ligand-binding site in the *S. aureus* CBP and a 25-amino-acid peptide has been characterized that directly inhibits the binding of *S. aureus* to $^{125}$I-labeled type II Col. Furthermore, site-directed mutagenesis of the CBP has revealed 2 specific residues critical for ligand binding activity. The invention has obtained for the first time, novel compositions for use in methods to identify inhibitors of the interaction between Col and the CBP both in vitro and in vivo.

4.1 The Role of CBP as a Virulence Factor

To determine the importance of the Col adhesin as a virulence factor in staphylococcal induced septic arthritis, two classes of mutants have been constructed. In the first class of mutants, the isolated Col adhesin gene, cna, was inactivated in a *S. aureus* clinical isolate obtained from a patient with osteomyelitis. In the second type of mutant, the active cna gene was introduced into a *S. aureus* strain that lacked the gene.

The virulence of the two classes of *S. aureus* mutants have been compared with their respective parent strains using a newly developed and characterized murine model of septic arthritis (Bremell et al., 1991). In this model, mice display histopathological signs of arthritis peaking approximately 2–3 weeks post-injection, both with regard to intensity and extension of arthritis, and leveling off thereafter. Clinically estimated signs of arthritis correlate closely to the histopathological evaluation (Bremell et al., 1992). Tail lesions with inflammatory cells invading and destroying the disk and the bone tissue occur within 4 weeks after inoculation in approximately 50% of the mice. Furthermore, the arthritic mice often display a tremendous IL-6 driven polyclonal B-cell activation (Bremell et al., 1992).

The results showed that mice injected intravenously with *S. aureus* strains expressing the Col adhesin were much more likely to develop arthritis compared to mice injected with the *S. aureus* mutant strains. Moreover, serum levels of IgG1 and IL-6 were dramatically elevated in mice injected with the CNA$^+$ clinical isolate compared to mice injected with the CNA$^-$ mutant or saline (Patti et al., 1994). Taken together these data demonstrate that the Col adhesin is an important virulence factor in septic arthritis induced by staphylococci.

4.2 MSCRAMMs

Bacterial adherence to host tissue involves specific microbial surface adhesins of which a subfamily termed MSCRAMMs (Patti et al., 1994; Patti and Hook, 1994) specifically recognize ECM components. Many pathogenic bacteria have been shown to specifically recognize and bind to various components of the ECM in an interaction which appears to represent a host tissue colonization mechanism.

MSCRAMMs (on the bacterial cell surface) and ligands (within the host tissue) are the molecules that interact in a lock and key fashion resulting in the adherence of bacteria to the host. Complete blockage of microbial adhesion is not required to prevent infection. It is only necessary to keep the bacterial inoculum below a critical mass. Several strategies have been developed which are particularly useful in combating bacterial infections, such as infection by streptococcal and staphylococcal species, by preventing bacterial adhesion to Col substrata including the ECM of susceptible host cells. Such strategies are contemplated to be useful in the diagnosis, treatment, and prophylaxis of such infections.

4.3 Extracellular Matrix

The ECM contains numerous glycoproteins and proteoglycans which, through inter- and intramolecular interactions, form insoluble matrices. The ECM has a structural function in the tissues but also affects the cellular physiology of the organism. Perhaps the best characterized biological functions of the ECM are related to its ability to serve as a substrata for the adhesion of host tissue cells. This process involves the integrins, a family of heterodimeric ($\alpha/\beta$) cell surface receptors which recognize specific structures in many of the ECM proteins. It is clear that many bacteria also have taken advantage of the ECM as a substrate for adhesion. Like most eukaryotic tissue cells, many bacteria have developed several parallel adhesion mechanisms and this apparent redundancy may reflect the importance of host tissue adherence for the prosperity of the bacteria.

The adherence of microbes to various cell-surface and ECM components has been widely reported (Abraham et al., 1983; Coburn et al., 1993; Fröman et al., 1984; Isaacs, 1994; Maxe et al., 1986; Van Nhieu and Isber, 1993). The present invention has identified a new bacterial MSCRAMM which promotes bacterial adhesion to Col and other proteoglycans which are structurally similar to Col, which are found in conjunction with ECM components such as Col.

4.4 Collagen

Collagenous proteins are the major constituents of the ECM (Bornstein and Sage, 1980). Most Cols are synthesized intracellularly as precursor molecules and undergo extensive posttranslational processing prior to secretion and incorporation into the ECM or other Col-rich tissues such as cartilage (Ramachandran and Reddi, 1976). To date over 18 different type of Cols have been defined, and they are loosely categorized into five groups (Vanderrest and Garrone, 1991). These groups are:

1) Col types I, II, III, V, and XI which participate in quarter-staggered fibrils;
2) Col types XII, XIV, and IX which are fibril-associated with interrupted triple helices;
3) Col types IV, VIII, and X which form sheets;
4) Col type VI which forms beaded filaments; and
5) Col type VII, which forms anchoring fibrils.

The Col network in skin is composed predominantly of Cols type I and type III. Col can inhibit transforming growth factor beta activity (TGF-$\beta$) (Yamaguchi et al., 1990) and inactivate the complement component C1q (Krumdieck et al., 1992) and has been proposed to act as an anti-inflammatory agent through these interactions.

4.5 CNA-Encoding Nucleic Acid Segments

As used herein, the term "CBP gene" is used to refer to a cna gene or DNA coding region that encodes a protein, polypeptide or peptide that is capable of binding Col, or a related ECM component.

The definition of a "CBP gene", as used herein, is a gene that hybridizes, under relatively stringent hybridization conditions (see, e.g, Maniatis et al., 1982), to DNA sequences presently known to include CBP-encoding gene sequences. It will, of course, be understood that one or more than one genes encoding CBPs or peptides may be used in the methods and compositions of the invention. The nucleic acid compositions and methods disclosed herein may entail the administration of one, two, three, or more, genes or gene segments. The maximum number of genes that may be used is limited only by practical considerations, such as the effort involved in simultaneously preparing a large number of gene constructs or even the possibility of eliciting a significant adverse cytotoxic effect.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on formation of an immune response, or the development of antibodies to gene products encoded by such nucleic acid segments, or in the production of diagnostic and treatment protocols for streptococcal or staphylococcal infection, and in particular, infection with *S. aureus, S. dysgalactiae*, and *S. pyogenes*. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g., proteins or polypeptides or various pharmaceutically active agents. So long as genetic material forms part of the composition, there is virtually no limit to other components which may also be included, given that the additional agents do not cause a significant adverse effect upon contact with the target cells or tissues.

4.6 Therapeutic and Diagnostic Kits Comprising CBP Compositions

Therapeutic kits comprising, in suitable container means, a CBP composition of the present invention in a pharmaceutically acceptable formulation represent another aspect of the invention. The CBP composition may be native CBP, truncated CBP, site-specifically mutated CBP, or CBP-encoded peptide epitopes, or alternatively antibodies which bind native CBP, truncated CBP, site-specifically mutated CBP, or CBP-encoded peptide epitopes. In other embodiments, the CBP composition may be nucleic acid segments encoding native CBP, truncated CBP, site-specifically mutated CBP, or CBP-encoded peptide epitopes. Such nucleic acid segments may be DNA or RNA, and may be either native, recombinant, or mutagenized nucleic acid segments.

The kits may comprise a single container means that contains the CBP composition. The container means may, if desired, contain a pharmaceutically acceptable sterile excipient, having associated with it, the CBP composition and, optionally, a detectable label or imaging agent. The container means may itself be a syringe, pipette, or other such like apparatus, from which the CBP composition may be applied to a tissue site, skin lesion, wound area, or other site of bacterial infection. However, the single container means may contain a dry, or lyophilized, mixture of a CBP composition, which may or may not require pre-wetting before use.

Alternatively, the kits of the invention may comprise distinct container means for each component. In such cases, one container would contain the CBP composition, either as a sterile protein, RNA or DNA solution or in a lyophilized form, and the other container would include the carrier, which may or may not itself be solid or in a sterile solution, or be in a gelatinous, liquid or other form.

The kits may also comprise a second or third container means for containing a sterile, pharmaceutically acceptable buffer, diluent or solvent. Such a solution may be required to formulate the CBP component into a more suitable form for application to the body, e.g., as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the CPB composition within the body of an animal. Such an instrument may be a syringe, pipette, forceps, or any such medically-approved delivery vehicle.

4.7 Affinity Chromotography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of antibodies from solution wherein the matrix contains CBPs or peptide epitopes derived from CBPs, covalently-coupled to a Sepharose CL6B or CL4B. This matrix binds the antibodies of the present invention directly and allows their separation by elution with an appropriate gradient such as salt, GuHCl, pH, or urea. Another preferred embodiment of the present invention is an affinity chromatography method for the purification of CBPs and peptide epitopes from solution. In this case, the matrix may be an antibody specific for CBP or alternatively a composition having affinity for CBPs. The amino acid compositions of the present invention are thus bound directly, and this allows their subsequent purification by elution from the column with a suitable buffer as described above.

4.8 Methods of Nucleic Acid Delivery and DNA Transfection

In certain embodiments, it is contemplated that the nucleic acid segments disclosed herein will be used to transfect appropriate host cells. Technology for introduction of DNA into cells is well-known to those of skill in the art. Four general methods for delivering a nucleic segment into cells have been described:

(1) chemical methods (Graham and VanDerEb, 1973);
(2) physical methods such as microinjection (Capeechi, 1980), electroporation (Wong and Neumann, 1982; Fromm et al., 1985) and the gene gun (Yang et al., 1990);
(3) viral vectors (Clapp, 1993; Eglitis and Anderson, 1988); and
(4) receptor-mediated mechanisms (Curiel et al., 1991; Wagner et al., 1992).

4.9 Liposomes and Nanocapsules

In certain embodiments, the inventors contemplate the use of liposomes and/or nanocapsules for the introduction of particular peptides or nucleic acid segments into host cells. In particular, the malonyltyrosyl and phosphotyrosyl peptides of the present invention may be formulated for delivery in solution with DMSO or encapsulated in liposomes.

Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977; 1988 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987).

Liposomes have been used successfully with a number of cell types that are normally resistant to transfection by other procedures including T cell suspensions, primary hepatocyte cultures and PC 12 cells (Muller et al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989), radiotherapeutic agents (Pikul et al., 1987), enzymes (Imaizumi et al., 1990a; 1990b), viruses (Faller and Baltimore, 1984), transcription factors and allosteric effectors (Nicolau and Gersonde, 1979) into a variety of cultured cell lines and animals. In addition, several successful clinical trails examining the effectiveness of liposome-mediated drug delivery have been completed (Lopez-Berestein et al., 1985a; 1985b; Coune, 1988; Sculier et al., 1988). Furthermore, several studies suggest that the use of liposomes is not associated with autoimmune responses, toxicity or gonadal localization after systemic delivery (Mori and Fukatsu, 1992).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the peptide compositions. They are widely suitable as both water- and lipid-soluble substances can be entrapped, i.e., in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours.

Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell—cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the peptides of the present invention. Nanocapsules can generally entrap compounds in a stable and reproducible way (Henry-Michelland et al., 1987). To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1984; 1988).

4.10 Methods for Preparing Antibody Compositions

In another aspect, the present invention contemplates an antibody that is immunoreactive with a polypeptide of the invention. As stated above, one of the uses for CBPs and CBP-derived epitopic peptides according to the present invention is to generate antibodies. Reference to antibodies throughout the specification includes whole polyclonal and monoclonal antibodies (mAbs), and parts thereof, either alone or conjugated with other moieties. Antibody parts include Fab and F(ab)$_2$ fragments and single chain antibodies. The antibodies may be made in vivo in suitable laboratory animals, by immunizing donors (preferably humans), or in vitro using recombinant DNA techniques. In a preferred embodiment, an antibody is a polyclonal antibody. Means for preparing and characterizing antibodies are well known in the art (See, e.g., Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster, a goat, or a guinea pig. Because of the relatively large blood volume of rabbits, a rabbit is a preferred choice for production of polyclonal antibodies.

Antibodies, both polyclonal and monoclonal, specific for CBP and CBP-derived epitopes may be prepared using conventional immunization techniques, as will be generally known to those of skill in the art. A composition containing antigenic epitopes of particular CBPs can be used to immunize one or more experimental animals, such as a rabbit or mouse, which will then proceed to produce specific antibodies against CBP peptide. Polyclonal antisera may be obtained, after allowing time for antibody generation, simply by bleeding the animal and preparing serum samples from the whole blood.

The amount of immunogen composition used in the production of polyclonal antibodies varies upon the nature of the immunogen, as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate mAbs (below).

One of the important features obtained by the present invention is a polyclonal sera that is relatively homogenous with respect to the specificity of the antibodies therein. Typically, polyclonal antisera is derived from a variety of different "clones," ie., B-cells of different lineage. mAbs, by contrast, are defined as coming from antibody-producing cells with a common B-cell ancestor, hence their "mono" clonality.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As. a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

To obtain mAbs, one would also initially immunize an experimental animal, often preferably a mouse, with a CBP-containing composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fuision protocol with plasmacytoma cells to produce hybridomas secreting mAbs against CBP. Hybridomas which produce mAbs to the selected antigens are identified using standard techniques, such as ELISA and Western blot methods. Hybridoma clones can then be cultured in liquid media and the culture supernatants purified to provide the CBP-specific mAbs.

It is proposed that the mAbs of the present invention will also find useful application in immunochemical procedures, such as ELISA and Western blot methods, as well as other procedures such as imnuunoprecipitation, immunocytological methods, etc. which may utilize antibodies specific to CBPs. In particular, CBP antibodies may be used in immunoabsorbent protocols to purify native or recombinant CBPs or CBP-derived peptide species or synthetic or natural variants thereof.

The antibodies disclosed herein may be employed in antibody cloning protocols to obtain cDNAs or genes encoding CBPs from other species or organisms, or to identify proteins having significant homology to CBP. They may also be used in inhibition studies to analyze the effects of CBP in cells, tissues, or whole animals. Anti-CBP antibodies will also be useful in immunolocalization studies to analyze the distribution of bacteria expressing CBPs during cellular infection, for example, to determine the cellular or tissue-specific distribution of streptococci and staphylococci under different physiological conditions. A particularly useful application of such antibodies is in purifying native or recombinant CBPs, for example, using an antibody affinity column. The operation of all such immunological techniques will be known to those of skill in the art in light of the present disclosure.

4.11 Recombinant Expression of CBP

Recombinant clones expressing the cna nucleic acid segments may be used to prepare purified recombinant CBP (rCBP), purified rCBP-derived peptide antigens as well as mutant or variant recombinant protein species in significant quantities. The selected antigens, and variants thereof, are proposed to have significant utility in diagnosing and treating infections caused by S. aureus, S. pyogenes and S. dysgalactiae. For example, it is proposed that rCBPs, peptide variants thereof, and/or antibodies against such rCBPs may also be used in immunoassays to detect S. aureus, S. pyogenes and S. dysgalactiae cells or as vaccines or immunotherapeutics to treat S. aureus, S. pyogenes and S. dysgalactiae infections, and to prevent bacterial adhesion to ECM components such as Col in the same manner as native CBP compositions.

Additionally, by application of techniques such as DNA mutagenesis, the present invention allows the ready preparation of so-called "second generation" molecules having modified or simplified protein structures. Second generation proteins will typically share one or more properties in common with the full-length antigen, such as a particular antigenic/immunogenic epitopic core sequence. Epitopic sequences can be obtained on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of blocking antibodies which prevent bacterial adhesion to Col, as outlined herein.

4.12 Antibody Compositions and Formulations Thereof

Means for preparing and characterizing antibodies are well known in the art (See. e.g., Harlow and Lane (1988);

incorporated herein by reference). The methods for generating mAbs generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976) and those using polyethylene glycol (PEG), such as 37% (v/v) PEG, by Gefter et al. (1977) The use of electrically induced fusion methods is also appropriate (Goding, 1986).

Fusion procedures usually produce viable hybrids at low frequencies, about $1 \times 10^{-6}$ to about $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific mAb produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mnAbs produced by either means may be further purified, if desired, using filtration, centrifugation and various chromatographic methods such as HPLC or affinity chromatography.

4.13 Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of CBP-derived proteins and peptides is not limited to such assays, and that other useful embodiments include RIAs and other non-enzyme linked antibody binding assays and procedures.

In preferred ELISA assays, proteins or peptides incorporating CBP, rCBP, or CBP-derived protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween™. These added agents also tend to assist in the reduction of nonspecific background. The layered antisera is then allowed to incubate for, e.g., from 2 to 4 h, at temperatures preferably on the order of about 25° to about 27° C. Following incubation, the antisera-contacted surface is washed so as to remove non-immunocomplexed material. A preferred washing procedure includes washing with a solution such as PBS/Tween™, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugated anti-human IgG for a period of time and under conditions that favor the development of immunocomplex formation (e.g., incubation for 2 h at room temperature in a PBS-containing solution such as PBS-Tween™).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

ELISAs may be used in conjunction with the invention. In one such ELISA assay, proteins or peptides incorporating antigenic sequences of the present invention are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

4.14 Immunoprecipitation

The anti-CBP antibodies of the present invention are particularly useful for the isolation of CBP antigens by immunoprecipitation. Immunoprecipitation involves the separation of the target antigen component from a complex mixture, and is used to discriminate or isolate min amounts of protein. For the isolation of cell-surface localized proteins such as CBP, peptides must be solubilized from the bacterial cell wall by treatment with enzymes such as lysozyme, lysostaphin or mutanolysin, or alternatively, into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g., enzyme-substrate pairs.

In a related embodiment, antibodies of the present invention are useful for promoting the binding of Col to cna gene products. Such binding is readily measured by monitoring ligand binding using well-known procedures. Detection of the binding may be accomplished by using radioactively labeled antibodies or alternatively, radioactively-labeled Col. Alternatively, assays employing biotin-labeled antibodies are also well-known in the art as described (Bayer and Wilchek, 1980).

4.15 Western Blots

The compositions of the present invention will find great use in immunoblot or western blot analysis. The anti-CBP antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal. Immunologically-based detection methods in conjunction with Western blotting (including enzymatically-, radiolabel-, or fluorescently-tagged secondary antibodies against the toxin moiety) are considered to be of particular use in this regard.

4.16 Vaccines

The present invention contemplates vaccines for use in both active and passive immunization embodiments. Immunogenic compositions proposed to be suitable for use as a vaccine may be prepared most readily directly from the novel immunogenic proteins and/or peptide epitopes described herein. Preferably the antigenic material is extensively dialyzed to remove undesired small molecular weight molecules and/or lyophilized for more ready formulation into a desired vehicle.

The preparation of vaccines that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables, either as liquid solutions or suspensions, solid forms suitable for solution in, or suspension in, liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

A composition comprising CBP or CBP-derived proteins and/or native or modified epitopic peptides therefrom may also be the basis for human vaccines. The preparation of such compositions that are essentially free from endotoxin can be achieved by following the published methodology, for example, U.S. Pat. No. 4,271,147 (incorporated herein by reference) discloses methods for the preparation of *Neisseria meningitidis* membrane proteins for use in vaccines.

CBP and CBP-derived epitope-based vaccines may be conventionally administered parenterally, by injection, for example, either subcutaneously or intramuscularly. Additional formulations that are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered will be readily determinable by the skilled practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol®) used as 0.25% solution, aggregation of the protein in the vaccine by heat treatment with temperatures ranging between about 70° and about 101° C. for 30 sec to 2 min periods respectively. Aggregation by reactivating with pepsin treated F(ab) antibodies to albumin, mixture with bacterial cells such as *C. parvum* or endotoxins or lipopolysaccharide components of gram-negative bacteria, emulsion in physiologically acceptable oil vehicles such as mannide monooleate (Aracel-A™) or emulsion with 20% solution of a perfluorocarbon (Fluosol-DA™) used as a block substitute may also be employed.

In many instances, it will be desirable to have multiple administrations of the vaccine, usually not exceeding 6 vaccinations, more usually not exceeding 4 vaccinations and preferably one or more, usually at least about 3 vaccinations. The vaccinations will normally be at from 2 to 12 week intervals, more usually from 3 to 5 week intervals. Periodic boosters at intervals of 1–5 years, usually 3 years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, (each specifically incorporated herein by reference, as illustrative of these types of assays).

Of course, in light of the new technology on DNA vaccination, it will be understood that virtually all such vaccination regimens will be appropriate for use with DNA vectors and constructs, as described (Ulmer et al., 1993; Tang et al., 1992; Cox et al., 1993; Fynan et al., 1993; Wang et al., 1993; Whitton et al., 1993, each incorporated herein by reference). In addition to parenteral routes of DNA inoculation, including intramuscular and intravenous injections, mucosal vaccination is also contemplated, as may be achieved by administering drops of DNA compositions to the nares or trachea. It is particularly contemplated that a gene-gun could be used to deliver an effectively immunizing amount of DNA to the epidermis (Fynan et al., 1993).

The present invention contemplates vaccines for use in both active and passive immunization embodiments. Immunogenic compositions, proposed to be suitable for use as a vaccine, may be prepared most readily directly from immunogenic peptides prepared in a manner disclosed herein. Preferably the antigenic material is extensively dialyzed to remove undesired small molecular weight molecules and/or lyophilized for more ready formulation into a desired vehicle. The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

4.17 Pharmaceutical Formulation

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form.

Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.18 Screening Assays

Host cells that have been transformed could be used in the screening of natural and artificially derived compounds or mixtures to select those that are capable of complexing with the CBP and CBP-derived proteins of the present invention. This could be useful in the search for compounds that inhibit or otherwise disrupt, or even enhance the ability of the microorganism to bind Col. It is contemplated that effective pharmaceutical agents could be developed by identifying compounds that complex with the particular CBP epitopes, including, for example, compounds isolated from natural sources, such as plant, animal and marine sources, and various synthetic compounds. Natural or man-made compounds that may be tested in this manner could also include various minerals and proteins, peptides or antibodies.

4.19 Epitopic Core Sequences

The present invention is also directed to protein or peptide compositions, free from total cells and other peptides, which comprise a purified protein or peptide which incorporates an epitope that is immunologically cross-reactive with one or more of the antibodies of the present invention.

As used herein, the term "incorporating an epitope(s) that is immunologically cross-reactive with one or more anti-CBP antibodies" is intended to refer to a peptide or protein antigen which includes a primary, secondary or tertiary structure similar to an epitope located within a CBP polypeptide. The level of similarity will generally be to such a degree that monoclonal or polyclonal antibodies directed against the CBP polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of CBP epitopes such as those derived from cna or cna-like gene products and/or their fumctional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 5 to about 25 amino acids in length, and more preferably about 8 to about 20 amino acids in length. It is proposed that shorter antigenic peptide sequences will provide advantages in certain circumstances, for example, in the preparation of vaccines or in immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to CBP and CBP-related sequences, or other domains which bind Col or related proteoglycans. It is proposed that these regions represent those which are most likely to promote T-cell or B-cell stimulation in an animal, and, hence, elicit specific antibody production in such an animal.

An epitopic core sequence, as used herein, is a relatively short stretch of amino acids that is "complementary" to, and therefore will bind, antigen binding sites on CBP epitope-specific antibodies. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directee antisera.

In general, the size of the polypeptide antigen is not believed to be particularly crucial, so long as it is at least large enough to carry the identified core sequence or sequences. The smallest useful core sequence expected by the present disclosure would generally be on the order of about 5 amino acids in length, with sequences on the order of 8 or 25 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic CBP peptides and peptide analogs in accordance with the present disclosure.

The peptides obtained from by this invention are ideal targets for use as vaccines or immunoreagents for the treatment of various staphylococcal- or streptococcal-related diseases, and in particular, those caused by species which contain CBP and CBP-encoding genes, and hence those which express either cna or cna-like gene product(s) on the cell surface and in turn interact with ECM components such as Col to promote bacterial adhesion to host cells. In this regard, particular advantages may be realized through the preparation of synthetic peptides that include epitopic/immunogenic core sequences. These epitopic core sequences may be identified as hydrophilic and/or mobile regions of the polypeptides or those that include a T-cell motif. It is known in the art that such regions represent those that are most likely to promote B cell or T cell stimulation, and, hence, elicit specific antibody production.

In the case of preventing bacterial adhesion, the preparation of epitopes which produce antibodies which inhibit the interaction of a Col-specific gene product and Col or proteoglycans which are structurally similar to Col are particularly desirable.

To confirm that a protein or peptide is immunologically cross-reactive with, or a biological functional equivalent of, one or more epitopes of the disclosed peptides is also a straightforward matter. This can be readily determined using specific assays, e.g., of a single proposed epitopic sequence, or using more general screens, e.g., of a pool of randomly generated synthetic peptides or protein fragments. The screening assays may be employed to identify either equivalent antigens or cross-reactive antibodies. In any event, the principle is the same, i.e., based upon competition for binding sites between antibodies and antigens.

Suitable competition assays that may be employed include protocols based upon immunohistochemical assays, ELISAs, RIAs, Western or dot blotting and the like. In any of the competitive assays, one of the binding components, generally the known element, such as the CBP-derived peptide, or a known antibody, will be labeled with a detectable label and the test components, that generally remain unlabeled, will be tested for their ability to reduce the amount of label that is bound to the corresponding reactive antibody or antigen.

As an exemplary embodiment, to conduct a competition study between a CBP and any test antigen, one would first label CBP with a detectable label, such as, e.g., biotin or an enzymatic, radioactive or fluorogenic label, to enable subsequent identification. One would then incubate the labeled antigen with the other, test, antigen to be examined at various ratios (e.g., 1:1, 1:10 and 1:100) and, after mixing, one would then add the mixture to an antibody of the present invention. Preferably, the known antibody would be immobilized, e.g., by attaching to an ELISA plate. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label. An antigen that binds to the same antibody as CBP, for example, will be able to effectively compete for binding to and thus will significantly reduce CBP binding, as evidenced by a reduction in the amount of label detected.

The reactivity of the labeled antigen, e.g., a CBP composition, in the absence of any test antigen would be the control high value. The control low value would be obtained by incubating the labeled antigen with an excess of unlabeled CBP antigen, when competition would occur and reduce binding. A significant reduction in labeled antigen reactivity in the presence of a test antigen is indicative of a test antigen that is "cross-reactive", i.e., that has binding affinity for the same antibody. "A significant reduction", in terms of the present application, may be defined as a reproducible (i.e., consistently observed) reduction in binding.

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Syntheses of epitopic sequences, or peptides which include an antigenic epitope within their sequence, are readily achieved using conventional synthetic techniques such as the solid phase method (e.g., through the use of a commercially-available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.20 Site-Specific Mutagensis

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer hearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is obtained from as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylarnine, to obtain sequence variants. Specific details regarding these methods and protocols are found in the teachings of Maloy, 1990; Maloy et al., 1994; Segal, 1976; Prokop and Bajpai, 1991; Kuby, 1994; and Maniatis et al., 1982, each incorporated herein by reference, for that purpose.

The PCRT™-based strand overlap extension (SOE) (Ho et al., 1989) for site-directed mutagenesis is particularly preferred for site-directed mutagenesis of the nucleic acid compositions of the present invention. The techniques of PCRTM are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into E. coli JM101, XLI-Blue™ (Stratagene, La Jolla, Calif.), JM105, or TG1 (Carter et al., 1985) cells. Clones are isolated and the mutations are confirmed by sequencing of the isolated plasmids.

4.21 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |

TABLE 1-continued

| Amino Acids | | | Codons | |
|---|---|---|---|---|
| Tryptophan | Trp | W | UGG | |
| Tyrosine | Tyr | Y | UAC | UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.22 Bacterial MSCRAMMS (ADHESINS) as Vaccine Candidates

Historically, studies on bacterial adherence have focused primarily on Gram-negative bacteria, which express a wide variety of fimbrial adhesive proteins (designated adhesins) on their cell surface (Falkow et al. 1992). These adhesins recognize specific glycoconjugates exposed on the surface of host cells (particularly epithelial layers). Employing the lectin-like structures in attachment allows the microorganism to efficiently colonize the epithelial surfaces, this provides the bacteria an excellent location for replication and also the opportunity to disseminate to neighboring host tissues. In many cases it has been demonstrated that immunization with pilus adhesins can elicit protection against microbial challenge, such as in *Hemophilus influenza* induced otitis media in a chinchilla model (Sirakova et al. 1994), *Moraxella bovis* in experimentally induced infectious bovine keratoconjunctivitis (Lepper et al. 1995), and *E. coli* induced diarrhea in rabbits (McQueen et al. 1993). In most cases, immunization with adhesins leads to the production of immune antibodies that prevent infection by inhibiting bacterial attachment and colonization, as well as enhancing bacterial opsonophagocytosis and antibody-dependent complement-mediated killing.

The use of molecules that mediate the adhesion of pathogenic microbes to host tissue components as vaccine components is emerging as a critical step in the development of future vaccines. Because bacterial adherence is the critical first step in the development of most infections, it is an attractive target for the development of novel vaccines. An increased understanding of the interactions between MSCRAMMs and host tissue components at the molecular level coupled with new techniques in recombinant DNA technology have laid the foundation for a new generation of subunit vaccines. Entire or specific domains of MSCRAMMs, either in their native or site-specifically altered forms, can now be produced. Moreover, the ability to mix and match MSCRAMMs from different microorganisms creates the possibility of designing a single vaccine that will protect against multiple bacteria.

The recent clinical trials with a new subunit vaccine against whooping cough, consisting of the purified *Bordatella pertussis* MSCRAMMs filamentous hemagglutinin and pertactin, in addition to an inactivated pertussis toxin, are a prime example of the success of this type of approach. Several versions of the new acellular vaccine were shown to be safe and more efficacious than the old vaccine that contained whole bacterial cells (Greco et al. 1996; Gustaffson et al. 1996).

4.23 Current *S. aureus* Vaccine Components

The development of penicillin to combat *S. aureus* was a major advance in infection control and treatment.

Unfortunately, penicillin-resistant organisms quickly emerged and the need for new antibiotics was paramount. With the introduction of every new antibiotic, S. aureus has been able to counter with beta-lactamases, altered penicillin-binding proteins, and mutated cell membrane proteins allowing the bacterium to persist. Consequently, methicillin-resistant S. aureus (MRSA) and multidrug resistant organisms have emerged and established major footholds in hospitals and nursing homes around the world.

Immunity to S. aureus infections remains poorly understood. Typically, healthy humans and animals exhibit a high degree of innate resistance to S. aureus infections. Protection is attributed to intact epithelial and mucosal barriers and normal cellular and humoral responses. Titers of antibodies to S. aureus components are elevated after severe infections (Ryding et al. 1995), however to date there is no serological evidence of a correlation between antibody titers and human immunity.

Over the past several decades live, heat-killed, and formalin fixed preparations of S. aureus cells have been tested as vaccines to prevent staphylococcal infections. A multi-center clinical trial was designed to study the effects of a commercial vaccine, consisting of a staphylococcus toxoid and whole killed staphylococci, on the incidence of peritonitis, exit site infection, and S. aureus nasal carriage among continuous peritoneal dialysis patients (Poole-Warren et al. 1991). Although immunization with the vaccine elicited an increase in the level of specific antibodies to S. aureus, the incidence of peritonitis was unaffected. Similarly, immunization of rabbits with whole cells of S. aureus could not prevent or modify any stage in the development of experimental endocarditis, reduce the incidence of renal abscess, or lower the bacterial load in infected kidneys (Greenberg et al. 1987).

Currently there is no FDA approved vaccine for the prevention of S. aureus infections (Foster 1991). However, a S. aureus vaccine (StaphVAX), based on the capsular polysaccharide, is currently being developed by NABI (North American Biologicals Inc.). This vaccine consists of type 5 or type 8 capsular polysaccharides conjugated to Pseudomonas aeruginosa exotoxin A (rEPA). The vaccine is designed to induce type-specific opsonic antibodies and enhance opsonophagocytosis of (Karakawa et al. 1988). Using a refined lethal challenge mouse model (Fattom et al. 1996) it has been shown that intraperitoneal infusion of type 5 specific IgG reduces the mortality of mice inoculated intraperitoneally with S. aureus. The type 5 capsular polysaccharide-rEPA vaccine has also been used to vaccinate seventeen patients with end-stage renal disease (Welch et al. 1996). Geometric mean (GM) IgG antibody levels to the type 5 conjugate increased between 13 and 17-fold after the first immunization, however no additional increases could be detected after additional injections. Interestingly, the GM IgM levels of the vaccinated patients were significantly lower than control individuals. Supported by the animal studies, the vaccine has recently completed a Phase II trial in continuous ambulatory peritoneal dialysis patients. The clinical trial showed the vaccine to be safe but ineffective in preventing staphylococcal infections (NABI SEC FORM 10-K405, Dec. 31, 1995). Two possible explanations for the inability of StaphVAX to prevent infections related to peritoneal dialysis in vaccinated patients are that the immunogenicity of the vaccine was too low due to suboptimal vaccine dosing or that antibodies in the bloodstream are unable to affect infection in certain anatomic areas, such as the peritoneum.

4.24 Use of the S. aureus CBP as a Vaccine Component

4.24.1 Sepsis

Gram-positive bacteria related sepsis is on the increase. In fact between one-third and one-half of all cases of sepsis are caused by gram-positive bacteria, particularly S. aureus and S. epidermidis. In the United States, it can be estimated that over 200,000 patients will develop gram-positive related sepsis this year. Using a mouse model (Bremell et al. 1991) the inventors have clearly demonstrated that active immunization with M55 domain (SEQ ID NO:6) of the Col-binding MSCRAMM can protect mice against sepsis induced death. Mice were immunized subcutaneously with either M55 or a control antigen (bovine serum albumin) and then challenged intravenously with S. aureus. Eighty-three percent (35/42) of the mice immunized with M55 survived compared to only 27% of the BSA immunized mice (12/45). This a compilation of 3 separate studies.

4.25 Production of a Prototype Multivalent MSCRAMM-Based Vaccine

A series of recombinant proteins, representing domains from the Col, Fn, and Fbg-binding MSCRAMMs, were overexpressed in E. coli and affinity purified by metal chelating chromatography as previously described (Joh et al., 1994; McDevitt et al., 1994; Patti et al., 1995): (1) amino acids contained in the recombinant CBP M17; SEQ ID NO:2); (2) amino acids contained in the recombinant Fib-binding MSCRAMM (pCF33), and (3) amino acids contained in the recombinant fibronectin-binding MSCRAMM (pQD).

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1—Critical Residues in the Ligand Binding Site of the S. aureus CBP A discrete Col-binding site has been identified within the S. aureus Col adhesin that is located in a region between amino acids $Asp^{209}$ and $Tyr^{233}$. Polyclonal antibodies raised against a recombinant form of the Col adhesin inhibited the binding of type II Col to S. aureus. When overlapping synthetic peptides mimicking segments of the adhesin fragment were tested for their ability to neutralize the inhibitory activity of the antibody only one peptide, CBD4 was found to be active. CBD4 bound directly to Col and at high concentrations inhibited the binding of Col to S. aureus. A synthetic peptide derivative of CBD4 lacking 2 carboxyl-terminal residues ($Asn^{232}$, $Tyr^{233}$) had minimal inhibitory activity. The importance of these residues for Col binding was confirmed by biospecific interaction analysis. Mutant adhesin proteins $N^{232} \rightarrow A$ and $Y^{233} \rightarrow A$ exhibited dramatic changes in Col binding activity. The dominant dissociation rate for the binding of mutant adhesin protein $N^{232} \rightarrow A$ to immobilized Col II decreased almost 10-fold, while the $Y^{233} \rightarrow A$ and the double mutant exhibited even more significant decreases in affinity and apparent binding ratio when compared to the wild type protein.

5.1.1 Polyclonal IgG Against MSCRAMM Fragments Inhibit Col Binding to S. aureus

Studies were conducted to identify the ligand-binding site of the S. aureus CBP by examining the binding activity of recombinant MSCRAMM fragments of progressively decreasing size. Truncations beyond a 168-amino-acid long segment, CBD(151–318), resulted in loss of Col binding activity but also affected the folding of the resulting proteins as indicated by CD spectroscopy. Thus it is possible that the ligand-binding site is contained within a short segment of CBD(151–318), but due to the improper folding of the protein the Col-binding site is not in an active form. To explore this possibility, an antibody inhibition-neutralization approach was developed. A similar strategy was used successfully to monitor the purification of the native CBP from S. aureus cells (Switalski et al., 1989). To generate an inhibiting antibody, CBD(151–297), a recombinant version of the largest segment that did not bind Col and exhibited an altered conformation, was used as an antigen. In this way, generating inhibiting antibodies which recognize conformational dependent epitopes would be minimized. An inhibiting monoclonal antibody generated against a biologically active CBP recognized a conformational dependent epitope and was of limited use in identifying the binding site.

Rabbits were immunized with CBD(157–297) as described. Sera were also collected prior to immunization and tested for reactivity to CBD(151–297). The reactivity of the antiserum with different segments of CBD(151–297) was tested in an ELISA using a series of eight 25-amino-acid long synthetic peptides with partially overlapping sequences as targets. Purified IgG reacted strongly with peptides 2, 3, 5, 6, and 7 and weakly with peptides 1, 4, and 8. When preimmune IgG was tested with the CBD peptides, little reaction could be detected. The relative immunological reactivity of the different peptides correlated closely with their antigenic index using the algorithm of Jameson and Wolf (1988).

Purified αCBD(151–297) IgG inhibited the binding of S. aureus to $^{125}$I-labeled Col in a dose-dependent manner. The amount of $^{125}$I-Col bound by $10^8$ bacterial cells was reduced over 50% by 5 μg and essentially completely inhibited by 10 μg of the purified immune IgG. Conversely, antibodies purified from preimmune sera did not possess significant inhibitory activity. These results suggest that the αCBD (151–297) antibodies recognize epitopes at or close to the active site of the MSCRAMM, thereby inhibiting or sterically interfering with Col binding.

5.1.2 Synthetic Peptides Neutralize Inhibitory Activity of αCBD(151–297) IgG

The different synthetic CBD peptides described above and shown to react with the αCBD(151–297) IgG were assayed for their potential to neutralize the inhibitory activity of the antibody. The αCBD(151–297) IgG (12 μg) was preincubated with a single dose (100 μg) of each peptide in step one. The S. aureus cells were then added and the preincubation continued. Finally, the $^{125}$I-labeled type II Col was added. Peptide CBD4 neutralized 68% of αCBD(151–297) IgG inhibitory activity, while the other peptides tested had little or no effect. These results suggested that only antibodies recognizing epitopes present in CBD4 were able to inhibit Col binding to bacteria. Although other peptide sequences were more immunogenic than CBD4, the antibodies recognizing the corresponding epitopes were not inhibitory. These data suggest that the ligand-binding site of the MSCRAMM is located close to or within the sequence covered by peptide CBD4.

To further investigate the interaction between peptide CBD4 and αCBD(151–297) IgG and its affect on Col binding, a fixed concentration of the antibody was incubated with an increasing amount of peptide CBD4. To make the assay more sensitive, an αCBD(151–297) IgG concentration (12 μg/ml) was chosen which resulted in a 50% reduction in Col binding to $10^8$ S. aureus cells. Thus, a relatively small reduction in inhibition could be easily detected. At low concentrations, the peptide appears to neutralize the inhibitory activity, and in this study 100 μg of peptide CBD4 restored the level of Col binding to S. aureus observed in absence of αCBD(151–297) IgG. Somewhat surprisingly, addition of more peptide CBD4 resulted in a dose-dependent decrease in Col binding to S. aureus.

5.1.3 Peptide CBD4 Directly Inhibits Col Binding to S. aureus

To assess the role of amino acids 209–233 in Col binding, peptide CBD4 was tested for the ability to directly inhibit the binding of $^{125}$I-Col to S. aureus. Peptide CBD7 which reacted strongly with αCBD(151–297) IgG in the ELISA assay was also tested. When increasing amounts of peptide CBD4 were incubated with $^{125}$I-Col prior to the addition of S. aureus, binding to Col was inhibited in a dose-dependent manner. Five μM CBD4 inhibited binding by over 50%. Peptide CBD7 had no inhibitory effect when it was preincubated with $^{125}$I-Col. These data suggest that peptide CBD4 can bind soluble $^{125}$I-Col and that CBD4 contains the residues that represent a Col-binding site within the MSCRAMM protein.

5.1.4 Critical CBD4 Residues Required for Col Binding Activity

To identify residues within CBD4 necessary for Col binding synthesized several smaller overlapping peptides were synthesized. A series of peptides that contained a 2 amino-terminal residues and one peptide that contained a 2 amino acid deletion at the carboxyl terminus were made. The peptides (10 μM) were assayed for their ability to inhibit the binding of $^{125}$I-labeled Col to S. aureus. Peptide CBD4 inhibited Col binding by 76%, whereas all peptides containing amino-terminal truncations had little activity at the concentration tested. These data indicate that when as few as 5 residues are removed from the active site peptide, the ability to bind Col is lost. Moreover, deletion of only the 2 carboxyl-terminal amino acids causes a complete loss of biological activity. This suggests that amino acids at the C terminus of CBD4, Asn$^{232}$ and Tyr$^{233}$ or both are integral member(s) of the active site of CBP.

5.1.5 Col Binding Activity of Defined MSCRAMM Mutants

The importance of amino acid residues Asn$^{232}$ and Tyr$^{233}$ in the MSCRAMM for Col binding was examined by creating specific mutants of CBD (30–529) and characterizing the interactions of these mutants with immobilized type II Col using the BIAcore. In the mutations made, the identified amino acid residues were replaced individually, (N$^{232}$→A, Y$^{233}$→A) or as a pair, (N$^{232}$→A:Y$^{233}$→A) with alanine, a residue that is not expected to interfere with the existing secondary structure. The corresponding base changes were made using overlap extension PCR™ as described and the sequence changes confirmed experimentally. The recombinant proteins containing the mutations were purified to homogeneity by metal ion chelating chromatography. Structural analyses of the isolated proteins by near- and far-UV CD spectroscopy suggested that no significant changes in secondary or tertiary structure had occurred as a result of the mutations.

Under the conditions described CBD (30–529) exhibits complex multiphasic interactions when analyzed using the BIAcore. True equilibrium was not obtained during the injection time period due to the slow dissociation rate ($k_{off}$). The association phase exhibits multiphasic binding with an interaction characterized by a fast $k_{off}$ apparent at the start of the injection followed by a second phase characterized by a much slower $k_{off}$. The dissociation phase gives information about the $k_{off}$, and this rate is independent of the number of binding sites, analyte concentration, and flow rate. Analysis of these data indicates at least a three-component dissociation with the two fastest rates greater than $10^{-2}S^{-1}$ and the slowest $k_{off}$ at $5\times10^{-4}S^{-1}$. The association phase contains the information to determine the association rate $k_{off}$ the interaction, but it is also influenced by the dissociation rate, the number of binding sites for each interaction, and the concentration of the analyte. Because of the complexity of this interaction and the absence of measurable equilibrium data, it was not possible to determine the binding constant ($K_D$), apparent binding ratio ($BR_{app}$), and $k_{on}$.

In a comparison of the three mutant proteins with wild type CBD(30–529), it is readily apparent that each of the introduced mutations affected the Col binding properties of the generated proteins. While the shape of the binding sensorgram remains essentially the same for mutant $N^{232}\rightarrow A$, analysis of the dissociation phase indicates that the slowest dissociation rate has increased almost 10-fold. Although a disassociation constant ($K_D$) cannot be determined, it appears that the affinity of this mutant for type II Col has also been influenced by this mutation. Both the $Y^{233}\rightarrow A$ and the double mutant bind immobilized type II. Analysis of the data obtained with the double mutant produces a monophasic binding constant when evaluated by either Scatchard analysis or Equation 1. Additionally, the $BR_{app}$ has decreased to approximately two to three high affinity sites.

From the Biosensor results it is apparent that residues $Asn^{232}$ and $Tyr^{233}$ are important for both the affinity and the specificity of CBD(30–529)'s binding to type II Col. There does not, however, seem to be an additive effect of the double mutation when compared to the single mutations.

5.2 Example 2—Structure of the Col-Binding Domain from the *S. aureus* CBP

The structural basis for host tissue targeting by *S. aureus* presented here reveals that the Col-binding domain CBD (151–318) is well-designed to interact with triple-helical Col structures. The binding interface of the domain is built along a groove on a concave β-sheet and has considerable geometrical and chemical complementarity to the Col helical segment containing four repeats of Gly-Pro-Hyp or Gly-Pro-Pro per chain. Mutational analysis has confirmed the putative Col binding site, and suggests that the simple docking model may have more general significance. In this model, the Col triple helix itself is a major recognition element for the bacterial adhesin containing complementary binding site. This provides a structural explanation for the earlier observations of the MSCRAMM's specificity for triple-helical structures (Speziale et al., 1986). In addition, the suggested binding site on the adhesin appears to be versatile, in that it allows appropriate diversity, but restricted by structural complementarity. The generality of this model must await structural analysis of other proteins that bind to the Col triple-helix.

5.2.1 Methods 5.2.1.1 Crystallization and Data Collection

The recombinant polypeptide CBD(151–318) was crystallized by the hanging drop vapor diffusion method using PEG 4000 as precipitant, 50 mM HEPES buffer between pH 6.2 and 6.9, and the detergent n-octyl-β-D-glucopyranoside. The crystals belong to trigonal space group $P3_221$ or the enantiomorph $P3_121$. The unit cell parameters are $a=74.0$ Å, $b=74.0$ Å, $c=56.7$ Å, $\alpha=90°$, $\beta=90°$, $\gamma=120°$. There is one molecule per asymmetric unit with estimated solvent content of 44%. Diffraction data were collected at room temperature on a Siemens Histar area detector and processed with X-GEN from Molecular Simulations Inc. A number of potential heavy atom derivative data sets were collected, however, only $HgCl_2$ and $K_2PtCl_4$ derivatives were useable for MIR phasing.

5.2.1.2 Structure Solution and Refinement

The phasing solution with the right handedness was consistent with the space group $P3_221$ and provided an interpretable map. The solvent flattened MIR map at 3 Å resolution revealed major features of the structure and was suitable for both chain tracing and sequence alignment. From the deduced sequence of 168 amino acids, 150 residues between 169–318 were aligned to the map. The initial model was refined at 2.4 Å resolution with X-PLOR (Brunger, 1992) using conjugate gradient minimization, MIR phases constraints, and $F>2\ \sigma_F$. At this stage, the R-factor and R-free were 34.3% and 41.4%, respectively. The model was further improved by several cycles of simulated annealing refinement and manual model building. Before adding water molecules, isotropic temperature factors of individual non-hydrogen atoms were refined and the R-factor and R-free dropped to 25.3% and 31.3%, respectively, for the resolution shell 10.0–2.0 Å. Water molecules were fitted to FO-FC maps at the 3 σ level. Several final rounds of conjugate gradient minimization and manual model building resulted in the R-factor of 20.0% and the R-free of 24.9%. Atomic coordinates of the crystal structure will be deposited in Protein Data Bank.

5.2.1.3 Docking Search

Briefly, dot surfaces (Connolly, 1993) with normal vectors are calculated for the target and the probe, respectively, and divided in surface cubes and interior cubes. The nearest atom to each dot determines the chemical propensity represented by a simple six-color code. Rotation space of the 'cubed' probe is sampled and for each rotation step all integer translations of the probe cubes to the stationary target cubes are calculated. Each translation of the probe is scored according to the match of normal vectors, compatibility of color codes, and overlapping interior cubes. Clustered solutions with the best scores are averaged and the corresponding rotations and translations applied to atomic coordinates of the probe.

5.2.1.4 CD Spectra

All CD spectra were collected using a Jasco J720 spectropolarimeter calibrated with a 0.1% (wt./vol.) 10-camphorsulfonic acid-d solution. Spectra were measured at 25° C. and 5 scans were averaged. A 0.05 cm path length cell was used for near-UV (250–320 nm) CD and a 1 cm path length cell was used for far-UV (190–250 nm) CD.

5.2.2 Structure Determination

The crystal structure of CBD(151–318) was determined using conventional heavy atom/multiple isomorphous replacement (MIR) methods and was refined to a crystallographic R-factor of 20% ($R_{free}=24.9\%$) using diffraction data between 10.0 and 2.0 Å resolution (Table 2). The refined model includes 150 amino acids between residues 169–318 and 74 water molecules. The root mean square deviation (RMS) from ideal bond lengths is 0.012 Å, and RMS deviation from ideal angles is 1.625°. The model scores high in PROCHECK (Laskowski et al., 1993) analysis and a Ramachandran plot of φ,ψ conformation angles has no outliers. The electron density was of good quality throughout the structure and there were eight disordered exterior side chains in the final model. No electron density was observed for N-terminal residues 151–168.

5.2.3 Structure Description

Figure 2A:
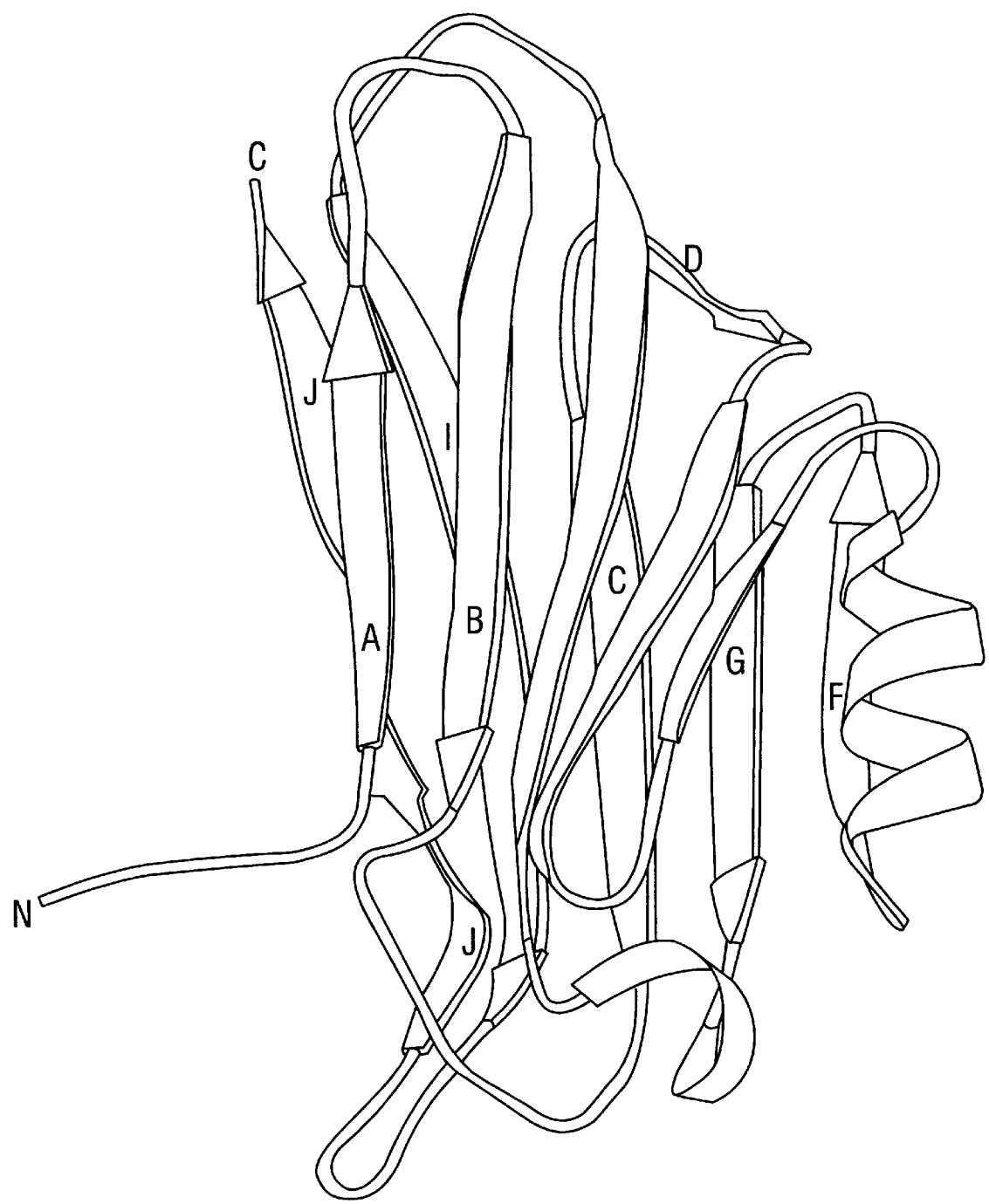
Figure 2B:
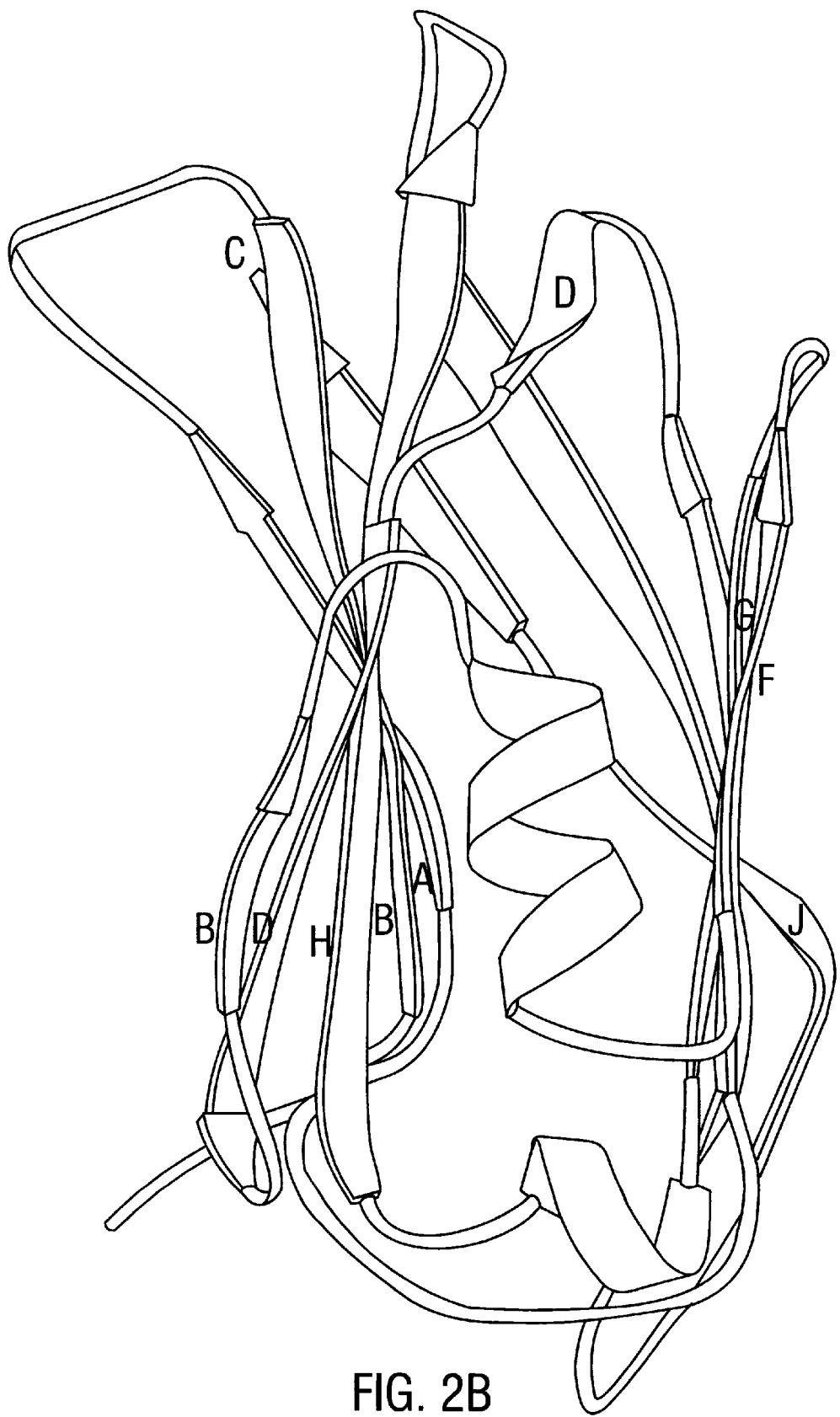

The molecular structure of the recombinant Col-binding domain is very compact with approximate dimensions 55×35×25 Å. The polypeptide chain of CBD(169–318) is folded to a 'jelly-roll' topological pattern (FIG. 1) (Richardson, 1981). The secondary structure of the domain consists of 53% β-sheet, 39% coil, and 8% helix. There are no disulfide bridges or free cysteines. The entire domain is essentially composed of two β-sheets, parallel to each other, and two small α-helices (FIG. 2). β-sheets I and II form a sandwich with a largely hydrophobic interior. The exposed side of the β-sheet I has a concave trend, whereas β-sheet II has a convex face. There are five antiparallel strands in each β-sheet; strands D and J have breaks with less defined secondary structure. A small two-turn α-helix is present in the crossover between strands E and F on the wider side of the sandwich. A single α-helical turn is apparent in the connection between strands G and H. Other connections adopt various forms of coiled structure. Three charged residues, K176, D209 and E301, are buried in the interior of the molecule and all are well defined in electron density maps. K176 and D209 are bridged through N293 by hydrogen bonds and residue E301 is hydrogen bonded to S199. Crystal packing results in large solvent channels, about 35 Å in diameter, along the three-fold screw axes. Domains are packed around the screw axes exposing most of the β-sheet II to the solvent channels.

Figure 3A:
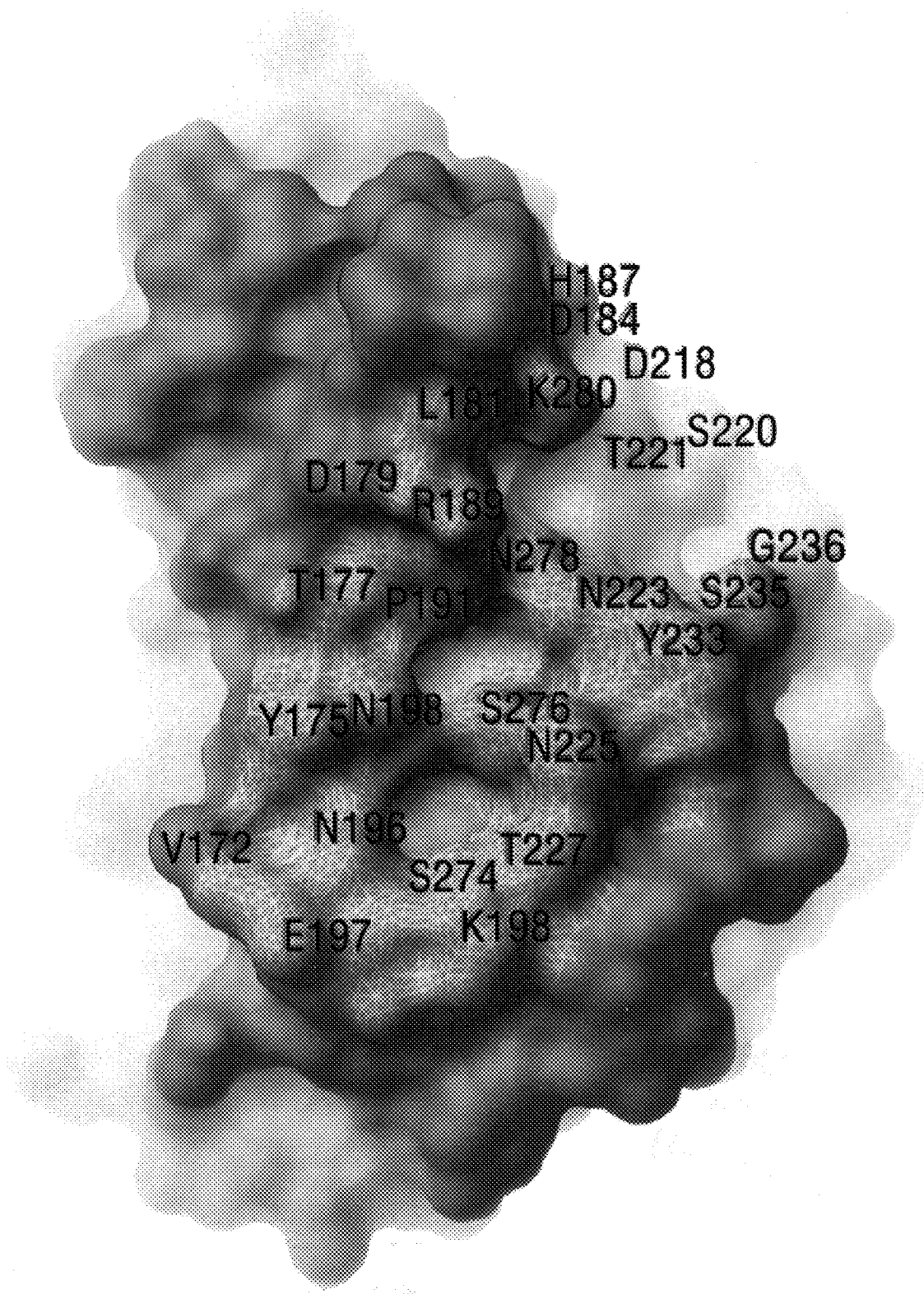

The Connolly's molecular surface (Connolly, 1983) of the CBD(169–318) crystal structure shows an apparent groove on the β-sheet I (FIG. 3A) indicating a putative Col binding region. This groove is about 10 Å wide and spans diagonally across strands D, H and B in the approximate direction T221-N196. With the exception of the disordered N-terminal residues 169 and 170 of a symmetry-related molecule, there are no significant short intermolecular contacts for the residues in and around the groove. The exterior residues on β-sheet I, specifically K280, R189, F191, Y175, E197, S235, Y233, N225, T227, and K198 (FIG. 3A) delimit and form the walls of the groove. Residues N193, N223, S274, and N278, with accessible surface area less than 20 Å$^2$, are buried in the groove; whereas, N196 and S276 are also inside the groove but relatively more exposed (FIG. 3A). The only hydrophobic residues in the putative Col binding region are V172, L181, and F191. Charged residues D179, E197, K198, D218, and K280 are located around the edges of the groove along with Y175 and Y233, whose phenolic rings are oriented towards the interior of the groove. Conformations of some side chains are stabilized by hydrogen bonds, for example R189 is hydrogen-bonded to D179, and K198 to S274. No tightly bound water molecules are found on the β-sheet I.

The peptide sequence D209-Y233 was previously shown to be essential for Col-binding activity (Patti et al., 1995). In the crystal structure, this sequence spans strand D and portions of strands C and E with exterior residues T221, N223, N225, T227, and Y233 in the putative Col binding region. In addition, the mutation of a residue 233Y→A in the 55-kDa domain A of the Col MSCRAMM has been shown dramatically reduced Col-binding activity (Patti et al., 1995).

5.2.4 Col Docking

Previous studies have shown that the Col binding MSCRAMM on *S. aureus* binds to several sites in different Col types (Patti et al., 1993) but recognizes collagens in a triple helical form (Speziale et al., 1986); therefore, the Col-binding site within the MSCRAMM, should have provisions for direct interaction with a triple-helical motif. Collagens are glycosylated to various degree depending on the tissue. The possibility of Col binding was tested through the carbohydrate by cocrystallization and soaking of CBD (151–318) with glucose, galactose, and lactose, respectively. Although high-quality isomorphous crystals were obtained, difference Fourier maps did not indicate any appreciable binding of the carbohydrates. The basic triple-helical conformation, approximately 15 Å in diameter, consists of three supercoiled polyproline II helices that require glycine residues to be present in every third position in the sequence. This results in a $(GLY-X-Y)_n$ repeating pattern in which the X and Y positions are frequently occupied by proline and 4-hydroxyproline (Hyp) residues, respectively. The hydroxyls of Hyp residues, essential for the structuring of water networks around the triple helices, play a critical role in stabilizing the Col (Bella et al., 1994). Other amino acids in the X and Y positions do not follow a clear pattern. The *S. aureus* Col-binding MSCRAMM recognizes synthetic peptides $(Gly-Pro-Pro)_n$ and $(Gly-Pro-Hyp)_{10}$ (Speziale et al., 1986) which are known to form a Col-like triple helix in solution (Sakakibara et al., 1973; Heidemann and Roth, 1982). Conversely, the receptor does not recognize polyproline, which cannot form the Col triple helix, or $(Gly-Ala-Pro)_n$, which is coiled in solution (Segal and Traub, 1969). Prior biosensor analysis of the MSCRAMM binding to type II Col indicated multiple binding sites of different affinities for Col. In particular, CBD(151–318) appears to recognize two classes of binding sites with apparent dissociation constants of $3\times10^{-6}$ M and $3\times10^{-5}$ M, respectively (Patti et al., 1993). It is likely that the MSCRAMM binds with higher affinity to specific Col sequences, but the triple helical structure of repeated Gly-Pro-Pro/Hyp appears to represent a general binding motif.

Figure 3B:
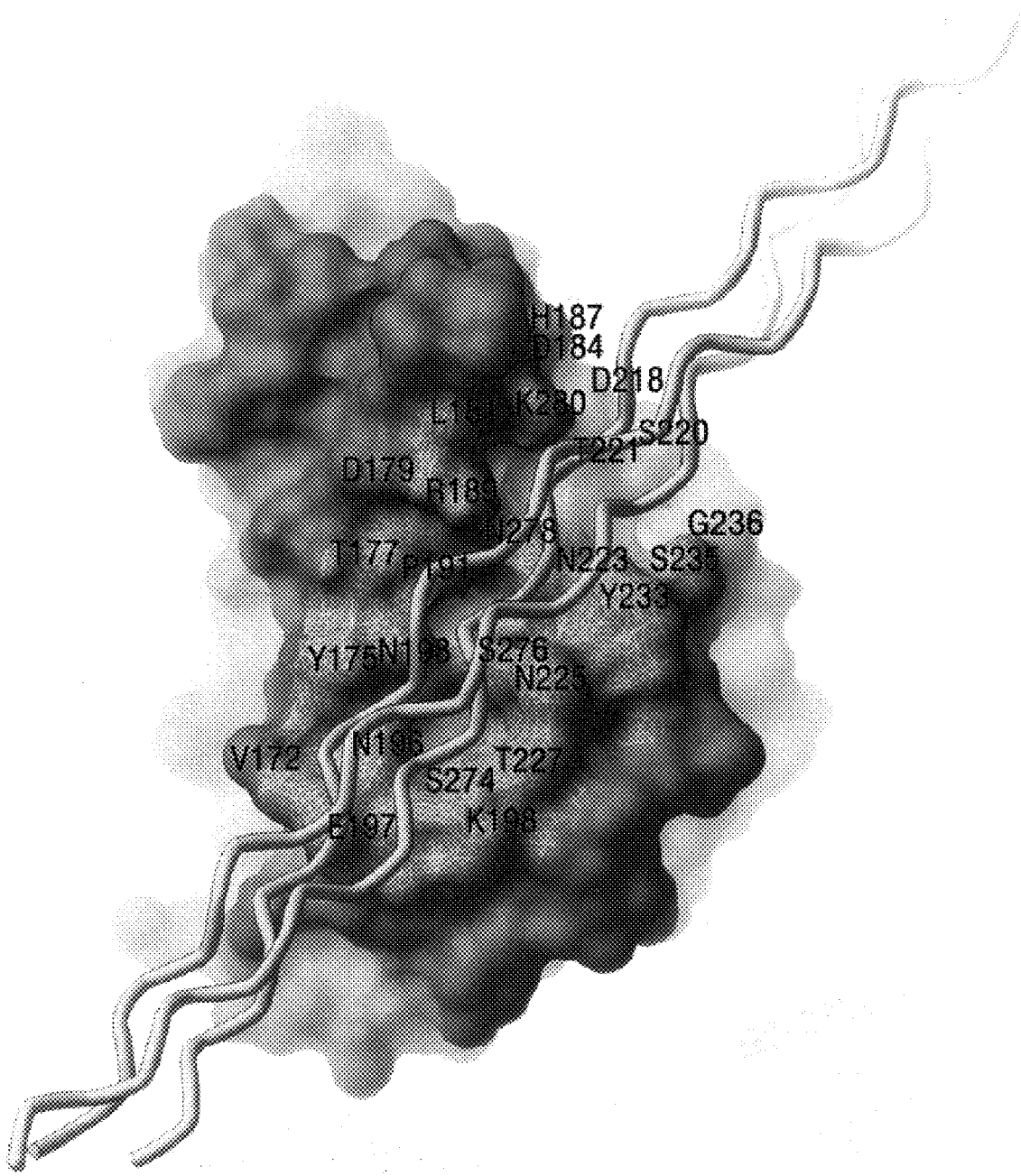

The compactness and relatively small size of the CBD (169–318) domain, the apparent tight association of its β-sheets, and additional information on adhesin specificity for the triple helical structures (Speziale et al., 1986) provided a unique opportunity for systematic docking studies. Probes with Gly-Pro-Pro/Hyp repeats were used in searching the entire molecular surface of the Col-binding domain for regions with geometric and chemical compatibility. A preliminary manual docking of the Col model to CBD (169–318) indicated that the surface of β-sheet I can accommodate a fragment of up to four repeats of Gly-Pro-Hyp or Gly-Pro-Pro per chain. Four Col probes were derived from the protein data bank for the docking calculations: 1BBE (Nemethy et al., 1992), a theoretical model of $[(Gly-Pro-Pro)_4]_3$ where acetyl and methyl amine terminal groups were deleted; 2CLG (Chen et al., 1991), a theoretical model of $[(Gly-Pro-Hyp)_{12}]_3$ that was shortened to $[(Gly-Pro-Hyp)_4]_3$ and to $[(Gly-Pro-Hyp)_6]_3$; and 1CAG (Bella et al., 1994), the crystal structure of a Col-like peptide $[(Pro-Hyp-Gly)_4$ Pro-Hyp-Ala $(Pro-Hyp-Gly)_5]_3$ shortened to the C-terminal $[(Gly-Pro-Hyp)_4]_3$. The docking target was the refined crystal structure of CBD(172–318) with the disordered N-terminal residues 169–171 excluded. The docking was performed as a full 6-dimensional search using the matching cubes algorithm (Jiang and Kim, 1991) implemented in the program SoftDock. The top sixteen solutions were evaluated in each search and solutions with the best scores were consistently found along the groove on β-sheet I in the direction T221-N196. Col helices were always oriented in this direction from the N- to C-terminus. The docking score became dramatically worse, when forced to the opposite direction. Apparently, the Col 'screw' matches the adhesin 'nut' in this site (FIG. 3B). Variations of the probe lengths, helical parameters, and proline ring conformations and interchanging of Pro and Hyp at the Y position of the probe had minimal effects on the final 'docked' positions. Both visual and computational analyses indicated no serious conflicts in chemical propensities and atomic distances between the binding site and Col probes. All successfully docked complexes are energy-minimizable in X-PLOR (Brunger, 1992) with a small loss of regular helicity and subtle conformational changes in receptor side chains.

5.2.5 Mutational Analysis

Figure 4:
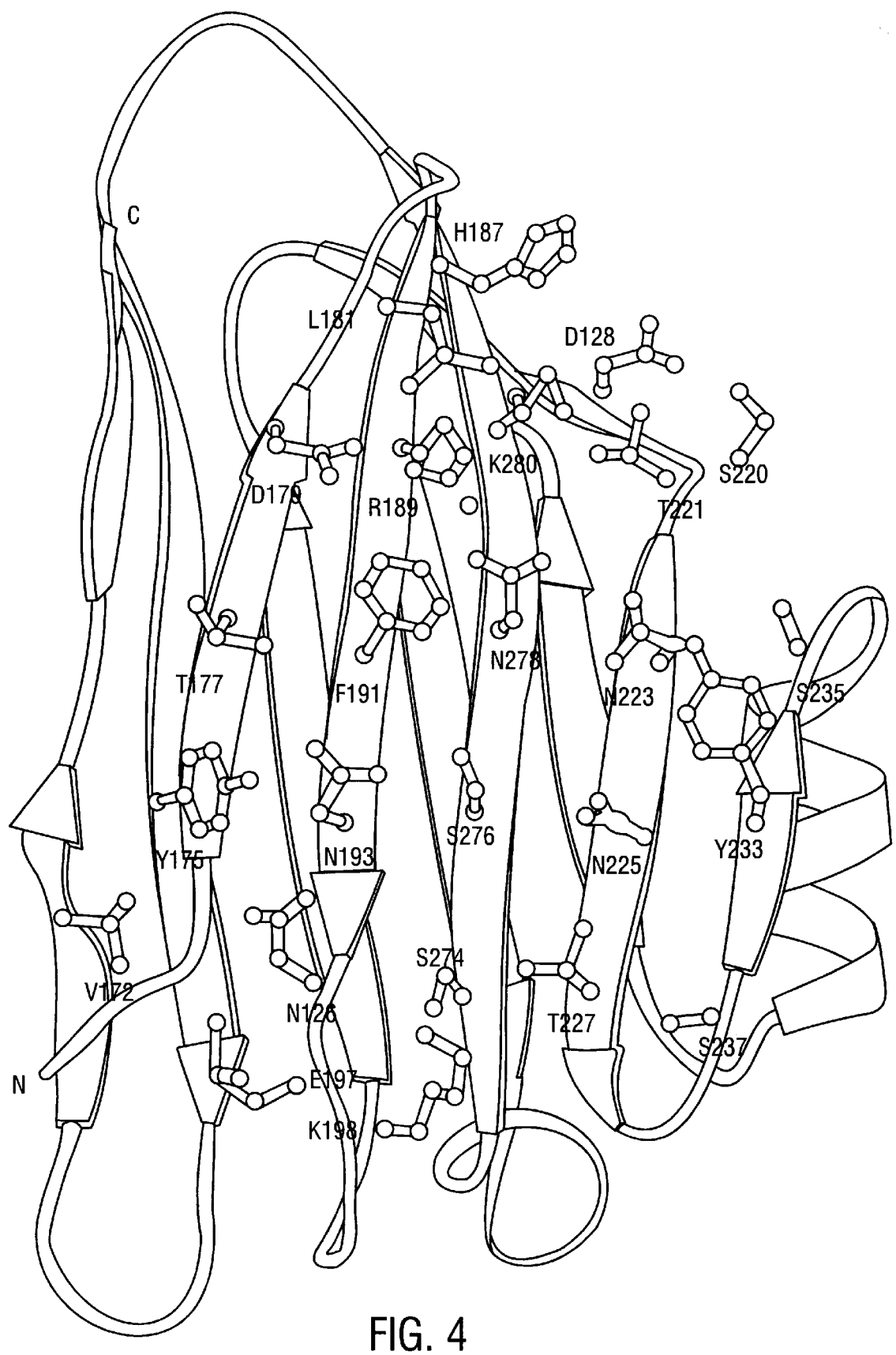

Mutational analysis was used to evaluate the putative binding site defined by the docking search. Surface residues that exhibited a decrease in their solvent accessible area were targeted (Table 3 and FIG. 4). The surface area covered by the docked Col is about 1630 Å$^2$, which is 22% of the total solvent-accessible surface of CBD(172–318). There are 19 residues on the interface that exhibited a decrease in solvent accessible area by more than 10 Å$^2$. Nine of these residues were mutated as well as two additional residues outside the putative binding region. The single-site lysine and alanine mutations were designed to disrupt the surface of the putative Col binding groove of wild type CBD (151–318). The mutant proteins did not exhibit significant changes in either the near-UV or far-UV circular dichroism spectra when compared to the recombinant wild type; affirming that the various mutations did not have a measurable effect on the overall conformation. The MSCRAMM recognizes generic triple-helical structures (Speziale et al., 1986; Sakakibara et al., 1973; Heidemann and Roth, 1982), therefore, changes in the low-affinity dissociation constants were used to evaluate alterations in the binding of the mutant proteins (House-Pompeo et al., 1994).

For mutants 212Q→A, 232N→A, 221T→K, and 225N→K (Table 3) the Col-binding activity, expressed as one apparent dissociation constant $K_D$, did not differ significantly from that of wild type CBD(151–318). Residue Q212 is located on the β-sheet II, far from the suggested binding site and was mutated as a control residue. This exhibited no significant change in affinity for the Col. The side chain of N232 is not part of the binding groove (FIG. 3A and FIG. 4) and does not exhibit a decrease in solvent accessibility on docking of the Col. Consistent with this, the mutation 232N→A in CBD(151–318) had a very small effect on Col binding. Residues T221 and N225 are marginal residues of the binding groove with relatively small side chains. Modeling studies show that the lysine side chains in positions 221 and 225 may adopt conformations which do not interfere with Col probes and point into the solvent region.

Site-specific alterations of residues N193, N223, and N278 to lysine residues resulted in recombinant proteins with a significantly reduced affinity for Col. These sites are in the interior of the binding groove and, according to the docking model, are practically buried by the bound Col. Consequently, the lysine side chains have less conformational freedom in these sites and may sterically prevent the adhesin from assuming the proper position along the Col helix. Significantly higher dissociation constant for 193N→K compared to the other two mutations could be attributed to its proximity to the putative Col binding groove 'wall' and critical residues Y175 and F191.

Mutations in positions Y233, F191, R189 and Y175 resulted in proteins with extremely low affinity for Col compared to wild type CBD(151–318), suggesting that these are some of the major determinants for Col binding. All four mutation sites involve large, relatively exposed, residues which form the side walls of the putative binding groove. The largest decrease in solvent-accessible area on Col docking is for Y233 and modeling studies have suggested a number of contacts with Col probes for this residue. Although residues R189 and Y175 exhibited relatively fewer contacts with docked Col probes, mutation of these residues essentially destroys Col binding with $K_D$ values approaching the millimolar range. The results for these two residues may be reflecting the simplicity of the probe used in modeling, and possible optimizations in 'docking' it. It is important to note that although generic peptides were used in the docking studies, biosensor analysis of the site-specific mutants demonstrated a high degree of correlation with native Col type II.

The mutational analysis shows two general trends. The Lys/Ala mutation of large residues forming the walls of the binding groove dramatically affects the affinity of the adhesin to Col. Mutation of smaller residues found inside the groove or close to its walls exhibit moderate to no effect on the binding. Overall, the results of mutational analysis are in good agreement with interactions seen in the Col-binding model derived from systematic docking of the generic Col probes. Binding of native Col will involve some non-proline residues in X/Y positions. Further modeling studies indicate that, in addition to recognizing the generic triplets, the binding site of CBD(151–318) can also accommodate other small non-proline residues. The predominant distribution of small polar residues (Thr, Asn, and Ser) in the binding groove might possibly mimic the essential hydration in stabilizing hydroxyprolines. In addition, they can sterically facilitate the binding of suggested diverse residues in Col sequence. Thus, it is possible that specific Col sequences may bind better than the generic triplets used in docking studies, and may account for the observed higher affinity binding sites on Col II (Patti et al., 1993).

TABLE 2

DATA COLLECTION AND PHASING STATISTICS OF CBD(151–318)

|  | Native | HgCl$_2$ (I) | HgCl$_2$ (II) | K$_2$PtCl$_4$ |
|---|---|---|---|---|
| Internal scaling |  |  |  |  |
| No. of crystals | 3 | 1 | 1 | 1 |
| Observed reflections | 104150 | 6505 | 10133 | 9040 |
| Unique reflections | 13094 | 3495 | 5588 | 3208 |
| Completeness (%) | 97.2 | 92.6 | 85.0 | 85.0 |
| Resolution (Å) | 2.0 | 3.0 | 2.5 | 3.0 |
| R$_{sym}$$^1$(%) | 7.8 | 7.0 | 5.8 | 3.2 |
| Derivative scaling |  |  |  |  |
| Resolution (Å) |  | 3.0 | 3.0 | 3.0 |
| R$_{merge}$$^2$(%) |  | 19.1 | 43.0 | 16.0 |
| No. of sites |  | 4 | 5 | 2 |
| Phasing power$^3$ |  | 2.09 | 2.73 | 1.83 |
| R$_{CULLIS}$$^4$(%) |  | 51.1 | 39.1 | 58.1 |
| R$_{KRAUT}$$^5$(%) |  | 7.6 | 18.4 | 6.5 |
| Figure of merit$^6$ |  | 0.442 | 0.390 | 0.423 |

$^1$R$_{SYM}$ = Σ$_h$Σ$_i$ |I(h) − I$_i$(h)|/Σh Σ$_i$ I(h), where I$_i$(h) and I(h) are the i-th and the mean measurements of the intensity of reflection h.
$^2$R$_{MERGE}$ = Σ$_h$ |F$_P$(h) − F$_{PH}$(h)/Σ F$_P$(h), where F$_P$(h) and F$_{PH}$(h) are observed native and scaled derivative structure factors of the reflection h.
$^3$Phasing power is the ratio of the root mean square (RMS) deviation of the calculated heavy-atom structure amplitudes to the RMS lack of closure.
$^4$R$_{CULLIS}$ = Σ |||F$_{PH}$|$_{OBS}$ + |F$_P$|$_{OBS}$ − |F$_H$|$_{CALC}$|/Σ ||F$_{PH}$|$_{OBS}$ + |F$_P$|$_{OBS}$|, where F$_{PH}$ and F$_P$ are the observed structure factor amplitudes for the heavy-atom derivative and the native data sets, with the sum taken over all centric reflections, and F$_H$ is the heavy-atom structure factor.
$^5$R$_{KRAUT}$ = Σ ||F$_{PH}$|$_{OBS}$ − Σ |F$_{PH}$|$_{CALC}$|/Σ|F$_{PH}$|$_{OBS}$, with the sum taken over all acentric reflections.
$^6$The overall figure of merit is 0.662.

TABLE 3

| CBD | K$_D$ (mM) | BR |
|---|---|---|
| CBD(151–318) | 31 | 10 |
| 212Q→A | 34 | 10 |
| 221T→K | 34 | 9 |
| 225N→K | 30 | 10 |
| 232N→A | 38 | 12 |
| 278N→K | 50 | 9 |
| 223N→K | 53 | 10 |
| 193N→K | 140 | 12 |
| 233Y→A | 195 | 11 |
| 191F→A | 199 | 10 |
| 189R→A | >350 | >13 |
| 175Y→K | >460 | >20 |

Apparent dissociation constants (K$_D$) and approximate binding ratios (BR) for binding of CBD(151–318) and corresponding mutants to Col type II as determined by biosensor analysis. Serial dilutions of each protein, wild type and mutants respectively, were passed over the covalently immobilized Type II Col [Sigma]. Equilibrium binding response after 10 seconds of injection was used to calculate the constants (Patti et al., 1995; House-Pompeo et al., 1994).

5.3 Example 3—Passive Immunization Using Epitopes of MSCRAMMs

Underlined amino acids are encoded in the vector pQE™-30 (Qiagen Inc. Chatsworth, Calif.).

5.3.1 *S. aureus* Col-Binding MSCRAMM Derivative M17 (SEQ ID NO:2)

<u>MRGSHHHHHHGS</u>ITSGNKSTNVTVHKSE A G T S S VFYYKTGDMLPEDTTHVRWFLNINNEKSYVSKDITI KDQIQGGQQLDLSTLNINVTGTHSNYYSGQSAITDF EKAFPGSKITVDNTKNTIDVTIPQGYGSYNSFSINY KTKITNEQQ KEFVNNSQA.

(GenBank accession number of entire cna gene is M81736).

5.3.2 *S. aureus* CBP Epitope M17DNA(SEQ ID NO:1)
ATAACATCTGGGAATAAATCAACGAATGTTACG
GTTCATAAAAGTGAAGCGGGAACAAGTAGTGTT
TTCTATTATAAAACGGGAGATATGCTACCAGAAGAT
ACGACACATGTACGATGGTTTTTAAATATTAACAAT
GAAAAAAGTTATGTATCGAAAGATATTACTATAAAG
GATCAGATTCAAGGTGGACAGCAGTTAGATTTA
AGCACATTAAACATTAATGTGACAGGTACACATAGC
AATTATTATAGTGGACAAAGTGCAATTACTGAT
TTTGAAAAGCCTTTCCAGGTTCTAAAATAACTGTT
GATAATACGAAGAACACAATTGATGTAACAATT
CCACAAGGCTATGGGTCATATAATAGTTTTTCAATT
AACTACAAAACCAAAATTACGAATGAACAGCAA
AAAGAGTTTGTTAATAATTCACAAGCT.

5.3.3 *S. aureus* Col-Binding MSCRAMM Derivative M31 (SEQ ID NO:4)

<u>MRGSHHHHHHGS</u>DDKVATITSGNKSTNVTV H K S EAGTSSVFYYKTGDMLPEDTTHVRWFLNINNEKSYV SKDITIKDQIQGGQQLDLSTLNINVTGTHSNYYSGQ SAITDFEKAFPGSKITVDNTKNTIDVTIPQGYGSYN SFSINYKTKITNEQQKEFVNNSQAWYQEHGKEEVNG KSFNHTVHNINANAGIEGTVKGE LKVLKQDKDTK.

(GenBank accession number of entire cna gene is M81736).

5.3.4 *S. aureus* CBP Epitope M31 DNA (SEQ ID NO:3)
GACGATAAAAATGGAAAAATACAAAATGGTGAC
ATGATTAAAGTGGCATGGCCGACAAGCGGTACA
GTAAAGATAGAGGGTTATAGTAAACAGTACCATTAA
CTGTTAAAGGTGAACAGGTGGGTCAAGCAGTTA
TTACACCAGACGGTGCAACAATTACATTCAATGATA
AAGTAGAAAAATTAAGTGATGTTTCGGGATTTG
CAGAATTTGAAGTACAAGGAAGAAATTTAACGC
AAACAAATACTTCAGATGACAAAGTAGCTACGA
TAACATCTGGGAATAAATCAACGAATGTTACGG
TTCATAAAAGTGAAGCGGGAACAAGTAGTGTTT
TCTATTATAAAACGGGAGATATGCTACCAGAAG
ATACGACACATGTACGATGGTTTTTAAATATTAACA
ATGAAAAAAGTTATGTATCGAAAGATATTACTATAA
AGGATCAGATTCAAGGTGGACAGCAGTTAGATT
TAAGCACATTAAACATTAATGTGACAGGTACAC
ATAGCAATTATTATAGTGGACAAAGTGCAATTA
CTGATTTTGAAAAAGCCTTTCCAGGTTCTAAAATAA
CTGTTGATAATACGAAGAACACAATTGATGTAACAA
TTCCACAAGGCTATGGGTCATATAATAGTTTTT
CAATTAACTACAAAACCAAAATTACGAATGAAC
AGCAAAAAGAGTTTGTTAATAATTCACAAGCTT
GGTATCAAGAGCATGGTAAGGAAGAAGTGAACG
GGAAATCATTTAATCATACTGTGCACAATATTAATG
CTAATGCCGGTATTGAAGGTACTGTAAAAGGTGAAT
TAAAAGTTTTAAAAC AGGATAAAGATACCAAG.

5.3.5 *S. aureus* Col-Binding MSCRAMM Derivative M55 (SEQ ID NO:6)

<u>MRGSHHHHHHGS</u>ARDISSTNVTDLTVS P S K I E D G GKTTVKMTFDDKNGKIQNGDMIKVAWPTSGTVK IEGYSKTVPLTVKGEQVGQAVITPDGATITFND KVE KLSDVSGFAEFEVQGRNLTQTNTSDDKVATITSGNK STNVTVHKSEAGTSSVFYYKTGDMLPEDTTHVRWFL NINNEKSYVSKDITIKDQIQGGQQLDLSTLNINVTG THSNYYSGQSAITDFEKAFPGSKITVDNTKNTIDVT IPQGYGSYNSFSINYKTKITNEQQKEFVNNSQAWYQ EHGKEEVNGKSFNHTVHNINANAGIEGTVKGELKVL KQDKDTKAPIANVKFKLSKKDGSVVKDNQKEIEIIT DANGIANIKALPSGDYILKEIEAPRPYTFDKDKEYP FTMKDTDNQGYFTTIENAKAIEKTKDVSAQKVW EGTQKVKPTIYFKLYKQDDNQNTTPV DKAEIKKLED GTTKVTWSNLPENDKNGKAIKYLVKEVNAQGED TTPEGYTKKENGLVVTNTE.

(GenBank accession number of entire cna gene is M81736).

5.3.6 *S. aureus* CBP Epitope M55 DNA (SEQ ID NO:5)
GCACGAGATATTTCATCAACGAATGTTACAGAT
TTAACTGTATCACCGTCTAAGATAGAAGATGGTGGT
AAAACGACAGTAAAAATGACGTTCGACGATAAA
AATGGAAAAATACAAAATGGTGACATGATTAAA
GTGGCATGGCCGACAAGCGGTACAGTAAAGATA
GAGGGTTATAGTAAAACAGTACCATTAACTGTTAAA
GGTGAACAGGTGGGTCAAGCAGTTATTACACCA
GACGGTGCAACAATTACATTCAATGATAAAGTA
GAAAAATTAAGTGATGTTTCGGGATTTGCAGAATTT
GAAGTACAAGGAAGAAATTTAACGCAAACAAAT
ACTTCAGATGACAAAGTAGCTACGATAACATCT
GGGAATAAATCAACGAATGTTACGGTTCATAAA
AGTGAAGCGGGAACAAGTAGTGTTTTCTATTAT
AAAACGGGAGATATGCTACCAGAAGATACGACA
CATGTACGATGGTTTTTAAATATTAACAATGAA AAA
AGTTATGTATCGAAAGATATTACTATAAAGGATCAG
ATTCAAGGTGGACAGCAGTTAGATTTAAGCACATTA
AACATTAATGTGACAGGTACACATAGCAATTATTAT
AGTGGACAAAGTGCAATTACTGATTTTGAAAAA
GCCTTTCCAGGTTCTAAAATAACTGTTGATAATACG
AAGAACACAATTGATGTAACAATTCCACAAGGC
TATGGGTCATATAATAGTTTTTCAATTAACTAC
AAAACCAAAATTACGAATGAACAGCAAAAAGAG
TTTGTTAATAATTCACAAGCTTGGTATCAAGAGCAT
GGTAAGGAAGAAGTGAACGGGAAATCATTTAAT
CATACTGTGCACAATATTAATGCTAATGCCGGTATT
GAAGGTACTGTAAAAGGTGAATTAAAAGTTTTA AAACAGGATAAAGATACCAAGGCTCCTATAGCTAAT
GTAAAATTTAAACTTTCTAAAAAAGATGGATCAGTT
GTAAAGGACAATCAAAAAGAAATTGAGATTATA
ACAGATGCAAACGGTATTGCTAATATTAAAGCGTTG
CCTAGTGGAGACTATATTTTAAAAGAAATAGAG
GCGCCACGACCGTATACATTTGATAAGGATAAA
GAATATCCGTTTACTATGAAAGATACAGATAATCAG
GGATATTTTACGACTATTGAAAATGCAAAAGCGATA
GAAAAAACAAAAGATGTTTCTGCTCAAAAGGTT
TGGGAAGGCACTCAAAAAGTGAAACCAACGATT
TATTTCAAGTTGTACAAACAAGATGACAATCAAAAT
ACAACACCAGTAGACAAAGCAGAGATTAAAAAA
TTAGAAGATGGAACGACAAAAGTGACATGGTCT
AATCTTCCGGAAAATGACAAAAATGGCAAGGCT
ATTAAATATTTAGTTAAAGAAGTAAATGCTCAAGGT
GAAGATACAACACCAGAAGGATATACTAAAAAA
GAAAATGGTTTAGTGGTTACTAATACTGAA.

5.3.7 *S. aureus* Fib-Binding MSCRAMM Derivative PCF33 (SEQ ID NO:7):

MRGSHHHHHHGSMVAADAPAAGTDITNQLT N V T
VGIDSGTTVYPHQAGYVKLNYGFSVPNSAVKGDTFK
ITVPKELNLNGVTSTAKVPPIMAGDQVLANGVIDSD
GNVIYTFTDYVNTKDDVKATLTMPAYIDPENVKKTG
NVTLATGIGSTTANKTVLVDYEKYGKFYNLSIKGTI
DQIDKTNNTYRQTIYVNPSGDNVIAPVLTGNLKPNT
DSNALIDQQNTSIKVYKVDNAADLSESYFVNPENFE
DVTNSVNITFPNPNQYKVEFNTPDDQITTPYIVVVN
GHIDPNSKGDLALRSTLYGYNSNIIWRSMSWDNEVA
FNNGSGSGDGIDKPVVPEQPDEQA.

(GenBank accession number of entire clfA gene is Z18852).

5.3.8 *S. aureus* Fibrinectin-Binding MSCRAMM Derivative PQD (SEQ ID NO:8)

MRGSHHHHHHGSEGGQNSGNQSFEEDTEEDKPKY
EQGGNIVDIDFDSVPQIHGQNKGNQSFEEDTEKDKP
KYEHGGNIIDIDFDSVPHIHGFNKHTEIIEEDTNKD
KPSYQFGGHNSVDF EEDTLPKVSGQNEFDIKLN.

(GenBank accession number of entire fnbA gene is 128324).

5.3.9 Use of the Purified Hyperimmune Polyclonal Rabbit Anti-MSCRAMM IgG in Passive Immunization 5.3.9.1 Bovine Mastitis Several studies have suggested that epithelial cell damage and the exposure of ECM molecules within the teat canal orifice and mammary gland are critical factors leading to the development of mastitis (Gudding et al. 1984; Olmsted and Norcross 1992; Cifrian et al. 1995) *S. aureus* adhesion to mammary gland tissue is regarded as the first step in the development of mastitis. Therefore, adhesins that mediate *S. aureus* attachment to bovine mammary gland tissues are critical targets for the development of blocking antibodies. Hyperimmune polyclonal antibodies generated against several MSCRAMMs have been analyzed for their ability to inhibit *S. aureus* strain M60 attachment to cultured bovine mammary secretory epithelial cells. A dose dependent decrease in the adherence of *S. aureus* was demonstrated with the rabbit polyclonal anti-MSCRAMM IgG to the CBPs of SEQ ID NO:2, SEQ ID NO:7, and SEQ ID NO:8.

5.3.9.2 Experimantal Details

Briefly, $5\times10^4$ secretory epithelial cells, in 100 µl culture medium, were added to flat-bottom Col coated 96-well plates and grown to confluence at 37° C. The *S. aureus* strains were grown overnight in trypticase soy broth (TSB) at 37° C. The overnight culture was diluted into fresh TSB and grown until the culture reached the exponential phase, the organisms were harvested and resuspended into 3 ml fresh culture media. The bacteria ($3.1\times10^8$) were incubated with increasing amounts of anti-MSCRAMM IgG for 30 min at 37° C. The pre-treated bacteria were then added to was added to the cell monolayers ($4.1\times10^6$ epithelial cells) and incubated for 3 hr at 37° C. The monolayers were then washed five times with phosphate buffered saline. The monolayers were fixed with methanol and stained with Giemsa. Twenty fields (100×objective) were examined in each monolayer for the presence of adherent bacteria.

5.3.10 Peritonitis

Patients undergoing dialysis (continuous ambulatory peritoneal dialysis, hemodialysis) present an increased risk for the development of staphylococcal infections. Using an animal model of peritonitis (Menzies and Kernodle 1996) we have demonstrated that passive immunization with a single subcutaneous dose of anti-MSCRAMM IgG can protect mice against *S. aureus* intraperitoneal challenge. When mice were challenged with *S. aureus*, only twenty-seven percent (10/37) of the mice passively immunized with anti-MSCRAMM IgG became infected Conversely, 76% of the mice passively immunized with normal rabbit serum became infected. *Compilation of 3 separate studies.

Male NIH Swiss mice, 6–8 weeks of age weighing 18–22 g (Harlan Sprague Dawley, Indianapolis, Ind.) were used. Anti-MSCRAMM IgG was administered as a 0.25 ml subcutaneous (s.c.) injection into the thigh of the mice. Control mice received an equivalent amount of normal rabbit IgG (Sigma Chemical Co. St. Louis, Mo.). Forty-eight hr post immunization, mice were challenged intraperitoneally (i.p.) with *S. aureus*. The bacterial strain was prepared by growing overnight in brain heart infusion broth (Becton Dickinson Microbiology Systems, Cockeysville, Md.), washing twice in PBS, and resuspending in PBS, adjusting by light transmission to a concentration of $6\times10^8$ cfu/ml. Mice were inoculated with 0.5 ml of the bacterial suspension. An aliquot of the bacterial suspension was plated on sheep blood agar to determine the exact cfu/ml.

Mice were sacrificed 48 hr post bacterial inoculation. Both kidneys from each mouse were aseptically excised, weighed, placed in a sterile bag containing 0.5 ml of PBS, and homogenized for 30 sec using a Tekmar Tissumizer (Tekmar, Cincinnati, Ohio). The homogenate was serially diluted in sterile water and plated on sheep blood agar plates and incubated at 37° C. The plates were counted 18–24 hr later. Homogenates of kidneys from mice containing <100 cfu/ml were considered negative. The results are shown in Table 4.

TABLE 4

| Total IgG Dose (mg/mouse) | Anti-MSCRAMM Rabbit IgG # infected mice/total mice (%) | Normal Rabbit IgG # infected mice/total mice (%) |
|---|---|---|
| 0.3 | 5/6 (83%) | 4/5 (80%) |
| 0.6 | 1/6 (17%) | 4/6 (67%) |

TABLE 4-continued

| Total IgG Dose (mg/mouse) | Anti-MSCRAMM Rabbit IgG # infected mice/total mice (%) | Normal Rabbit IgG # infected mice/total mice (%) |
|---|---|---|
| 1.63 | 8/23 (35%)[a] | 16/21 (76%) |
| 3.50 | 1/8 (13%)[b] | 8/10 (80%) |

[a]P = 0.006
[b]P = 0.005

5.3.11 Demonstration of Therapeutic Efficacy in the Pneumonia Model

*Staphylococcus aureus* is a life-threatening agent of nosocomial pneumonia in immunocompromised patients. Often *S. aureus* isolated from these patients exhibit wide-spectrum resistance to antibiotics, particularly methicillin. An experimental mouse model of staphylococcal pneumonia (Ramisse et al., 1993) was used to assess the ability of anti-MSCRAMM IgG to protect neutropenic mice against *S. aureus* mediated pneumonia. Mice that had been treated intranasally with anti-MSCRAMM IgG 3 hours after bacterial inoculation had over a 1000-fold reduction in the amount of bacteria recovered from their lungs (p<0.01) compared to the PBS control treated animals.

5.3.11.1 Experimantal Details

Female 4 week-old BALB/c mice were treated intravenously with cyclophosphamide at 150 mg/kg at day 4 and 75 mg/kg at day 1 before bacterial challenge. Cyclophosphamide induces a transient neutropenia in the mice. *S. aureus* were grown in trypticase soy broth (TSB) overnight at 37° C. The cultures were washed and adjusted to Å $6.3\times10^6$ cfu/ml in PBS. An aliquot of the bacterial suspension was plated on sheep blood agar to determine the exact cfu/ml. The mice were anesthetized and were inoculated with 50 μl of the bacterial suspension. Three hours after the bacterial challenge each mouse received either 7.5 μg anti-MSCRAMM IgG, 75 μg anti-MSCRAMM IgG, or PBS intranasally. To check colonization of the lungs by the bacteria, 5 mice per time point are sacrificed. Bacterial counts are determined from lung homogenates (lungs are carefully dissected from the main bronchia) serially diluted in PBS by plating 100 μl-aliquots on trypticase soy agar and counting the cfu after incubation for 24 hr at 37° C. Bacterial counts were expressed as the mean (±SE). Statistical significance was determined by Student's t test. The results are shown in Table 5.

TABLE 5

| | Kinetics of pulmonary infection (cfu/ml) | | |
|---|---|---|---|
| Treatment | 3 hr | 24 hr | 48 hr |
| Study 1 | | | |
| PBS-control | 4.80 ± 0.09 | 6.40 ± 0.30 | 7.93 ± 0.20 |
| 7.5 μg anti-MSCRAMM IgG/mouse | 4.94 ± 0.14 | 6.33 ± 0.38 | 7.04 ± 0.12 |
| 75 μg anti-MSCRAMM IgG/mouse | 5.20 ± 0.08 | 6.03 ± 0.70 | 5.53 ± 0.80[a] |
| Study 2 | | | |
| PBS-control | 5.30 ± 0.03 | 7.15 ± 0.08 | 7.98 ± 0.11 |
| 7.5 μg anti-MSCRAMM IgG/mouse | ND | 5.50 ± 0.54 | 5.52 ± 0.40 |

[a]p < 0.01
ND = not done.

5.3.12 Passive Immunization Using CBP Epitopes

Figure 8:
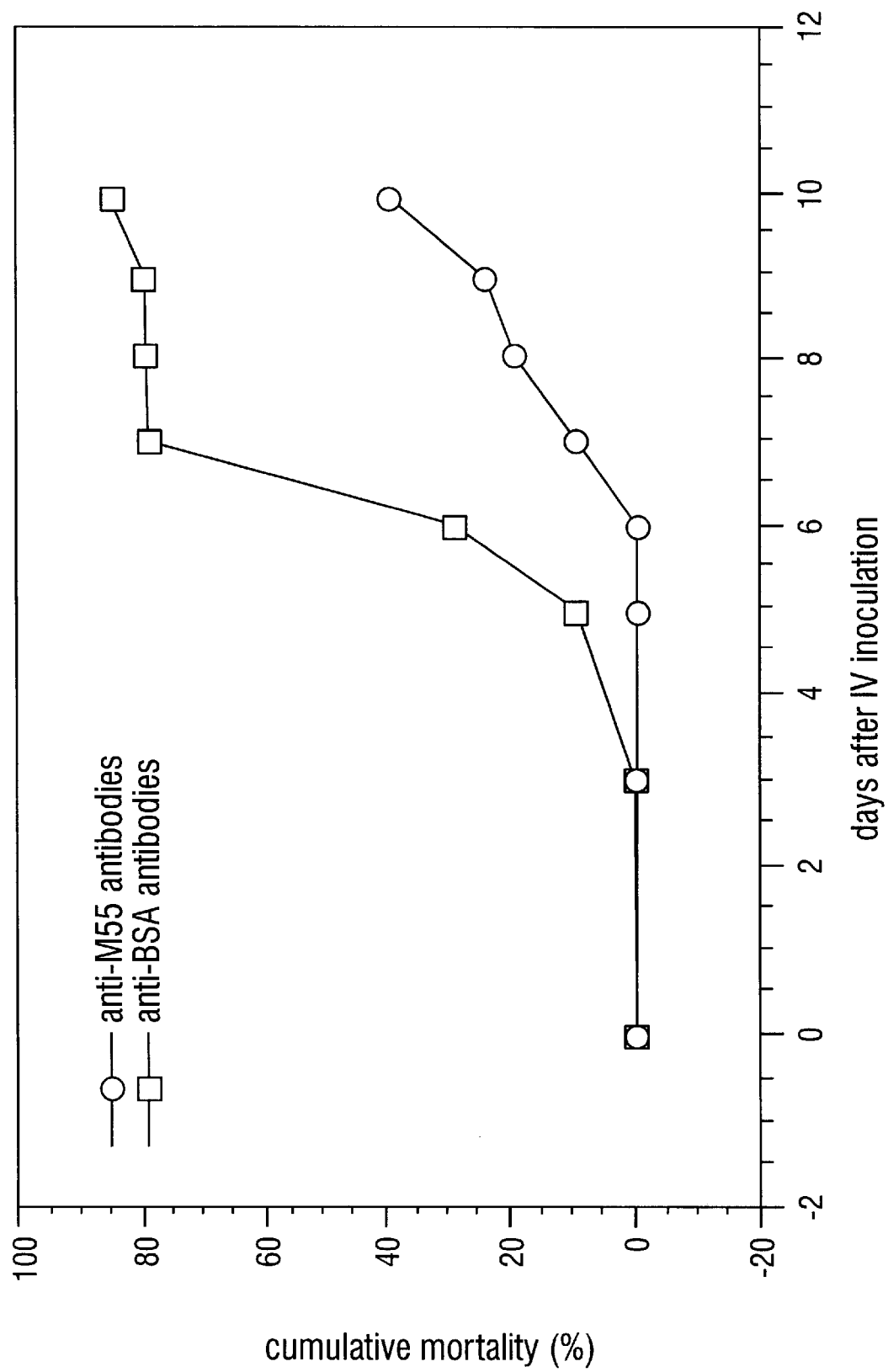
FIG. 8 is a graphic representation of the protective effective in mice against a lethal *S. aureus* challenge by passive immunization with rat anti-M55 in accordance with the present invention.

In separate studies, rats were immunized with M55 or BSA as a control as described herein. They were bled and the IgG fraction obtained by ammonium sulfate precipitation. The IgG fraction (16 mg) was administered to mice 1 day before IV challenge with *S. aureus*. These passive immunization data confirm the efficacy of the active immunization—i.e., antibodies directed against M55 of the CBP protect against lethal doses of *S. aureus* (FIG. 8).

5.4 Example 4—Animal Studies Involving the *S. aureus* CBP

Corneal infection is a leading cause of visual loss and is a major public health problem in the U.S. Bacterial keratitis results when microbial virulence factors overcome host defense mechanisms. The successful corneal pathogen attaches to the corneal surface, avoiding the clearance mechanisms of the tear film. Specific bacterial surface proteins adhere to specific components of the cornea, such as fibronectin, fibrinogen, and Col. Specific microbial adhesins mediate this adherence by sophisticated interaction with host molecules.

*S. aureus* MSCRAMMs have been studied using various animal models. These MSCRAMMS are localized to the surface of *S. aureus* and interact with ECM components with high affinity and high specificity. MSCRAMMS recognizing fibronectin, fibrinogen, and Col have been previously described with respect to structural organization, ligand-binding domains, importance in host colonization and invasion, and biological roles as virulence factors.

The inventors have utilized both in vitro and in vivo studies to determine the role of CBP in the pathophysiology of infectious keratitis.

5.4.1 Col Binding by Ocular Isolates

Twenty clinical isolates of *S. aureus* from the Cullen Eye Institute at the Baylor College of Medicine (Houston, Tex.) were selected randomly. Each was isolated from a previous case of bacterial keratitis with standard clinical techniques. Type II Col was labeled with $^{125}$I by the chloramine-T method. A 5-ml culture of each strain was grown overnight in Brain-heart infusion broth. Cells were centrifuged and resuspended in 1 ml of PBS. For each assay, 50 μl of bacterial cells (approximately $5\times10^8$ cfu/ml) was incubated with 400 μl of PBS with 0.1% BSA and 0.1% Tween 80® and $5\times10^4$ cpm of the $^{125}$I-labeled type II Col. Tubes were incubated at room temperature for 1 hr and rotated end-over end. The reaction was stopped by the addition of 3 ml of ice-cold PBS containing 0.1% Tween 80® and the tubes were immediately centrifuged at 1500×g for 20 min. After aspiration of the supernatant, the pellet containing bacterial cells was analyzed for radioactivity in a gamma counter. Triplicate samples were analyzed, and background values representing radioactivity recovered in the tubes incubated in the absence of bacteria was subtracted.

Analysis of the clinical isolates suggested that binding to Col is an "all-or-none" phenomenon. Thirty percent (6/20) of the *S. aureus* isolates bound to labeled Col. An additional 18 *S. aureus* strains isolated from the vitreous of patients with bacterial keratitis were also analyzed for Col binding activity. Interestingly, 72% (13/18) of those strains bound Col. Taken together these data suggest that Col binding is an important virulence determinant in the pathogenesis of *S. aureus* eye infections.

5.4.2 Animal Studies Involving *S. aureus* Keratitus

In subsequent studies, the inventors have examined whether ability to bind Col was important in production of microbial keratitis in the rabbit. Previous animal models of *S. aureus* keratitis have required direct intrastromal injection to induce infection. Microbial adhesion to damaged corneal tissue is most likely the initiating event in the development keratitis, therefore to more closely mimic the natural course of disease an animal model was developed that doesn't involve intrastromal injection. To determine whether the *S. aureus* Col MSCRAMM can be considered a virulence factor in keratitis a rabbit model developed for this study. Soft contact lenses were placed in culture media of *S. aureus* strain Phillips (CBP+) and its isogenic mutant derivative PH100 (CBPs. The contact lenses were incubated for 24 h in the culture media that contained approximately $10^8$ bacteria. This resulted in $1 \times 10^6$ bacteria bound to the contact lens for PH100 and $2 \times 10^5$ organisms bound to the lens for strain Phillips. This difference was not statistically significant. The soft contacts were washed in PBS to remove any loosely bound organisms and were then were placed onto the de-epithelialized corneas of New Zealand White rabbits. The nictitating membrane of the rabbits was removed to prevent dislocation of the contact lens and the eyelids were sutured closed with 7-0 Vicryl®. In a blinded trial a total of 16 rabbits, 8 in each group were used. Eyes were opened after 48 h of contact lens placement. Corneal scrapings were performed and placed onto blood agar to confirm the presence of infection and corneas were removed for histological examination. One of the rabbits assigned to CBP− group developed spontaneous dehiscence of the tarsorrhaphy closure and loss of the contact lens, so the animal was removed from study. Seventy-five percent (6/8) of the rabbits with contact lenses incubated with strain Phillips (CBP+) developed clinical microbial keratitis, as evidenced by dense, central suppurative stromal keratitis. Cultures confirmed the presence of *S. aureus* in all infected cases. Conversely, 0/7 rabbits with contact lenses incubated with the PH100 developed suppurative keratitis, though in all cases the epithelial defect remained. This difference in rate of keratitis was statistically significant (Fisher's exact test p=0.006).

The efficacy of a small molecule inhibitor based on the 3-D structure of CBD(151–318) can be tested using the bacterial keratitis model. After the contact lens has been incubated with *S. aureus* and washed to remove any loosely bound organisms the contaminated contact is placed in a solution that contains the inhibitor. The inhibitor will bind to the active site thereby saturating the Col MSCRAMM thereby preventing the bacteria from adhering to the exposed Col fibers in the damaged cornea. In addition to preventing *S. aureus* bacterial keratitis, the inhibitor would be added to solutions commonly used by eye banks to prevent infections in recipients of donor lenses.

5.5 Example 5—Mouse Model of Septic Arthritis

Using the mouse model of septic arthritis (Bremell et al., 1992), the inventors have studied the use of recombinant domains, CBD(151–297) and CBD(61–343), of the *S. aureus* Col MSCRAMM as a vaccine components. 18 mice were vaccinated with 100 µg of protein (GST-61-343) in Freund's complete adjuvant (FCA) on day days −34, −21, −9. 25 control mice were injected with PBS-FCA on the same days. The mice were challenged with an intravenous injection of *S. aureus* strain Phillips on day 0. The mice immunized with GST-61-343 had a 50% reduction in arthritis compared to the control mice. Additional studies have also been performed which use different domains of the *S. aureus* Col MSCRAMM.

5.6 Example 6—Evidence that Only Particular CBP Epitopes Confer Protection Against *S. aureus* Infection The following example shows the effective use of CBP epitopes as vaccine components, and compositions useful in conferring protection to an animal against infection by *S. aureus*.

5.6.1 Mouse Sepsis Model—CBP Epitopes Utilized

M17 contains amino acids 151–297 of the full length CBP (SEQ ID NO:2).

M31 contains amino acids 61–343 of the full length CBP (SEQ ID NO:4).

M55 contains amino acids 30–531 of the full length CBP (SEQ ID NO:6).

The DNA segments encoding M17, M31, and M55 epitopes are disclosed in SEQ ID NO:1, SEQ ID NO:3, and SEQ ID NO:5, respectively.

5.6.2 Immunization Schedule

Day −31: 100 µg/mouse of a CBP Epitope (i.e. M17, M31, or M55) or BSA emulsified with Freund's Complete adjuvant (Difco Laboratories) as a control.

Day −18: 100 µg/mouse of a CBP Epitope (i.e. M17, M31, or M55) or BSA dissolved in sterile phosphate buffered saline (PBS)

Day −7: 100 µg/mouse of a CBP Epitope (i.e. M17, M31, or M55) or BSA dissolved in PBS Day 0: inoculate intravenously *S. aureus* strain Phillips (which expresses CBP) (Dose: $2.8 \times 10^7$ cfu/mouse)

Day 14: end of study; all surviving mice were euthanized.

5.6.2 Results

10/15 mice died in the M17 Col-binding MSCRAMM group

12/14 mice died in the M31 Col-binding MSCRAMM group

4/11 mice died in the M55 Col-binding MSCRAMM group.

All 15 of 15 mice died in the BSA control group.

In a control study, M55 and BSA immunized mice were challenged with a strain of *S. aureus* that does not express the Col-binding MSCRAMM. The mortality in the M55 group was 50% compared to 30% in the BSA group. Importantly, these data indicated that protection is directly related to antibodies generated against the M55 portion of the Col binding MSCRAMM.

In sharp contrast to the previously-identified full-length sequence which does not confer protection against sepsis in an in vivo animal model, these data clearly show that M55 (containing only the A domain) was highly effective in protecting against sepsis.

Surprisingly, while all of the CBP fragments (M17 and M31) are contained within the M55 protein sequence, only M55 is highly protective.

5.7 Example 7—Opsonization, Phagocytosis and Intracellular Killing of Bacteria The phagocytosis test was done by a modification of the previously described method (Lissner et al., 1983). Briefly, peritoneal macrophages were collected from the peritoneal cavity by injecting 3 ml of ice cold medium (Iscoves medium containing 10% fetal calf serum, and 100 µg/ml of gentamycin) i.p., after one minute massage of the abdomen the macrophage containing medium was aspirated. The macrophages were washed and adjusted to $2 \times 10^6$ cells/ml, seeded in 200 µl volumes in 24-well plates (Nunc, Roskilde, Denmark) and left at room temperature for 90 min. Five-hundred µl of cell culture medium was added to each well and the cells were incubated for 24 hours in 37° C. The medium was then removed and replaced by 500 µl of a medium free of antibiotics and the cells were then incubated overnight at 37° C. The next day the staphylococci were opsonized for 30 min at 4° C. with either a) 50% heat inactivated sera of mice that have been hyperimmunized with M55 or b) with sera from BSA hyperimmunized mice or alternatively c) with sera from mice that have gone through infection with strain Phillips without previous immunization. Five-hundred μl of opsonized staphylococci were added to the wells in a concentration of $1.4 \times 10^7$ bacterial/ml. After 50 min of incubation, the macrophages were washed 3 times in Iscovés in order to remove non-ingested bacteria. Thereafter, the macrophages were analyzed either directly after bacterial incubation or 4 hours later. To those cultures that were incubated for 4 hours, Iscovés medium with the minimal inhibitory concentration of gentamycin suitable for S. aureus strain Phillips (5 μg/ml) was added to avoid extracellular replication of bacteria. The macrophages were lysed with distilled water for 20 minutes, and the lysate diluted 1/1, 1/10, 1/100, and 1/1000 was cultured on 5% horse blood agar plates. The plates were incubated overnight and the number of bacteria counted.

5.7.1 In Vitro Assays

In vitro assays were performed to assess the impact of specific antibodies to collagen adhesion on phagocytosis and intracellular killing capacity. Collagen adhesion expressing Phillips strain was opsonized with either serum containing M55 specific antibodies or serum containing BSA antibodies, or alternatively serum from naive mice that have gone through infection with Phillips.

Figure 5A:
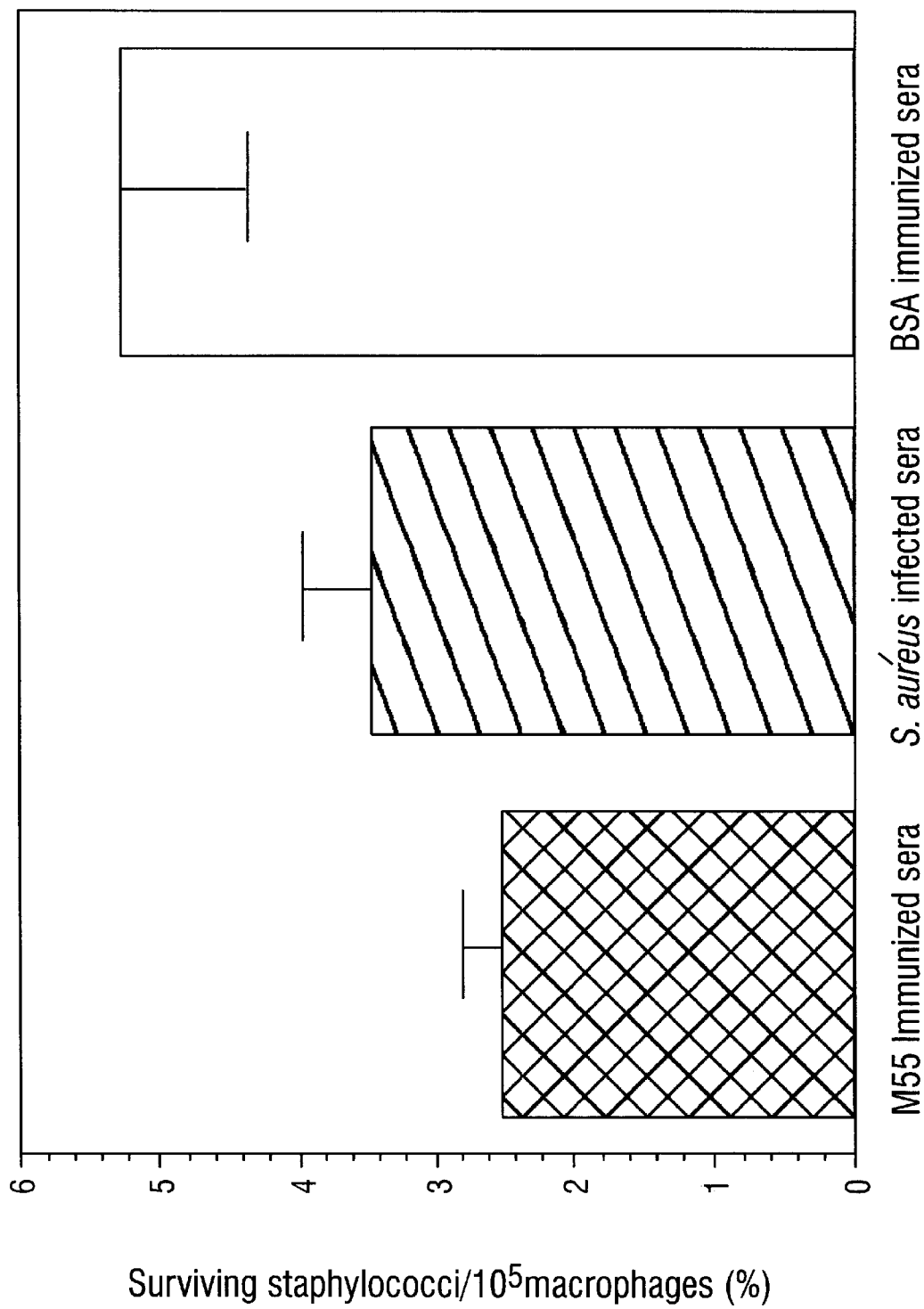
FIG. 5A is a graphic representation of the enhancement of macrophage killing enabled by immunization with M55 in accordance with the present invention.
Figure 5B:
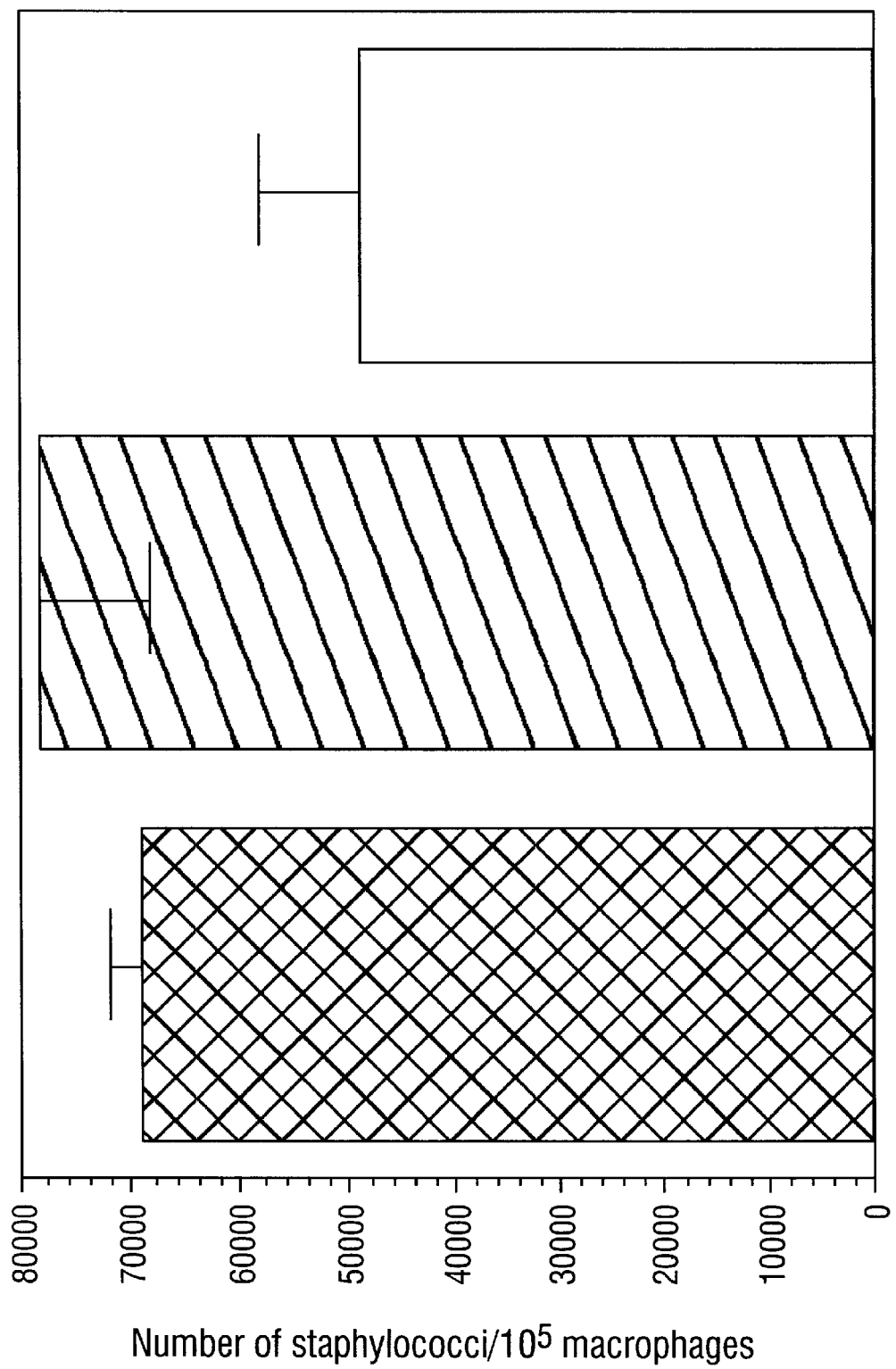
FIG. 5B is a graphic representation of the enhancement of phagocytosis enabled by immunization with M55 in accordance with the present invention.

The results (FIG. 5A) show clearly that intracellular killing of S. aureus Phillips strain is moderately enhanced by a previous infection with the same strain (p=0.037). In contrast, opsonization of staphylococci with serum from M55 mice immunized (but not infected) mice displayed significantly enhanced intracellular killing capacity as compared to control serum (p=0,009). The phagocytic capacity was only modestly affected by opsonization of bacteria with serum containing M55 antibodies and significantly affected when the bacteria were opsonized with serum of Phillips strain infected mice (FIG. 5B).

5.8 Examle 8—Detection of CBP Antibodies in Mice Infected with S. aureus

In this study, 15 mice were experimentally infected with a sub-lethal dose of S. aureus that expresses the Col-binding MSCRAMM. Anti-M55 (Col MSCRAMM) IgG could not be detected in the sera from the infected animals. Conversely, animals immunized with M55 and infected with a sub-lethal dose S. aureus had anti-M55 IgG (Col MSCRAMM) titers of $32 \times 10^9$ units/ml.

These data indicate that during the normal course of infection, the CBP is protected from immunological recognition. The induction of polyclonal B-cell activation, as a consequence of infection with S. aureus will down regulate specific immune responses to many bacterial cell wall components, including the native CBP.

5.8.1 Experimantal Details

Serum level of specific antibodies against the collagen adhesion peptide M55 was measured by an enzyme-linked immunosorbent assay (ELISA). 96-well microplates (Nunc) were coated overnight at 4° C. with 2 μg/ml of M55 peptide. Blocking was done with 0.5% ovalbumin (Sigma Chemical Co., St. Louis, Mo.) dissolved in 0.05 M Tris (pH 7.7). Sera, biotinylated antibodies, and ExtrAvidin-peroxidase (Sigma) were all diluted in 0.05 M Tris (pH7.4)-0.015 M NaCl. The plates were incubated overnight at 4° C. with sera, washed and incubated stepwise with biotinylated goat anti-mouse IgG antibody (Jackson Immuno Research Laboratories, Inc., West Grove, Pa.), ExtrAvidin-peroxidase (0.5 μg/ml; Sigma) and ABTS substrate. The A405 was measured in a Titertec Multiscan photometer (Flow Laboratories, McLean, Va.). Similar ELISA procedure as described above was employed to detect antibodies to M17, M31, as well as to the B1 domain of collagen adhesion. OVA was used as control solid antigen.

Figure 6:
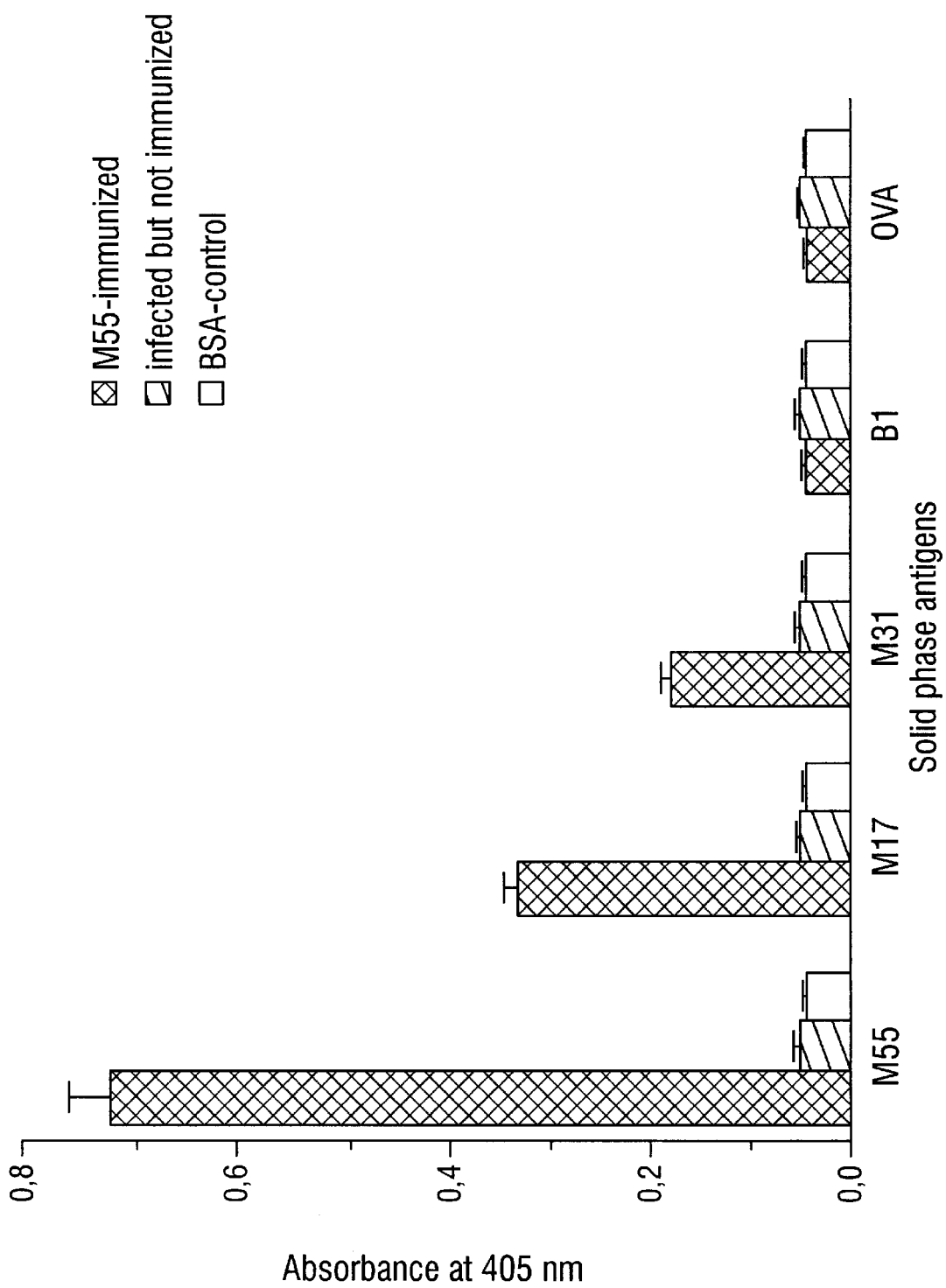
FIG. 6 is a graphic representation of studies determining the serum level of antibodies against the collagen adhesin peptides of the present invention.

In addition, 96-well plates were precoated with poly-L-lysine (Sigma) and then coated with either $1.5 \times 10^7$ S. aureus strains Phillips or LS-1. After blocking procedure sera from immunized mice and unimmunized but infected mice as well as naive mouse sera, were incubated. The development steps were then made as described above. The data are shown in FIG. 6.

5.9 Example 9—Detection of Antibodies to Col-Binding MSCRAMMS in Humans Infected by S. aureus This example describes the results of studies to detect antibodies to the Col binding MSCRAMM.

Figure 7A:
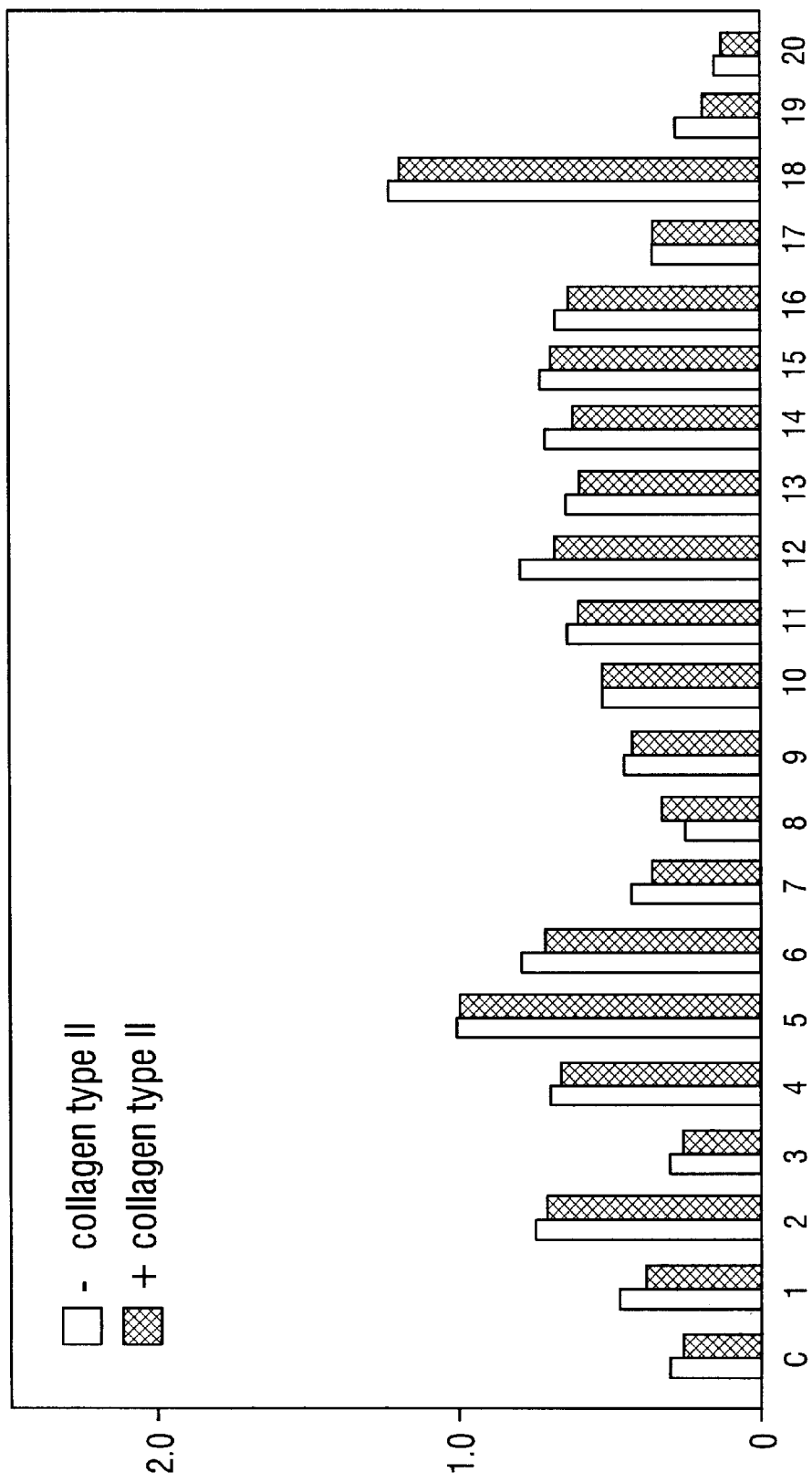
FIG. 7A is a graphic representation of the results of studies to detect human antibodies to M55 in accordance with the present invention.
Figure 7B:
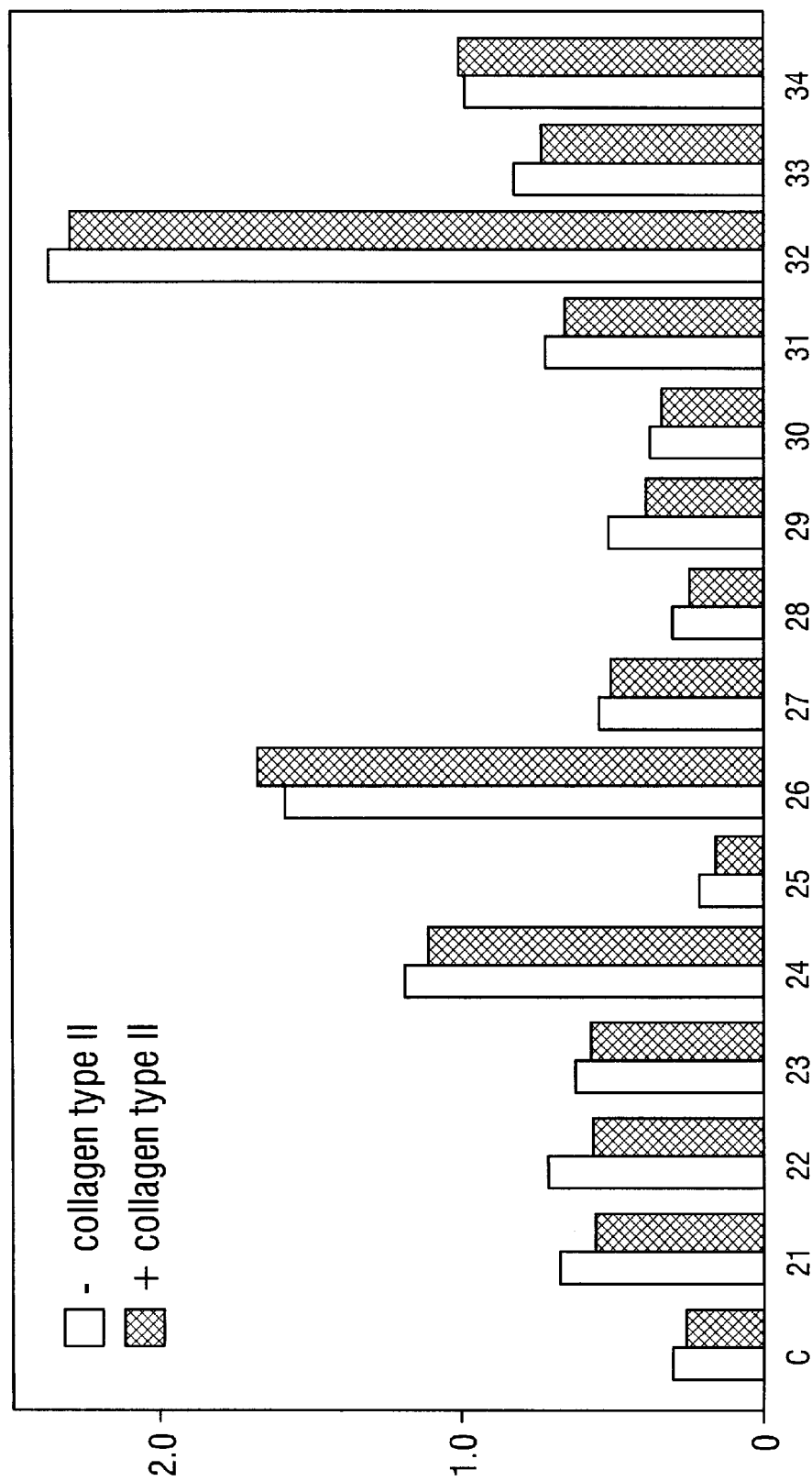
FIG. 7B is a graphic representation of the results of studies to detect human antibodies to M55 in accordance with the present invention.

Sera from 34 patients clinically diagnosed as having S. aureus infections were examined by ELISA. IgG that recognized the immobilized M55 (Col MSCRAMM) could be detected only when exceedingly high levels of antigen were used in the assay. Thus, despite the fact that these patients have had clinically diagnosed S. aureus infections, only a minor increase in α-CBP titers could be detected. These data (FIG. 7A and FIG. 7B) suggest that S. aureus infection may induce a polyclonal B-Cell activation that downregulates the human immune response to certain microbial cell wall components, including the CBP.

6. REFERENCES

The following literature citations as well as those cited above are incorporated in pertinent part by reference herein for the reasons cited in the above text:

U.S. Pat. No. 3,791,932.
U.S. Pat. No. 3,949,064.
U.S. Pat. No. 4,174,384.
U.S. Pat. No. 4,196,265.
U.S. Pat. No. 4,271,147.
U.S. Pat. No. 4,554,101.
U.S. Pat. No. 4,578,770.
U.S. Pat. No. 4,596,792.
U.S. Pat. No. 4,599,230.
U.S. Pat. No. 4,599,231.
U.S. Pat. No. 4,601,903.
U.S. Pat. No. 4,608,251.
U.S. Pat. No. 4,683,195.
U.S. Pat. No. 4,683,202.
Abraham et al., "Adherence of *Streptococcus pyogenes, Escherichia coli*, and *Pseudomonas aeruginosa* to Fibronectin-Coated and Uncoated Epithelial Cells," *Infect. Immun.*, 41:1261–1268, 1983.
Aleljung et al., *Curr. Microbiol.*, 28:231–236, 1994.
Allen and Choun, "Large Unilamellar Liposomes with Low Uptake into the Reticuloendothelial System," *FEBS Lett.*, 223:42–46, 1987.
Allen et al., *J. Bact.*, 173:916–920, 1991.
Bayer and Wilchek, "The use of the avidin-biotin complex as a tool for molecular biology," In: *Methods of Biochemical Analysis*, Glick, D., John Wiley and Sons, New York, 1980.
Bella et al., "Crystal and Molecular Structure of a Col-Like Peptide at 1.9 Å Resolution," *Science*, 266:75–81, 1994.
Bidanset, Guidry, Rosenberg, Choi, Timpl, Hook, "Binding of the Proteoglycan Decorin to Collagen Type VI," *J. Biol. Chem.*, 267:5250–5256, 1992.
Bolivar et al., *Gene*, 2:95, 1977.
Bremell et al., *Infect. Immun.*, 59(8):2615–2623, 1991.

Bremell et al., *Infect. Immun.*, 62(7):2976–2985, 1992.
Brunger et al., *Science*, 235:458–460, 1987.
Brunger, "X-PLOR Manual," Version 3.1, Yale Univ., New Haven, Conn., 1992.
Campbell, "Monoclonal Antibody Technology, Laboratory Techniques in Biochemistry and Molecular Biology," Burden and Von Knippenberg, Eds., Elsevier, Amsterdam, 13:75–83, 1984.
Capecchi, "High efficiency transformation by direct microinjection of DNA into cultured mammalian cells," *Cell*, 22(2):479–488, 1980.
Carret et al., *Ann. Inst. Pasteur Microbiol.*, 136A:241–45, 1985.
Carter et al., *Nucl. Acids Res.*, 12:4431–4443, 1985.
Chang et al., *Nature*, 375:615, 1978.
Chen et al., "An energetic evaluation of a "Smith" collagen microfibril model," *J. Protein Chem.*, 10:535–542, 1991.
China et al., *Infect. Immun.*, 61(8):3129–3136, 1993.
Chou and Fasman, "Conformational Parameters for Amino Acids in Helical, β-Sheet, and Random Coil Regions Calculated from Proteins," *Biochemistry*, 13(2):211–222, 1974b.
Chou and Fasman, "Empirical Predictions of Protein Conformation," *Ann. Rev. Biochem.*, 47:251–276, 1978b.
Chou and Fasman, "Prediction of β-Turns," *Biophys. J.*, 26:367–384, 1979.
Chou and Fasman, "Prediction of Protein Conformation," *Biochemistry*, 13(2):222–245, 1974a.
Clapp, "Somatic gene therapy into hematopoietic cells. Current status and future implications," *Clin. Perinatol.*, 20(1):155–168, 1993.
Cole et al., *J. Bone and Joint Surg.*, 64B:218, 1982.
Connolly, "Analytical Molecular Surface Calculation," *J. Appl. Cryst.*, 16:548–558, 1983.
Connolly, "The molecular surface package," *J. Mol. Graphics*, 11:139–141, 1993.
Couvreur et al., "Nanocapsules, a New Lysosomotropic Carrier," *FEBS Lett.*, 84:323–326, 1977.
Couvreur, "Polyalkyleyanoacrylates as Colloidal Drug Carriers," *Crit. Rev. Ther. Drug Carrier Syst.*, 5:1–20, 1988.
Cox et al., *J. Virol.*, 67(9):5664–5667, 1993.
Curiel et al., "Adenovirus enhancement of transferrin-polylysine-mediated gene delivery," *Proc. Natl. Acad. Sci. USA*, 88(19):8850–8854, 1991.
Emödy et al., *J. Bact.*, 171(12):6674–6679, 1989.
Fields et al., *Biopolymers*, 33:1695–1707, 1993.
Fiers et al., *Nature*, 273:113, 1978.
FRAMBO, Siemens Analytical X-Ray Instruments, 6300 Enterprise Lane, Madison, Wis. 53719, USA, 1989.
Fröman et al., "Binding of *Escherichia coli* to Fibronectin: A Mechanism of Tissue Adherence," *J. Biol. Chem.*, 259:14899–14905, 1984.
Fromm et al., "Expression of genes transferred into monocot and dicot plant cells by electroporation," *Proc. Natl. Acad. Sci. USA*, 82(17):5824–5828, 1985.
Furey and Swaminathan, *Amer. Crystal. Assoc. Meet. Abstr.*, 18:73, 1990.
Fynan et al., "DNA vaccines: protective immunizations by parenteral, mucosal, and gene gun inoculations," *Proc. Natl. Acad. Sci. USA*, 90(24):11478–11482, 1993.
Gabizon and Papahadjopoulos, "Liposomes formulations with prolonged circulation time in blood and enhanced uptake by tumors," *Proc. Natl. Acad. Sci. USA*, 85:6949–6953, 1988.
Goding, "Monoclonal Antibodies: Principles and Practice," 2nd Edition, Academic Pres Orlando, Fla., pp. 60–74, 1986.
Goeddel et al., *Nature*, 281:544, 1979.
Goeddel et al., *Nucl. Acids Res.*, 8:4057, 1980.
Goldenberg, *Arthritis Rheum.*, 32:496–502, 1989.
Graham and van der Eb, "Transformation of rat cells by DNA of human adenovirus 5," *Virology*, 54(2):536–539, 1973.
Granfors et al., *J. Infect. Dis.*, 141:424–429, 1980.
Granfors et al., *N. Engl. J Med.*, 320:216–221, 1989.
Harlow and Lane, "Antibodies: a Laboratory Manual," Cold Spring Harbor Laboratory, Cold Spring Harbor, N.Y., 1988.
Hay, "Cell Biology of Extracellular Matrix," New York, Plenum Press, 1991.
Hay, *Cell Biology of Extracellular Matrix*, 2nd ed., Plenum Press, New York, 1991.
Hedbom and Heinegard, *J. Biol. Chem.*, 264:6898–6905, 1989.
Heidemann and Roth, "Synthesis and Investigation of Collagen Model Peptides," *Adv. Polym. Sci.*, 43:143–203, 1982.
Henry-Michelland et al., "Attachment of Antibiotics to Nanoparticles; Preparation, Drug-Release and Antimicrobial Activity in vitro," *Int. J. Pharm.*, 35:121–127, 1987.
Hess et al., *J. Adv. Enzyme Reg.*, 7:149, 1968.
Hitzeman et al., *J. Biol. Chem.*, 255:2073, 1980.
Ho and Su, *J. Amer. Med. Assoc.*, 247:797–800, 1982,
Ho et al., "Site-Directed Mutagenesis by Overlap Extension Using the Polymerase Chain Reaction," *Gene*, 77:51–59, 1989.
Hochuli et al., *J. Chromatogr.*, 411:177–184, 1988.
Hodel et al., *Acta Crystallogr.*, A48:851–858, 1992.
Holderbaum et al., *Collagen Rel. Res.*, 5:261–271, 1985.
Holland et al., *Biochemistry*, 17:4900, 1978.
Hornick et al., *Infect. Immun.*, 60(4):1577–1588, 1992.
House-Pompeo, Boles, and Höök, "Characterization of Bacterial Adhesin Interactions with Extracellular Matrix Components Utilizing Biosensor Technology," *METHODS: A Companion to Meth. in Enzym.*, 6:134–142, 1994.
Ingham, Brew, Migliorini, *J. Biol. Chem.*, 264:16977–16980, 1989.
Jameson and Wolf, *Comp. Appl. Biosci.*, 4:181–186, 1988.
Jiang and Kim, "Soft Docking: Matching of Molecular Surface Cubes," *J. Mol. Biol.*, 219:79–102, 1991.
Joh et al., *Biochemistry*, 33(20):6086–6092, 1994.
Johnson, *Anal. Biochem.*, 206:215–225, 1992.
Jones et al., *Acta Cryst*, A47:110–119, 1991.
Jones, *Genetics*, 85:12 1977.
Kern et al., *Eur. J. Biochem.*, 215:151–159, 1993.
Kingsman et al., *Gene*, 7:141, 1979.
Kohler and Milstein, *Eur. J. Immunol.*, 6:511–519, 1976.
Kohler and Milstein, *Nature*, 256:495–497, 1975.
Kostrzynska et al., *FEMS Microbiol. Lett.*, 59:229–234, 1989.
Krumdieck et al., "The Proteoglycan Decorin Binds C1q and Inhibits the Activity of the C1 Complex," *J. Immunol.*, 149:3695–3701, 1992.
Kuby, "Immunology," 2nd Edition, W. H. Freeman & Company, New York, 1994.
Kyte and Doolittle, *J. Mol. Biol.*, 157(1):105–132, 1982.
Lantz et al., *J. Bacteriol.*, 173(14):4263–4270, 1991.
Laskowski et al., "PROCHECK: a program to check the stereochemical quality of protein structures," *J. Appl. Cryst.*, 26:283–291, 1993.
Laskowski et al., *J. Appl. Cryst.*, 26:283–291, 1993.
Liu and Gibbons, *Oral Micro. and Immun.*, 5(3):131–136, 1990.
Liu et al., *Oral Micro. and Immun.*, 5(3): 143–148, 1990.

Malmquist, *Nature*, 361:186–187, 1993.
Maloy, et al., "Microbial Genetics," 2nd Edition, Jones and Bartlett Publishers, Boston, Mass., 1994.
Maniatis et al., "Molecular Cloning: a Laboratory Manual," Cold Spring Harbor Laboratory, Cold Spring Harbor, N.Y., 1982.
Maxe et al., "Specific Attachment of *Staphylococcus aureus* to Immobilized Fibronectin," *Infect. Immun.*, 54:695–704, 1986.
McRee, Practical Protein Crystallography, Academic Press, 1993.
Merilahti-Palo, *Ann. Rheum. Dis.*, 50:87–90, 1991.
Miettinen et al., *Kidney*, 43:592–600, 1993.
Mumby, Raugi, Bornstein, *J. Cell Biol.*, 98:646–652, 1984.
Nakamura et al., "Enzyme Immunoassays: Heterogenous and Homogenous Systems," Chapter 27, 1987.
Nemethy et al., "Energy parameters in Polypeptides. 10. Improved Geometrical Parameters and Nonbonded Interactions for Use in the ECEPP/3 Algorithm, with Application to Proline-Containing Peptides," *J. Phys. Chem.*, 96:6472–6484, 1992.
Nicholls et al., *Proteins: Struct. Funct. Genet.*, 11:281–296, 1991.
Nowicki et al., *J. Exp. Med.*, 178(6):2115–2121, 1993.
O'Shannessy, *Anal. Biochem.*, 212:457–468, 1993.
Oldberg et al., *EMBO J.*, 8:2601–2606, 1989.
Patthy, *J. Mol. Biol.*, 198:567–577, 1987.
Patti et al., "Critical Residues in the Ligand-binding Site of the *Staphylococcus aureus* Collagen-binding Adhesin (MSCRAMM)," *J. Biol. Chem.*, 270:12005–12011, 1995.
Patti et al., "Molecular Characterization and Expression of a Gene Encoding a *Staphylococcus aureus* Collagen Adhesin," *J. Biol. Chem.*, 267:4766–4772, 1992.
Patti et al., "The *Staphylococcus aureus* Collagen Adhesin is a Virulence Determinant in Experimental Septic Arthritis," *Infect. Immun.*, 62:152–161, 1994.
Patti et al., *Biochemistry*, 32(42):11428–11435, 1993.
Patti et al., *Biol. Chem.*, 270:12005–12011, 1995.
Patti et al., *J. Biol. Chem.*, 267(7):4766–4772, 1992.
Patti, Allen, McGavin, Höök, *Annu. Rev. Microbiol.*, 48:585–617.1994.
Patti, Boles, Höök, "Identification and Biochemical Characterization of the Ligand Binding Domain of the Collagen Adhesin from *Staphylococcus aureus*," *Biochemistry*, 32:11428–11435, 1993.
Pilar Fernandez, Selmin, Martin, Yamada, Pfäffle, Deutzmann, Mollenhauer, von der Mark, *J. Biol. Chem.*, 263:5921–5925, 1988.
Pilz et al., *Infect. Immun.*, 60:189–195, 1992.
Porath et al., *Nature*, 258:598–599, 1975.
Prokop and Bajpai, "Recombinant DNA Technology I" *Ann. N.Y. Acad. Sci.*, Vol. 646, 1991.
Ramachandran and Reddi, "Biochemistry of Collagen," Plenum Press, New York, 1976.
Richardson, "The anatomy and taxonomy of protein structure," *Advances in Protein Chemistry*, 34:167–339, 1981.
Richardson, *Advances in Protein Chemistry*, 34:297–306, Academic Press, 1981.
Rubin, Höök, Öbrink, Timpl, "Substrate Adhesion of Rat Hepatocytes: Mechanism of Attachment to Collagen Substrates," *Cell*, 24:463–470, 1981.
Rydén et al., *Eur. J. Biochem.*, 184:331–336, 1989.
Sack, *J. Mol. Graphics*, 6:224–225, 1988.
Sakakibara et al., "Synthesis of (Pro-Hyp-Gly)$_n$ of defined molecular weights. Evidence for the stabilization of collagen triple helix by hydroxypyroline," *Biochim. Biophys. Acta*, 303:198–202, 1973.
Sambrook et al., "Molecular Cloning: A Laboratory Manual," 2nd Edition, Chapter 12.6, Cold Spring Harbor Laboratory, Cold Spring Harbor, N.Y., 1989.
Sanger, *Proc. Natl. Acad Sci. USA*, 74:5463–5467, 1977.
Santoro, *Cell*, 46:913–920, 1986.
Scatchard, *Ann. N.Y. Acad Sci.*, 51:660–672, 1949.
Schulze-Koops et al., *Infect. Immun.*, 60:2153–2159, 1992.
Schulze-Koops et al., *Infect. Immun.*, 61(6):2513–2519, 1993.
Segal and Traub, "Polymers of Tripeptides as Collagen Models. VI. Synthesis and Structural Investigation of Poly(L-alanyl-L-prolyl-glycine)," *J. Mol. Biol.*, 43:487–496, 1969.
Segal, "Biochemical Calculations," 2nd Edition, John Wiley and Sons, New York, 1976.
Smith et al., *Arthritis Rheum*, 25(4):441–446, 1982.
Smith et al., *J. Bone & Joint*, 69(7):1063–1068, 1987.
Speziale et al., "Binding of Collagen to *Staphylococcus aureus*," Cowan 1, *J. Bacteriol.*, 167:77–81, 1986.
Speziale et al., *FEMS Microbiol. Lett.*, 48:47–51, 1987.
Speziale et al., *J. Bacteriol.*, 167:77–81, 1986.
Stinchcomb et al., *Nature*, 282:39, 1979.
Switalski et al., "A collagen receptor on *Staphylococcus aureus* strains isolated from patients with septic arthritis mediates adhesion to cartilage," *Mol. Microbiol.*, 7:99–107, 1993.
Switalski et al., *Infect. Immun.*, 61(10):4119–4125, 1993.
Switalski et al., *J. Biol. Chem.*, 264(35):21080–21086, 1989.
Switalski et al., *Mol. Microbiol.*, 7(1):99–107, 1993.
Takada and Hemler, *J. Cell Biol.*, 109:397–407, 1989.
Takagi et al., *J. Biol. Chem.*, 266:5575–5579, 1991.
Takagi, *Biochem.*, 31:8530–8534, 1992.
Tamm et al., *Mol. Microbiol.*, 10:995–1011, 1993.
Tang et al., *Nature*, 356:152–154, 1992.
Tarkkanen et al., *Mol. Microbiol.*, 4(8):1353–1361, 1990.
Trust, et al., *Mol. Microbiol.*, 7(4):593–600, 1993.
Tschemper et al., *Gene*, 10:157, 1980.
Ulmer et al., "Heterologous Protection Against Influenza by Injection of DNA Encoding a Viral Protein," *Science*, 259:1745–1749, 1993.
Van Nhieu et al., "Bacterial Internalization Medicated by b1 Chain Integrins is Determined by Ligand Affinity and Receptor Density," *EMBO J.*, 12:1887–1895, 1993.
Vandenberg et al., "Characterization of a Type IV Collagen Major Cell Binding Site with Affinity to the $\alpha 1\beta 1$ and the $\alpha 2\beta 1$ Integrins," *J. Cell Biol.*, 113:1475–1483, 1991.
Vanderrest and Garrone, *FASEB J.*, 5:2814–2823, 1991.
Velge, *Parasitology*, 97:255–268, 1988.
Voytek et al., *Biomaterials*, 9:107–110, 1988.
Wagner et al., "Coupling of adenovirus to transferrin-polylysine/DNA complexes greatly enhances receptor-mediated gene delivery and expression of transfected genes," *Proc. Natl. Acad. Sci. USA*, 89(13):6099–6103, 1992.
Waldvogel et al., *N. Eng. J. Med.*, 303:360–369, 1980.
Wang et al., *J. Exp. Med.*, 177:699, 1993.
Wang et al., *J. Immunol.*, 150:3022, 1993.
Westerlund et al., *Mol. Microbiol.*, 3:329–337, 1989.
Whitton et al., *J. Virol.*, 67(1):348–352, 1993.
Wolf et al., *Compu. Appl. Biosci.*, 4(1):187–91, 1988.
Wong and Neumann, "Electric field mediated gene transfer," *Biochim. Biophys. Res. Commun.*, 107(2):584–587, 1982.
Woody, Peptides, Polypeptides, and Proteins, New York, Wiley, 1974.
Yamaguchi et al., "Negative Regulation of Transforming Growth Factor-b by the Proteoglycan Decorin," *Nature*, (London), 346:281–284, 1990.

Yang and Russel, *Proc. Natl. Acad. Sci. USA*, 87:4144–4148, 1990.

Bremell, T., Lange, S., Yacoub, A., Rydén, C. and Tarkowski, A. (1991) Experimental *Staphylococcus aureus* arthritis in mice. *Infect. Immun.* 59(8): 2615–2623.

Citri, E., Guidry, A. J., O'Brien, C. N. and Marquardt, W. W. (1995) Effect of alpha-toxin and capsular exoploysaccharide on the adherence of *Staphylococcus aureus* to cultered teat, ductal, and secretory mammary epithelial cells. *Res. Vet. Sci.* 50: 20–25.

Falkow, S., Isberg, R. R. and Portnoy, D. A. (1992) The Interaction of Bacteria with Mammalian Cells. *Annual Review of Cell Biology* 8: 333–363.

Fattom, A. I., Sarwar, J., Ortiz, A. and Naso, R. (1996) A *Staphylococcus aureus* capsular polysaccharide (CP) vaccine and CP-specific antibodies protect mice against bacterial challenge. *Infect Immun* 64(5): 1659–1665.

Foster, T. J. (1991) Potential for Vaccination Against Infections Caused by *Staphylococcus aureus*. *Vaccine* 9(4): 221–227.

Greco, D., Salmaso, S., Mastrantonio, P., Giuliano, M., Tozzi, A., et al. (1996) A controlled trial of two acellular vaccines and one whole-cell vaccine against pertussis. *N. Engl. J. Med.* 334: 341–348.

Greenberg, D. P., Ward, J. I. and Bayer, A. S. (1987) Influence of *Staphylococcus aureus* antibody on experimental endocarditis in rabbits. *Infect. Immun.* 55: 3030–3034.

Gudding, R., McDonald, J. D. and Cheville, N. F. (1984) Pathogenesis of *Staphylococcus aureus* mastitis: bacteriological, histological, and ultrstructural pathological findings. *Am. J. Vet. Sci.* 45: 2525–2531.

Gustaffson, L., Hallander, H. O., Olin, P., Reizenstein, E. and Storsaeter, J. (1996) A controlled trial of a two-component acellular, a five-component acellular, and a whole-cell pertussis vaccine. *N. Engl. J. Med.* 334: 349–355.

Joh, H. J., House-Pompeo, K., Patti, J. M., Gurusiddappa, S. and Hook, M. (1994) Fibronectin receptors from gram-positive bacteria: Comparison of active sites. *Biochemistry* 33(20): 6086–6092.

Karakawa, W. W., Sutton, A., Schneerson, R., Karpas, A. and Vann, W. F. (1988) Capsular antibodies induce type-specific phagocytosis of capsulated *Staphylococcus aureus* by human polymorphonuclear leukocytes. *Infect. Immun.* 56: 1090–1094.

Lepper, A. W. D., Atwell, J. L., Lehrbach, P. R., Schwartzkoff, C. L., Egerton, J. R., et al. (1995) The protective efficacy of cloned *Moraxella bovis* pill in monovalent and multivalent vaccine formulations against experimentally induced infectious bovine keratoconjunctivitis (IBK). *Vet Microbiol* 45(2–3): 129–138.

McDevitt, D., Francois, P., Vaudaux, P. and Foster, T. J. (1994) Molecular characterization of the clumping factor (fibrinogen receptor) of *Staphylococcus aureus*. *Mol. Micro.* 11(2): 237–248.

McQueen, C. E., Boedeker, E. C., Reid, R., Jarboe, D., Wolf, M., et al. (1993) Pili in microspheres protect rabbits from diarrhoea induced by *E. coli* strain RDEC-1. *Vaccine* 11: 201–206.

Menzies, B. E. and Kernodle, D. S. (1996) Passive immunization with antiserum to a nontoxic alpha-toxin mutant from *Staphylococcus aureus* is protective in a murine model. *Infect Immun* 64(5): 1839–1841.

Olmsted, S. B. and Norcross, N. L. (1992) Effect of specific antibody on adherence of *Staphylococcus aureus* to bovine mammary epithelial cells. *Infect. Immun.* 60(1): 249–256.

Patti, J. M., House-Pompeo, K., Boles, J. O., Garza, N., Gurusiddappa, G., et al. (1995) Critical residues in the ligand binding site of the *Staphylococcus aureus* Col-binding adhesin (MSCRAMM). *J. Biol. Chem.* 270: 12005–12001.

Poole-Warren, L. A., Hallett, M. D., Hone, P. W., Burden, S. H. and Farrell, P. C. (1991) Vaccination for prevention of CAPD associated staphylococcal infection: results of a prospective multicentre clinical trial. *Clinical Nephrology* 35: 198–206.

Ramisse, F., Szatanik, M., Binder, P. and Alonso, J. M. (1993) Passive Local Immunotherapy of Experimental Staphylococcal Pneumonia with Humar Intravenous Immunoglobulin. *Journal of Infectious Diseases* 168(4): 1030–1033.

Ryding, U., Christensson, B., Soderquist, B. and Wadstrom, T. (1995) Antibody response to *Staphylococcus aureus* Col binding protein in patients with *S-aureus* septicaemia and Col binding properties of corresponding strains. *J. Med Microbiol* 43(5): 328–334.

Sirakova, T., Kolattukudy, P. E., Murwin, D., Billy, J., Leake, E., et al. (1994) Role of Fimbriae Expressed by Nontypeable Haemophilus Influenzae in Pathogenesis of and Protection Against Otitis Media and Relatedness of the Fimbrin Subunit to Outer Membrane Protein a. *Infect. Immun.* 62(5): 2002–2020.

Welch, P. G., Fattom, A., Moore, J., Schneerson, R., Shiloach, J., et al. (1996) Safety and immunogenicity of *Staphylococcus aureus* type 5 capsular polysaccharide-pseudomonas aeruginosa recombinant exoprotein A conjugate vaccine in patients on hemodialysis. *J Amer Soc Nephrol* 7(2): 247–253.

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 441 base pairs
      (B) TYPE: nucleic acid
      (C) STRANDEDNESS: single
      (D) TOPOLOGY: linear (xi) SEQUENCE DESCRIPTION: SEQ ID NO: 1:

```
ATAACATCTG GGAATAAATC AACGAATGTT ACGGTTCATA AAAGTGAAGC GGGAACAAGT     60

AGTGTTTTCT ATTATAAAAC GGGAGATATG CTACCAGAAG ATACGACACA TGTACGATGG    120

TTTTTAAATA TTAACAATGA AAAAGTTAT GTATCGAAAG ATATTACTAT AAAGGATCAG     180

ATTCAAGGTG GACAGCAGTT AGATTTAAGC ACATTAAACA TTAATGTGAC AGGTACACAT    240

AGCAATTATT ATAGTGGACA AAGTGCAATT ACTGATTTTG AAAAAGCCTT TCCAGGTTCT    300

AAAATAACTG TTGATAATAC GAAGAACACA ATTGATGTAA CAATTCCACA AGGCTATGGG    360

TCATATAATA GTTTTTCAAT TAACTACAAA ACCAAAATTA CGAATGAACA GCAAAAAGAG    420

TTTGTTAATA ATTCACAAGC T                                             441
```

(2) INFORMATION FOR SEQ ID NO: 2:

(i) SEQUENCE CHARACTERISTICS:
        (A) LENGTH: 159 amino acids
        (B) TYPE: amino acid
        (C) STRANDEDNESS:
        (D) TOPOLOGY: linear (xi) SEQUENCE DESCRIPTION: SEQ ID NO: 2:

```
Met Arg Gly Ser His His His His His His Gly Ser Ile Thr Ser Gly
 1               5                  10                  15

Asn Lys Ser Thr Asn Val Thr Val His Lys Ser Glu Ala Gly Thr Ser
            20                  25                  30

Ser Val Phe Tyr Tyr Lys Thr Gly Asp Met Leu Pro Glu Asp Thr Thr
        35                  40                  45

His Val Arg Trp Phe Leu Asn Ile Asn Asn Glu Lys Ser Tyr Val Ser
    50                  55                  60

Lys Asp Ile Thr Ile Lys Asp Gln Ile Gln Gly Gln Gln Leu Asp
65                  70                  75                  80

Leu Ser Thr Leu Asn Ile Asn Val Thr Gly Thr His Ser Asn Tyr Tyr
                85                  90                  95

Ser Gly Gln Ser Ala Ile Thr Asp Phe Glu Lys Ala Phe Pro Gly Ser
            100                 105                 110

Lys Ile Thr Val Asp Asn Thr Lys Asn Thr Ile Asp Val Thr Ile Pro
        115                 120                 125

Gln Gly Tyr Gly Ser Tyr Asn Ser Phe Ser Ile Asn Tyr Lys Thr Lys
    130                 135                 140

Ile Thr Asn Glu Gln Gln Lys Glu Phe Val Asn Asn Ser Gln Ala
145                 150                 155
```

(2) INFORMATION FOR SEQ ID NO: 3:

(i) SEQUENCE CHARACTERISTICS:
        (A) LENGTH: 849 base pairs
        (B) TYPE: nucleic acid
        (C) STRANDEDNESS: single
        (D) TOPOLOGY: linear (xi) SEQUENCE DESCRIPTION: SEQ ID NO: 3:

```
GACGATAAAA ATGGAAAAAT ACAAAATGGT GACATGATTA AGTGGCATG GCCGACAAGC      60

GGTACAGTAA AGATAGAGGG TTATAGTAAA ACAGTACCAT TAACTGTTAA AGGTGAACAG    120

GTGGGTCAAG CAGTTATTAC ACCAGACGGT GCAACAATTA CATTCAATGA TAAAGTAGAA    180

AAATTAAGTG ATGTTTCGGG ATTTGCAGAA TTTGAAGTAC AAGGAAGAAA TTTAACGCAA    240
```

-continued

```
ACAAATACTT CAGATGACAA AGTAGCTACG ATAACATCTG GGAATAAATC AACGAATGTT      300

ACGGTTCATA AAAGTGAAGC GGGAACAAGT AGTGTTTTCT ATTATAAAAC GGGAGATATG      360

CTACCAGAAG ATACGACACA TGTACGATGG TTTTTAAATA TTAACAATGA AAAAGTTAT       420

GTATCGAAAG ATATTACTAT AAAGGATCAG ATTCAAGGTG ACAGCAGTT AGATTTAAGC       480

ACATTAAACA TTAATGTGAC AGGTACACAT AGCAATTATT ATAGTGGACA AAGTGCAATT      540

ACTGATTTTG AAAAGCCTT TCCAGGTTCT AAAATAACTG TTGATAATAC GAAGAACACA       600

ATTGATGTAA CAATTCCACA AGGCTATGGG TCATATAATA GTTTTTCAAT TAACTACAAA      660

ACCAAAATTA CGAATGAACA GCAAAAAGAG TTTGTTAATA ATTCACAAGC TTGGTATCAA      720

GAGCATGGTA AGGAAGAAGT GAACGGGAAA TCATTTAATC ATACTGTGCA CAATATTAAT      780

GCTAATGCCG GTATTGAAGG TACTGTAAAA GGTGAATTAA AAGTTTTAAA ACAGGATAAA      840

GATACCAAG                                                              849
```

(2) INFORMATION FOR SEQ ID NO: 4:

(i) SEQUENCE CHARACTERISTICS:
        (A) LENGTH: 211 amino acids
        (B) TYPE: amino acid
        (C) STRANDEDNESS:
        (D) TOPOLOGY: linear (xi) SEQUENCE DESCRIPTION: SEQ ID NO: 4:

```
Met Arg Gly Ser His His His His His His Gly Ser Asp Asp Lys Val
1               5                   10                  15

Ala Thr Ile Thr Ser Gly Asn Lys Ser Thr Asn Val Thr Val His Lys
            20                  25                  30

Ser Glu Ala Gly Thr Ser Ser Val Phe Tyr Tyr Lys Thr Gly Asp Met
        35                  40                  45

Leu Pro Glu Asp Thr Thr His Val Arg Trp Phe Leu Asn Ile Asn Asn
    50                  55                  60

Glu Lys Ser Tyr Val Ser Lys Asp Ile Thr Ile Lys Asp Gln Ile Gln
65                  70                  75                  80

Gly Gly Gln Gln Leu Asp Leu Ser Thr Leu Asn Ile Asn Val Thr Gly
                85                  90                  95

Thr His Ser Asn Tyr Tyr Ser Gly Gln Ser Ala Ile Thr Asp Phe Glu
            100                 105                 110

Lys Ala Phe Pro Gly Ser Lys Ile Thr Val Asp Asn Thr Lys Asn Thr
        115                 120                 125

Ile Asp Val Thr Ile Pro Gln Gly Tyr Gly Ser Tyr Asn Ser Phe Ser
    130                 135                 140

Ile Asn Tyr Lys Thr Lys Ile Thr Asn Glu Gln Gln Lys Glu Phe Val
145                 150                 155                 160

Asn Asn Ser Gln Ala Trp Tyr Gln Glu His Gly Lys Glu Val Asn
                165                 170                 175

Gly Lys Ser Phe Asn His Thr Val His Asn Ile Asn Ala Asn Ala Gly
            180                 185                 190

Ile Glu Gly Thr Val Lys Gly Glu Leu Lys Val Leu Lys Gln Asp Lys
        195                 200                 205

Asp Thr Lys
    210
```

(2) INFORMATION FOR SEQ ID NO: 5:

(i) SEQUENCE CHARACTERISTICS:

(A) LENGTH: 1500 base pairs
(B) TYPE: nucleic acid
(C) STRANDEDNESS: single
(D) TOPOLOGY: linear (xi) SEQUENCE DESCRIPTION: SEQ ID NO: 5:

```
GCACGAGATA TTTCATCAAC GAATGTTACA GATTTAACTG TATCACCGTC TAAGATAGAA      60
GATGGTGGTA AAACGACAGT AAAAATGACG TTCGACGATA AAAATGGAAA AATACAAAAT     120
GGTGACATGA TTAAAGTGGC ATGGCCGACA AGCGGTACAG TAAAGATAGA GGGTTATAGT     180
AAAACAGTAC CATTAACTGT TAAAGGTGAA CAGGTGGGTC AAGCAGTTAT TACACCAGAC     240
GGTGCAACAA TTACATTCAA TGATAAAGTA GAAAAATTAA GTGATGTTTC GGGATTTGCA     300
GAATTTGAAG TACAAGGAAG AAATTTAACG CAAACAAATA CTTCAGATGA CAAAGTAGCT     360
ACGATAACAT CTGGGAATAA ATCAACGAAT GTTACGGTTC ATAAAAGTGA AGCGGGAACA     420
AGTAGTGTTT TCTATTATAA AACGGGAGAT ATGCTACCAG AAGATACGAC ACATGTACGA     480
TGGTTTTTAA ATATTAACAA TGAAAAAAGT TATGTATCGA AGATATTAC TATAAAGGAT     540
CAGATTCAAG GTGGACAGCA GTTAGATTTA AGCACATTAA ACATTAATGT GACAGGTACA     600
CATAGCAATT ATTATAGTGG ACAAAGTGCA ATTACTGATT TTGAAAAAGC CTTTCCAGGT     660
TCTAAAATAA CTGTTGATAA TACGAAGAAC ACAATTGATG TAACAATTCC ACAAGGCTAT     720
GGGTCATATA ATAGTTTTTC AATTAACTAC AAAACCAAAA TTACGAATGA ACAGCAAAAA     780
GAGTTTGTTA ATAATTCACA AGCTTGGTAT CAAGAGCATG GTAAGGAAGA AGTGAACGGG     840
AAATCATTTA ATCATACTGT GCACAATATT AATGCTAATG CCGGTATTGA AGGTACTGTA     900
AAAGGTGAAT TAAAAGTTTT AAAACAGGAT AAAGATACCA AGGCTCCTAT AGCTAATGTA     960
AAATTTAAAC TTTCTAAAAA AGATGGATCA GTTGTAAAGG ACAATCAAAA AGAAATTGAG    1020
ATTATAACAG ATGCAAACGG TATTGCTAAT ATTAAAGCGT TGCCTAGTGG AGACTATATT    1080
TTAAAAGAAA TAGAGGCGCC ACGACCGTAT ACATTTGATA AGGATAAAGA ATATCCGTTT    1140
ACTATGAAAG ATACAGATAA TCAGGGATAT TTTACGACTA TTGAAAATGC AAAAGCGATA    1200
GAAAAAACAA AAGATGTTTC TGCTCAAAAG GTTTGGGAAG GCACTCAAAA AGTGAAACCA    1260
ACGATTTATT TCAAGTTGTA CAAACAAGAT GACAATCAAA ATACAACACC AGTAGACAAA    1320
GCAGAGATTA AAAAATTAGA AGATGGAACG ACAAAAGTGA CATGGTCTAA TCTTCCGGAA    1380
AATGACAAAA ATGGCAAGGC TATTAAATAT TTAGTTAAAG AAGTAAATGC TCAAGGTGAA    1440
GATACAACAC CAGAAGGATA TACTAAAAAA GAAAATGGTT TAGTGGTTAC TAATACTGAA    1500
```

(2) INFORMATION FOR SEQ ID NO: 6:

(i) SEQUENCE CHARACTERISTICS:
(A) LENGTH: 512 amino acids
(B) TYPE: amino acid
(C) STRANDEDNESS:
(D) TOPOLOGY: linear (xi) SEQUENCE DESCRIPTION: SEQ ID NO: 6:

```
Met Arg Gly Ser His His His His His His Gly Ser Ala Arg Asp Ile
 1               5                  10                  15

Ser Ser Thr Asn Val Thr Asp Leu Thr Val Ser Pro Ser Lys Ile Glu
            20                  25                  30

Asp Gly Gly Lys Thr Thr Val Lys Met Thr Phe Asp Asp Lys Asn Gly
        35                  40                  45

Lys Ile Gln Asn Gly Asp Met Ile Lys Val Ala Trp Pro Thr Ser Gly
    50                  55                  60
```

-continued

```
Thr Val Lys Ile Glu Gly Tyr Ser Lys Thr Val Pro Leu Thr Val Lys
 65                  70                  75                  80

Gly Glu Gln Val Gly Gln Ala Val Ile Thr Pro Asp Gly Ala Thr Ile
                 85                  90                  95

Thr Phe Asn Asp Lys Val Glu Lys Leu Ser Asp Val Ser Gly Phe Ala
            100                 105                 110

Glu Phe Glu Val Gln Gly Arg Asn Leu Thr Gln Thr Asn Thr Ser Asp
        115                 120                 125

Asp Lys Val Ala Thr Ile Thr Ser Gly Asn Lys Ser Thr Asn Val Thr
130                 135                 140

Val His Lys Ser Glu Ala Gly Thr Ser Ser Val Phe Tyr Tyr Lys Thr
145                 150                 155                 160

Gly Asp Met Leu Pro Glu Asp Thr Thr His Val Arg Trp Phe Leu Asn
                165                 170                 175

Ile Asn Asn Glu Lys Ser Tyr Val Ser Lys Asp Ile Thr Ile Lys Asp
            180                 185                 190

Gln Ile Gln Gly Gly Gln Gln Leu Asp Leu Ser Thr Leu Asn Ile Asn
        195                 200                 205

Val Thr Gly Thr His Ser Asn Tyr Tyr Ser Gly Gln Ser Ala Ile Thr
210                 215                 220

Asp Phe Glu Lys Ala Phe Pro Gly Ser Lys Ile Thr Val Asp Asn Thr
225                 230                 235                 240

Lys Asn Thr Ile Asp Val Thr Ile Pro Gln Gly Tyr Gly Ser Tyr Asn
                245                 250                 255

Ser Phe Ser Ile Asn Tyr Lys Thr Lys Ile Thr Asn Glu Gln Gln Lys
            260                 265                 270

Glu Phe Val Asn Asn Ser Gln Ala Trp Tyr Gln Glu His Gly Lys Glu
        275                 280                 285

Glu Val Asn Gly Lys Ser Phe Asn His Thr Val His Asn Ile Asn Ala
290                 295                 300

Asn Ala Gly Ile Glu Gly Thr Val Lys Gly Glu Leu Lys Val Leu Lys
305                 310                 315                 320

Gln Asp Lys Asp Thr Lys Ala Pro Ile Ala Asn Val Lys Phe Lys Leu
                325                 330                 335

Ser Lys Lys Asp Gly Ser Val Val Lys Asp Asn Gln Lys Glu Ile Glu
            340                 345                 350

Ile Ile Thr Asp Ala Asn Gly Ile Ala Asn Ile Lys Ala Leu Pro Ser
        355                 360                 365

Gly Asp Tyr Ile Leu Lys Glu Ile Glu Ala Pro Arg Pro Tyr Thr Phe
370                 375                 380

Asp Lys Asp Lys Glu Tyr Pro Phe Thr Met Lys Asp Thr Asp Asn Gln
385                 390                 395                 400

Gly Tyr Phe Thr Thr Ile Glu Asn Ala Lys Ala Ile Glu Lys Thr Lys
                405                 410                 415

Asp Val Ser Ala Gln Lys Val Trp Glu Gly Thr Gln Lys Val Lys Pro
            420                 425                 430

Thr Ile Tyr Phe Lys Leu Tyr Lys Gln Asp Asp Asn Gln Asn Thr Thr
        435                 440                 445

Pro Val Asp Lys Ala Glu Ile Lys Lys Leu Glu Asp Gly Thr Thr Lys
450                 455                 460

Val Thr Trp Ser Asn Leu Pro Glu Asn Asp Lys Asn Gly Lys Ala Ile
465                 470                 475                 480
```

```
Lys Tyr Leu Val Lys Glu Val Asn Ala Gln Gly Glu Asp Thr Thr Pro
                485                 490                 495

Glu Gly Tyr Thr Lys Lys Glu Asn Gly Leu Val Val Thr Asn Thr Glu
                500                 505                 510
```

(2) INFORMATION FOR SEQ ID NO: 7:

(i) SEQUENCE CHARACTERISTICS:
        (A) LENGTH: 345 amino acids
        (B) TYPE: amino acid
        (C) STRANDEDNESS:
        (D) TOPOLOGY: linear (xi) SEQUENCE DESCRIPTION: SEQ ID NO: 7:

```
Met Arg Gly Ser His His His His His His Gly Ser Met Val Ala Ala
1               5                   10                  15

Asp Ala Pro Ala Ala Gly Thr Asp Ile Thr Asn Gln Leu Thr Asn Val
                20                  25                  30

Thr Val Gly Ile Asp Ser Gly Thr Thr Val Tyr Pro His Gln Ala Gly
                35                  40                  45

Tyr Val Lys Leu Asn Tyr Gly Phe Ser Val Pro Asn Ser Ala Val Lys
50                  55                  60

Gly Asp Thr Phe Lys Ile Thr Val Pro Lys Glu Leu Asn Leu Asn Gly
65                  70                  75                  80

Val Thr Ser Thr Ala Lys Val Pro Pro Ile Met Ala Gly Asp Gln Val
                85                  90                  95

Leu Ala Asn Gly Val Ile Asp Ser Asp Gly Asn Val Ile Tyr Thr Phe
                100                 105                 110

Thr Asp Tyr Val Asn Thr Lys Asp Asp Val Lys Ala Thr Leu Thr Met
                115                 120                 125

Pro Ala Tyr Ile Asp Pro Glu Asn Val Lys Lys Thr Gly Asn Val Thr
                130                 135                 140

Leu Ala Thr Gly Ile Gly Ser Thr Thr Ala Asn Lys Thr Val Leu Val
145                 150                 155                 160

Asp Tyr Glu Lys Tyr Gly Lys Phe Tyr Asn Leu Ser Ile Lys Gly Thr
                165                 170                 175

Ile Asp Gln Ile Asp Lys Thr Asn Asn Thr Tyr Arg Gln Thr Ile Tyr
                180                 185                 190

Val Asn Pro Ser Gly Asp Asn Val Ile Ala Pro Val Leu Thr Gly Asn
                195                 200                 205

Leu Lys Pro Asn Thr Asp Ser Asn Ala Leu Ile Asp Gln Gln Asn Thr
210                 215                 220

Ser Ile Lys Val Tyr Lys Val Asp Asn Ala Ala Asp Leu Ser Glu Ser
225                 230                 235                 240

Tyr Phe Val Asn Pro Glu Asn Phe Glu Asp Val Thr Asn Ser Val Asn
                245                 250                 255

Ile Thr Phe Pro Asn Pro Asn Gln Tyr Lys Val Glu Phe Asn Thr Pro
                260                 265                 270

Asp Asp Gln Ile Thr Thr Pro Tyr Ile Val Val Val Asn Gly His Ile
                275                 280                 285

Asp Pro Asn Ser Lys Gly Asp Leu Ala Leu Arg Ser Thr Leu Tyr Gly
                290                 295                 300

Tyr Asn Ser Asn Ile Ile Trp Arg Ser Met Ser Trp Asp Asn Glu Val
305                 310                 315                 320

Ala Phe Asn Asn Gly Ser Gly Ser Gly Asp Gly Ile Asp Lys Pro Val
                325                 330                 335
```

```
Val Pro Glu Gln Pro Asp Glu Gln Ala
            340                 345

(2) INFORMATION FOR SEQ ID NO: 8:

(i) SEQUENCE CHARACTERISTICS:
        (A) LENGTH: 139 amino acids
        (B) TYPE: amino acid
        (C) STRANDEDNESS:
        (D) TOPOLOGY: linear (xi) SEQUENCE DESCRIPTION: SEQ ID NO: 8:

Met Arg Gly Ser His His His His His Gly Ser Glu Gly Gly Gln
1               5                   10                  15

Asn Ser Gly Asn Gln Ser Phe Glu Glu Asp Thr Glu Glu Asp Lys Pro
            20                  25                  30

Lys Tyr Glu Gln Gly Gly Asn Ile Val Asp Ile Asp Phe Asp Ser Val
            35                  40                  45

Pro Gln Ile His Gly Gln Asn Lys Gly Asn Gln Ser Phe Glu Glu Asp
            50                  55                  60

Thr Glu Lys Asp Lys Pro Lys Tyr Glu His Gly Gly Asn Ile Ile Asp
65                  70                  75                  80

Ile Asp Phe Asp Ser Val Pro His Ile His Gly Phe Asn Lys His Thr
                85                  90                  95

Glu Ile Ile Glu Glu Asp Thr Asn Lys Asp Lys Pro Ser Tyr Gln Phe
                100                 105                 110

Gly Gly His Asn Ser Val Asp Phe Glu Glu Asp Thr Leu Pro Lys Val
            115                 120                 125

Ser Gly Gln Asn Glu Phe Asp Ile Lys Leu Asn
            130                 135
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defmed by the appended claims. Accordingly, the exclusive rights sought to be patented are as described in the claims.

What is claimed is:

1. An isolated antibody which binds to a purified peptide composition consisting essentially of the amino acid of SEQ ID NO:6, wherein said antibody prevents *S.aureus* infection.

2. An antibody according to claim 1, wherein said antibody prevents *S. aureus* infection in a human.

3. An antibody according to claim 1, wherein said antibody is suitable for parenteral, oral, intranasal, subcutaneous, or intravenous administration to an animal.

4. An antibody according to claim 1 wherein the antibody is a monoclonal antibody.

5. An antibody according to claim 1 wherein the antibody is a polyclonal antibody.

6. An isolated antisera containing an antibody according to claim 1.

7. An isolated antibody which binds to a purified peptide composition consisting essentially of the amino acid of SEQ ID NO:6, wherein said antibody trates *S. aureus* infection when said antibody is administered to an infected animal.

8. An antibody according to claim 7 wherein said antibody is a monoclonal antibody.

9. An antibody according to claim 7 wherein said polyclonal antibody.

10. An antibody according to claim 7 wherein said animal is a human.

11. An antibody according to claim 7 wherein said antibody is suitable for parenteral, oral, intranasal, subcutaneous, or intravenous administration to said animal.

12. An isolated antisera containing an antibody according to claim 7.

* * * * *

UNITED STATES PATENT AND TRADEMARK OFFICE
CERTIFICATE OF CORRECTION

PATENT NO. : 6,288,214 B1
DATED : September 11, 2001
INVENTOR(S) : Magnus Hook et al.

It is certified that error appears in the above-identified patent and that said Letters Patent is hereby corrected as shown below:

Title page,
Item [75], delete "Narayana Sthanam" and "Jindrich Symersky" as inventors.

Column 7,
Line 62, insert the following claims:

13.   An isolated antibody which binds to a purified peptide composition encoded by a nucleic acid sequence consisting essentially of the sequence of SEQ ID NO:5, wherein said antibody prevents *S. aureus* infection.

14.   An isolated antibody which binds to a purified peptide composition encoded by a nucleic acid sequence consisting essentially of the sequence of SEQ ID NO:5, wherein said antibody treats *S. aureus* infection when said antibody is administered to an infected animal. --

Column 86,
Line 49, delete "trates" and substitute -- treats -- therefor.

Signed and Sealed this

Fourteenth Day of May, 2002

*Attest:*

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO. : 6,288,214 B1
DATED : September 11, 2001
INVENTOR(S) : Magnus Hook et al.

It is certified that error appears in the above-identified patent and that said Letters Patent is hereby corrected as shown below:

Title page,
Item [75], Inventors, delete "Narayana Sthanam" and "Jindrich Symersky" as inventors.

Column 86,
Line 62, insert the following claims:

13. An isolated antibody which binds to a purified peptide composition encoded by a nucleic acid sequence consisting essentially of the sequence of SEQ ID NO:5, wherein said antibody prevents *S. aureus* infection.

14. An isolated antibody which binds to a purified peptide composition encoded by a nucleic acid sequence consisting essentially of the sequence of SEQ ID NO:5, wherein said antibody treats *S. aureus* infection when said antibody is administered to an infected animal. --

Column 86,
Line 49, delete "trates" and substitute -- treats -- therefor.

This certificate supersedes Certificate of Correction issued May 14, 2002.

Signed and Sealed this

Twenty-sixth Day of November, 2002

Attest:

JAMES E. ROGAN
*Attesting Officer*                *Director of the United States Patent and Trademark Office*